United States Patent
Li et al.

(10) Patent No.: US 9,540,637 B2
(45) Date of Patent: Jan. 10, 2017

(54) NUCLEIC ACID ADAPTORS AND USES THEREOF

(75) Inventors: Bin Li, Palo Alto, CA (US); Zhoutao Chen, Carlsbad, CA (US); Tanya Biorac, Escondido, CA (US); Melvin Shiwade Wei, San Marcos, CA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 709 days.

(21) Appl. No.: 13/877,203

(22) PCT Filed: Sep. 29, 2011

(86) PCT No.: PCT/US2011/054053
§ 371 (c)(1),
(2), (4) Date: Jun. 3, 2013

(87) PCT Pub. No.: WO2012/044847
PCT Pub. Date: Apr. 5, 2012

(65) Prior Publication Data
US 2013/0261027 A1    Oct. 3, 2013

Related U.S. Application Data

(63) Continuation-in-part of application No. 12/350,837, filed on Jan. 8, 2009, now Pat. No. 8,530,197.
(Continued)

(51) Int. Cl.
*C12Q 1/68* (2006.01)
*C12P 19/34* (2006.01)
*C12N 15/10* (2006.01)

(52) U.S. Cl.
CPC ......... *C12N 15/1093* (2013.01); *C12Q 1/6806* (2013.01)

(58) Field of Classification Search
USPC ..................... 435/6.12, 91.2, 91.1
See application file for complete search history.

(56) References Cited

U.S. PATENT DOCUMENTS

| 4,710,465 A | 12/1987 | Weissman et al. |
| 5,229,273 A | 7/1993 | Gottesman et al. |

(Continued)

FOREIGN PATENT DOCUMENTS

| WO | WO-00/58522 | 10/2000 |
| WO | WO-01/079553 | 10/2001 |

(Continued)

OTHER PUBLICATIONS

Briggs, Adrian et al., "Patterns of damage in genomic DNA sequences from a Neandertal", *PNAS*, vol. 104, No. 37, 2007, 14616-14621.

(Continued)

*Primary Examiner* — Kenneth Horlick

(57) ABSTRACT

Provided herein are compositions, systems, methods, and kits for joining together the ends of one or more polynucleotides using at least one pair of blocking oligonucleotide adaptors. Blocking oligonucleotide adaptors can be used to reduce the formation of adaptor dimers or trimers (or higher-order concatemers) which can improve the yield of desirable polynucleotide-adaptor products in any recombinant nucleic acid workflow. Blocking oligonucleotide adaptors can comprise a double-stranded oligonucleotide adaptor (duplex) having an overhang cohesive portion that anneals with a blocking oligonucleotide which can be a separate single-stranded oligonucleotide. A blocking oligonucleotide, when annealed to an overhang portion, can prevent undesirable hybridization of the overhang portion to another (Continued)

nucleic acid, such as the overhang portion from another blocking oligonucleotide adaptor or a polynucleotide of interest.

16 Claims, 8 Drawing Sheets

Related U.S. Application Data

(60) Provisional application No. 61/438,259, filed on Feb. 1, 2011, provisional application No. 61/498,405, filed on Jun. 17, 2011, provisional application No. 61/469,587, filed on Mar. 30, 2011, provisional application No. 61/389,121, filed on Oct. 1, 2010, provisional application No. 61/426,229, filed on Dec. 22, 2010, provisional application No. 61/020,114, filed on Jan. 9, 2008, provisional application No. 61/109,638, filed on Oct. 30, 2008.

(56) References Cited

U.S. PATENT DOCUMENTS

| | | |
|---|---|---|
| 5,434,066 A | 7/1995 | Bebee et al. |
| 5,468,614 A | 11/1995 | Fields et al. |
| 5,658,736 A | 8/1997 | Wong et al. |
| 5,695,937 A | 12/1997 | Kinzler et al. |
| 5,866,330 A | 2/1999 | Kinzler et al. |
| 5,925,523 A | 7/1999 | Dove et al. |
| 5,968,784 A | 10/1999 | Spinella et al. |
| 5,981,190 A | 11/1999 | Israel |
| 6,054,276 A | 4/2000 | Macevicz |
| 6,114,600 A | 9/2000 | Ow et al. |
| 6,136,537 A | 10/2000 | Macevicz |
| 6,200,759 B1 | 3/2001 | Dove et al. |
| 6,235,472 B1 | 5/2001 | Landegren et al. |
| 6,383,743 B1 | 5/2002 | Kinzler et al. |
| 6,465,254 B1 | 10/2002 | Saito et al. |
| 6,498,013 B1 | 12/2002 | Velculescu et al. |
| 6,551,828 B1 | 4/2003 | Clark |
| 6,720,179 B1 | 4/2004 | Macevicz |
| 7,425,431 B2 | 9/2008 | Church et al. |
| 7,601,499 B2 | 10/2009 | Berka et al. |
| 7,754,429 B2 | 7/2010 | Rigatti et al. |
| 7,851,158 B2 | 12/2010 | McKernan |
| 8,071,296 B2 | 12/2011 | Ruan et al. |
| 8,192,930 B2 | 6/2012 | Vermaas et al. |
| 8,846,347 B2 | 9/2014 | Shendure et al. |
| 2002/0076716 A1 | 6/2002 | Sabanayagam et al. |
| 2002/0106646 A1 | 8/2002 | Remacle et al. |
| 2003/0008290 A1 | 1/2003 | Velculescu et al. |
| 2003/0036069 A1 | 2/2003 | Su |
| 2003/0049653 A1 | 3/2003 | Kinzler et al. |
| 2004/0002090 A1 | 1/2004 | Mayer et al. |
| 2004/0082001 A1 | 4/2004 | Macevicz |
| 2005/0164214 A1 | 7/2005 | Pruitt et al. |
| 2006/0024681 A1 | 2/2006 | Smith et al. |
| 2008/0213771 A1 | 9/2008 | Drmanac et al. |
| 2009/0093378 A1 | 4/2009 | Bignell et al. |
| 2009/0156431 A1 | 6/2009 | Lok |
| 2009/0181861 A1 | 7/2009 | Li et al. |
| 2009/0233291 A1 | 9/2009 | Chen et al. |
| 2009/0239764 A1 | 9/2009 | Sparks et al. |
| 2009/0264299 A1 | 10/2009 | Drmanac et al. |
| 2009/0325239 A1 | 12/2009 | Lok |
| 2010/0028888 A1 | 2/2010 | Smith et al. |
| 2010/0120034 A1 | 5/2010 | McKernan et al. |

FOREIGN PATENT DOCUMENTS

| | | |
|---|---|---|
| WO | WO-03/074734 | 9/2003 |
| WO | WO-03/106678 | 12/2003 |
| WO | WO-2005/042781 | 5/2005 |
| WO | WO-2005/082098 | 9/2005 |
| WO | WO-2007/044245 | 4/2007 |
| WO | WO-2007/091077 | 8/2007 |
| WO | WO-2007/145612 | 12/2007 |
| WO | WO-2009/089384 | 7/2009 |
| WO | WO-2010/003153 | 1/2010 |

OTHER PUBLICATIONS

Fullwood, M. J. et al., "Next-generation DNA sequencing of paired-end tags (PET) for transcriptome and genome analyses", *Genome Research*, vol. 19, No. 4, 2009, 521-532.

Korbel, Jan et al., "Paired-End Mapping Reveals Extensive Structural Variation in the Human Genome", *Science*, vol. 318, 2007, 420-426.

Ng, et al., "Multiplex sequencing of paired-end ditags (MS-PET): a strategy for the ultra-high-throughput analysis of transcriptomes and genomes", *Nucleic Acids Research*, vol. 34, No. 12, 2006, e84.

Ng, Patrick et al., "Gene identification signature (GIS) analysis for transcriptome characterization and genome annotation", *Nature Methods*, vol. 2, No. 2, 2005, 105-111.

PCT/US2009/030490, International Search Report mailed Jun. 5, 2009.

PCT/US2011/054053, International Search Report and Written Opinion mailed Mar. 5, 2012, 1-11.

Porreca, Gregory et al., "Polony DNA Sequencing", *Current Protocols in Molecular Biology*, 2006, 7.8.1-7.8.22.

Shendure, J et al., "Accurate Multiplex Polony Sequencing of an Evolved Bacterial Genome", Science, vol. 309, 2005, 1728-1732.

Albert, Henrik et al., "Site-specific integration of DNA into wild-type and mutant lox sites placed in the plant genome", *The Plant Journal*, vol. 7, No. 4, Blackwell Science Ltd., 1995, 649-659.

Belfort, et al., "Homing endonucleases: keeping the house in order", *Nucleic Acids Research*, vol. 25, No. 17, Sep. 1, 1997, 3379-3388.

CN200980108336.7, First Search Report mailed Oct. 9, 2012 (Translation).

Dove, S L. et al., "Bacterial Two-Hybrid Analysis ofInteractions Between Region 4 of the A70 Subunit ofRNA Polymerase and the Transcriptional Regulators Rsd from *Escherichia coli* and AlgQ from Pseudomonas aeruginosa", *Journal of Bacteriology*, vol. 183, No. 21, 2001, 6413-6421.

Dove, Simon et al., "Conversion of the W Subunit of *Escherichia coli* RNA Polymerase Into a Transcriptional Activator or an Activation Target", *Genes & Development, Journal of Cellular and Molecular Biology*, 12, 1998, 745-754.

Dunn, John J. et al., "Genomic Signature Tags (GSTs); A System for Profiling Genomic DNA", *Genome Research*, vol. 12, 2002, 1756-1765.

Fields, Stanley et al., "A novel genetic system to detect protein—protein interactions", *Nature*, vol. 340, 1989, 245-246.

Genbank, GI:208958 [online], [retrieved on May 17, 2010] retrieved from :http://www.ncbi.nlm.nih.gov/sviewerlviewer. fcgi?val=208958&sat=OLDID&satkey=146275, Mar. 26,1992, pp. 1-6.

Genbank, GI:287325315 [online] May 23, 2010, retrieved from: http://www.ncbi.nlm.nih.gov/nuccore/287325315, [retrieved on Oct 30, 2010, 4 pages.

Genbank, GI:6691170 [online] Jan. 12, 2000, retrieved from http://www.ncbi. nlrri.nih.gov/nuccore/6691170?sat=NCBI &satkey=1779208, [retrieved on Oct. 31, 2010.

Genbank, GI:160358355 [online] Dec. 11, 2013 [retrieved on Dec. 22, 2013], retrieved from http://www.ncbi.nlm.nih.gov/nuccore/ NG_007075.1, Dec. 11, 2013.

Genbank, GI:451770431 [online] Dec. 15, 2013 [retrieved on Dec. 22, 2013] retrieved from: http://www.ncbi.nlm.nih.gov/NG_ 016465, Dec. 15, 2013.

Genbank, GI:451770431 [online] Dec. 15, 2013 [retrieved on Dec. 23, 2013] retrieved from: http://www.ncbi.nlm.nih.gov/nuccore/ 451770431 ?report=fasta&to=2600, Dec. 15, 2013.

Hall, Neil, "Advanced sequencing technologies and their wider impact in microbiology", *The Journal of Experimental Biology*, 209, 2007, 1518-1525.

(56) References Cited

OTHER PUBLICATIONS

Harmon, et al., "Biochemical characterization of the DNA helicase activity of the *Escherichia coli* RecQ helicase", *J. Biol. Chem.* 276 (1 ):, Jan. 5, 2001, 232-243.
Heiter, Daniel et al., "Site-Specific DNA-nicking Mutants of the Heterodimeric Restriction Endonuclease R.BbvCI", J. Mol. Biol., 348, 2005, 631-640.
Kent, W et al., "Assembly of the Working Draft of the Human Genome with GigAssembler", *Genome Research*, vol. 11, 2001, pp. 1541-1548.
Malek, J. A. et al., "Annotation of Novel Proteins Utilizing a Functional Genome Shotgun Coupled with High-throughput Protein Interaction Mapping", *Cold Spring Harbor Symposia on Quantitative Biology*, vol. LXVIII, 2003, 331-334.
Malek, Joel A. et al., "Protein Interaction Mapping on a Functional Shotgun Sequence of Rickettsia sibirica", *Nucleic Acids Research*, Oxford University Press, vol. 32, No. 3, 2004, 1059-1064.
Mullikin, J et al., "The Phusion Assembler", *Genome Research*, vol. 13, 2003, pp. 81-90.
New England Biolabs, information on Bdal restriction endonuclease [online], retrieved from: http://www.neb.com/nebecomm/EnzymeFinderSearchByName.asp, [retrieved on Oct. 30, 2010.
New England Biolabs Catalog, 1993/94, (cover and pp. 20,30,42,43,150 and 151.
PCT/US09/30490, International Preliminary Report on Patentability mailed Jul. 22, 2010.
PCT/US2004/036141, International Preliminary Report on Patentability mailed on Mar. 29, 2006, 6.

PCT/US2004/036141, International Search Report mailed Sep. 5, 2005, 3.
PCT/US2004/036141, Written Opinion, mailed Sep. 5, 2005, 4.
Phizicky, Eric et al., "Protein analysis on a proteomic scale", *Nature*, 422 (6928), 2003, 208-215.
Rigby, Peter et al., "Labeling Deoxyribonucleic Acid to High Specific Activity in Vitro by Nick Translation with DNA Polymerase I", *J. Mol. Biol.*, vol. 113, 1977, pp. 237-251.
Roach, Jared et al., "Pairwise End Sequencing: A Unified Approach to Genomic Mapping and Sequencing", *Genomics*, 26, 1995, 345-353.
Samuelson, James et al., "The isolation of strand-specific nicking endonucleases from a randomized Sapl expression library", *Nucleic Acids Research*, vol. 32, No. 12, 2004, 3661-3671.
Shuman, "Recombination mediated by vaccinia virus DNA topoisomerase I in *Escherichia coli* is sequence specific", *Proceedings of the National Academy of Sciences (PNAS)*, vol. 88, No. 22,, Nov. 1991, 10104-10108.
Siegel, Andrew et al., "Modeling the Feasibility of Whole Genome Shotgun Sequencing Using a Pairwise End Strategy", *Genomics*, 68, 2000, 237-246.
Velculescu, et al., "Serial Analysis of Gene Expression", *Science*, vol. 270, No. 5235, 1995, 484-487.
Wang, T. et al., "Digital Karyotyping", *PNAS*, vol.(99(25),), 2002, 16156-16161.
Zhang, Zuwen et al., "Cre Recombinase-Mediated Inversion Using Iox66 and Iox 71: Method to Introduce Conditional Point Mutations Into the CREB-binding Protein", *Nucleic Acids Research*. vol. 30, No. i7, 2002, e90.
Zhu, Zhenyu et al., "Engineering Strand-specific DNA Nicking Enzymes from the Type IIS Restriction Endonucleases Bsal, BsmBl, and BsmAI", *J. Mol. Biol.*, 337, 2004, 573-583.

NUCLEIC ACID ADAPTORS AND USES THEREOF

CROSS-REFERENCE TO RELATED APPLICATIONS

This application is a national stage application under 35 U.S.C. §371 of International Application No. PCT/US2011/054053, filed on Sep. 29, 2011, which claims the filing date benefit of U.S. Provisional Application No. 61/389,121, filed on Oct. 1, 2010, and 61/426,229, filed on Dec. 22, 2010, and 61/438,259, filed on Feb. 1, 2011, and 61/469,587, filed on Mar. 30, 2011, and 61/498,405, filed on Jun. 17, 2011; this application is also a continuation-in-part of U.S. Ser. No. 12/350,837, filed on Jan. 8, 2009, which claims the filing date benefit of U.S. Provisional Application No. 61/020,114, filed on Jan. 9, 2009, and U.S. 61/109,638, filed on Oct. 30, 2008.

Throughout this application various publications are referenced. The disclosures of these publications in their entireties are hereby incorporated by reference into this application in order to more fully describe the state of the art to which this invention pertains.

FIELD

The present disclosure relates to compositions, systems, methods and kits for joining the ends of one or more polynucleotides together with one or more oligonucleotide adaptor(s).

INTRODUCTION

Nucleic acid manipulations can often involve joining together the ends of two or more different polynucleotides, or joining together two ends of one polynucleotide for circularization. For example, nucleic acid sample preparation or library preparation workflows can include at least one joining step mediated by one or more nucleic acid adaptors. The resulting constructs can be sequenced in a next-generation sequencing process, in which large numbers of relatively small nucleic acid fragments can be sequenced at the same time in parallel.

SUMMARY

Provided herein are compositions, systems, methods and kits for joining together the ends of one or more polynucleotides with at least one pair of blocking oligonucleotide adaptors. Blocking oligonucleotide adaptors can be used to reduce the formation of adaptor dimers or trimers (or higher-order concatemers) which can improve the yield of desirable polynucleotide-adaptor products in any recombinant nucleic acid workflow. A joining step can include joining together two or more different polynucleotides together, or can include joining together two ends of one polynucleotide to form a circular molecule.

Provided herein are nucleic acid compositions, comprising: a first nucleic acid overhang having a first nucleic acid sequence and a second nucleic acid overhang having a second nucleic acid sequence, the first and second nucleic acid sequences can be at least partially complementary to each other, wherein the first overhang can be hybridized to a first blocking oligonucleotide over at least a portion of its length and the second overhang can be hybridized to a second blocking oligonucleotide over at least a portion of its length. In some embodiments, a first nucleic acid overhang can comprise a first double-stranded nucleic acid adaptor. In some embodiments, a second nucleic acid overhang can comprise a second double-stranded nucleic acid adaptor. In some embodiments, a first or a second double-stranded nucleic acid adaptor can comprise biotin.

Provided herein are nucleic acid compositions, comprising: a first nucleic acid duplex with a first overhang wherein the first overhang includes a first nucleic acid sequence and a second nucleic acid duplex with a second overhang wherein the second overhang includes a second nucleic acid sequence, the first and second nucleic acid sequences can be at least partially complementary to each other, wherein the first overhang can be hybridized to a first blocking oligonucleotide over at least a portion of its length and the second overhang can be hybridized to a second blocking oligonucleotide over at least a portion of its length. In some embodiments, a first nucleic acid duplex can comprise a first double-stranded nucleic acid adaptor. In some embodiments, a second nucleic acid duplex can comprise a second double-stranded nucleic acid adaptor. In some embodiments, a first or a second double-stranded nucleic acid adaptor can comprise biotin.

Provided herein are nucleic acid compositions, comprising: a first nucleic acid duplex with a first overhang wherein the first overhang includes a first nucleic acid sequence and a second nucleic acid duplex with a second overhang wherein the second overhang includes a second nucleic acid sequence, the first and second nucleic acid sequences can be at least partially complementary to each other, wherein the first overhang can be hybridized to a first blocking oligonucleotide over at least a portion of its length and the second overhang can be hybridized to a second blocking oligonucleotide over at least a portion of its length, wherein the first nucleic acid duplex can be joined to one end of a first polynucleotide and the second nucleic acid duplex can be joined to the one end of a second polynucleotide. In some embodiments, a first and a second polynucleotide can comprise double-stranded polynucleotides. In some embodiments, a first and a second polynucleotide can comprise polynucleotides of interest. In some embodiments, a first or a second double-stranded nucleic acid adaptor can comprise biotin. In some embodiments, a first and a second polynucleotide can be double-stranded polynucleotides and can form part of a single contiguous double-stranded nucleic acid molecule. In some embodiments, a first and a second polynucleotide can be double stranded polynucleotides and can form part of different double-stranded nucleic acid molecules. In some embodiments, a first nucleic acid duplex can comprise a first double-stranded nucleic acid adaptor. In some embodiments, a second nucleic acid duplex can comprise a second double-stranded nucleic acid adaptor.

In some embodiments nucleic acid compositions can include a first blocking oligonucleotide which can comprise a single-stranded oligonucleotide.

In some embodiments nucleic acid compositions can include a second blocking oligonucleotide which can comprise a single-stranded oligonucleotide.

In some embodiments nucleic acid compositions can include a first blocking oligonucleotide and a second blocking oligonucleotide that are not hybridized to each other.

In some embodiments nucleic acid compositions can include a first overhang which can be located at an end of a first nucleic acid duplex, a second overhang which can be located at an end of a second nucleic acid duplex, where hybridization of the first overhang to the first blocking oligonucleotide can form a third nucleic acid duplex, where hybridization of the second overhang to the second blocking oligonucleotide can form a fourth nucleic acid duplex, and where the melting point of the first nucleic acid duplex and of the second nucleic acid duplex can both be substantially greater than the melting points of both the third and fourth nucleic acid duplexes.

In some embodiments nucleic acid compositions can include a first overhang which can be located at an end of a first nucleic acid duplex, a second overhang which can be located at an end of a second nucleic acid duplex, where hybridization of the first overhang to the first blocking oligonucleotide can form a third nucleic acid duplex, where hybridization of the second overhang to the second blocking oligonucleotide can form a fourth nucleic acid duplex, and wherein the melting point of the first nucleic acid duplex can be substantially greater than the melting point of the third nucleic acid duplex.

In some embodiments nucleic acid compositions can include a first overhang which can be located at an end of a first nucleic acid duplex, a second overhang which can be located at an end of a second nucleic acid duplex, where hybridization of the first overhang to the first blocking oligonucleotide can form a third nucleic acid duplex, where hybridization of the second overhang to the second blocking oligonucleotide can form a fourth nucleic acid duplex, and where the melting point of the second nucleic acid duplex can be substantially greater than the melting point of the fourth nucleic acid duplex.

In some embodiments nucleic acid compositions can include a first nucleic acid overhang which can comprise one end of a first polynucleotide and can include a second nucleic acid overhang which can comprise one end of a second polynucleotide.

In some embodiments, a first and a second polynucleotide can be double-stranded polynucleotides and can form part of a single contiguous double-stranded nucleic acid molecule.

In some embodiments, a first and a second polynucleotides can be double stranded polynucleotides and can form part of different double-stranded nucleic acid molecules.

Provided herein are methods for joining a first and a second nucleic acid, comprising the step(s): providing a first nucleic acid overhang having a first nucleic acid sequence and a second nucleic acid overhang having a second nucleic acid sequence, the first and second nucleic acid sequences can be at least partially complementary to each other, wherein the first overhang can be hybridized to a first blocking oligonucleotide over at least a portion of its length and the second overhang can be hybridized to a second blocking oligonucleotide over at least a portion of its length. In some embodiments, the methods can further comprise the step(s): separating the first blocking oligonucleotides from the first nucleic acid overhangs. In some embodiments, the methods can further comprise the step(s): separating the second blocking oligonucleotides from the second nucleic acid overhangs. In some embodiments, the first blocking oligonucleotides can be separated from the first nucleic acid overhangs and the second blocking oligonucleotides can be separated from the second nucleic acid overhangs essentially simultaneously or sequentially. In some embodiments, the methods can further comprise the step(s): hybridizing the first nucleic acid sequence with the second nucleic acid sequence, thereby joining together the first and the second nucleic acid overhangs. In some embodiments, a first nucleic acid overhang can comprise a first double-stranded nucleic acid adaptor. In some embodiments, a second nucleic acid overhang can comprise a second double-stranded nucleic acid adaptor. In some embodiments, a first or a second double-stranded nucleic acid adaptor can comprise biotin.

Optionally, a first blocking oligonucleotide can be a single-stranded oligonucleotide. Optionally, a second blocking oligonucleotide can be a single-stranded oligonucleotide. Optionally, a first blocking oligonucleotide and the second blocking oligonucleotide are not hybridized to each other. Optionally, a first overhang can be located at an end of a first nucleic acid duplex, the second overhang can be located at an end of a second nucleic acid duplex, the hybridization of the first overhang to the first blocking oligonucleotide can form a third nucleic acid duplex, the hybridization of the second overhang to the second blocking oligonucleotide can form a fourth nucleic acid duplex, and the melting point of the first nucleic acid duplex and of the second nucleic acid duplex can be both substantially greater than the melting points of both the third and fourth nucleic acid duplexes. Optionally, a first overhang can be located at an end of a first nucleic acid duplex, the second overhang can be located at an end of a second nucleic acid duplex, the hybridization of the first overhang to the first blocking oligonucleotide can form a third nucleic acid duplex, the hybridization of the second overhang to the second blocking oligonucleotide can form a fourth nucleic acid duplex, and the melting point of the first nucleic acid duplex can be substantially greater than the melting point of the third nucleic acid duplex. Optionally, a first overhang can be located at an end of a first nucleic acid duplex, the second overhang can be located at an end of a second nucleic acid duplex, the hybridization of the first overhang to the first blocking oligonucleotide can form a third nucleic acid duplex, the hybridization of the second overhang to the second blocking oligonucleotide can form a fourth nucleic acid duplex, and the melting point of the second nucleic acid duplex can be substantially greater than the melting point of the fourth nucleic acid duplex. Optionally, the first double-stranded nucleic acid adaptor can include a first nucleic acid overhang having the sequence 5'-CTGCTGTACCGTACATCCGCCTTG-3'(SEQ ID NO:1), and a second oligonucleotide which is complementary to the first nucleic acid overhang can have the sequence 3'-GACGACATGGCA-5' (SEQ ID NO:2), and a first blocking oligonucleotide can have the sequence 3'-TGTAGGCGGAA-5' (SEQ ID NO:3). Optionally, a second double-stranded nucleic acid adaptor can include a second nucleic acid overhang having the sequence 3'-TGTAGGCGGAACCGGCATGTCGTC-5'(SEQ ID NO:6), and a second oligonucleotide which is complementary to the second nucleic acid overhang can have the sequence 5'-GCCGTACAGCAG-3' (SEQ ID NO:5), and a second blocking oligonucleotide can have the sequence 5'-CATCCGCCTTG-3' (SEQ ID NO:4). Optionally, a first double-stranded nucleic acid adaptor can include a first nucleic acid overhang having the sequence 5'-CTGCTGTACCGTACATCCGCCTTGGCC-3'(SEQ ID NO:14), and a second oligonucleotide which is complementary to the first nucleic acid overhang can have the sequence 3'-GACGACATG-5' (SEQ ID NO:15), and a first blocking oligonucleotide can have the sequence 3'-TGTAGGCGGAAC-5' (SEQ ID NO:16). Optionally, a first double-stranded nucleic acid adaptor can include a first nucleic acid overhang having the sequence 3'-GCATGTAGGCGGAACCGGCATGTCGTC-5'(SEQ ID NO:13), and a second oligonucleotide which is complementary to the second nucleic acid overhang can have the sequence 5'-GTACAGCAG-3' (SEQ ID NO:12), and a second blocking oligonucleotide can have the sequence 5'-ACATCCGCCTTG-3' (SEQ ID NO:11).

Provided herein are methods for joining a first and a second nucleic acid, comprising the step(s): providing a first nucleic acid duplex with a first overhang wherein the first overhang can have a first nucleic acid sequence and a second nucleic acid duplex with a second overhang wherein the second overhang can have a second nucleic acid sequence, the first and second nucleic acid sequences can be at least partially complementary to each other, wherein the first overhang can be hybridized to a first blocking oligonucleotide over at least a portion of its length and the second overhang can be hybridized to a second blocking oligonucleotide over at least a portion of its length. In some embodiments, the methods can further comprise the step(s): separating the first blocking oligonucleotides from the first nucleic acid overhangs. In some embodiments, the methods can further comprise the step(s): separating the second blocking oligonucleotides from the second nucleic acid overhangs. In some embodiments, the first blocking oligonucleotides can be separated from the first nucleic acid overhangs and the second blocking oligonucleotides can be separated from the second nucleic acid overhangs essentially simultaneously or sequentially. In some embodiments, the methods can further comprise the step(s): hybridizing the first nucleic acid sequence with the second nucleic acid sequence to join together the first and the second overhangs thereby joining the first and second nucleic acid duplexes. In some embodiments, a first nucleic acid duplex can comprise a first double-stranded nucleic acid adaptor. In some embodiments, a second nucleic acid duplex can comprise a second double-stranded nucleic acid adaptor. In some embodiments, a first or a second double-stranded nucleic acid adaptor can comprise biotin.

Provided herein are methods for joining a first and a second nucleic acid, comprising the step(s): providing a first nucleic acid duplex with a first overhang wherein the first overhang includes a first nucleic acid sequence and a second nucleic acid duplex with a second overhang wherein the second overhang includes a second nucleic acid sequence, the first and second nucleic acid sequences can be at least partially complementary to each other, wherein the first overhang can be hybridized to a first blocking oligonucleotide over at least a portion of its length and the second overhang can be hybridized to a second blocking oligonucleotide over at least a portion of its length, and wherein the first nucleic acid duplex can be joined to an end of a first polynucleotide and the second nucleic acid duplex can be joined to an end of a second polynucleotide. In some embodiments, the methods can further comprise the step(s): separating the first blocking oligonucleotide from the first overhang. In some embodiments, the methods can further comprise the step(s): separating the second blocking oligonucleotide from the second overhang. In some embodiments, the first blocking oligonucleotides can be separated from the first nucleic acid overhangs and the second blocking oligonucleotides can be separated from the second nucleic acid overhangs essentially simultaneously or sequentially. In some embodiments, the methods can further comprise the step(s): hybridizing the first nucleic acid sequence with the second nucleic acid sequence to join together the first and the second overhangs thereby joining the first and second nucleic acid duplexes. In some embodiments, a first nucleic acid duplex can comprise a first double-stranded nucleic acid adaptor. In some embodiments, a second nucleic acid duplex can comprise a second double-stranded nucleic acid adaptor. In some embodiments, a first or a second double-stranded nucleic acid adaptor can comprise biotin. In some embodiments, a first polynucleotide can be a double-stranded polynucleotide. In some embodiments, a second polynucleotide can be a double-stranded polynucleotide. In some embodiments, a first polynucleotide can comprise a polynucleotide of interest. In some embodiments, a second polynucleotide can comprise a polynucleotide of interest. In some embodiments, a first and a second polynucleotide can be double-stranded polynucleotides and can form part of a single contiguous double-stranded nucleic acid molecule. In some embodiments, a first and a second polynucleotide can be double stranded polynucleotides and can form part of different double-stranded nucleic acid molecules.

In some embodiments, in methods for joining a first and a second nucleic acid, a first nucleic acid overhang can comprise one end of a first polynucleotide and a second nucleic acid overhang can comprise one end of a second polynucleotide.

In some embodiments, in methods for joining a first and a second nucleic acid, a first and a second polynucleotide can be double-stranded polynucleotides and can form part of a single contiguous double-stranded nucleic acid molecule.

In some embodiments, in methods for joining a first and a second nucleic acid, joining together the first and the second nucleic acid overhangs in step (c) can include circularizing the first and second polynucleotides.

In some embodiments, in methods for joining a first and a second nucleic acid, a first and a second polynucleotide can be double stranded polynucleotides and can form part of different double-stranded nucleic acid molecules.

In some embodiments, in methods for joining a first and a second nucleic acid, the separating the first blocking oligonucleotide from the first overhangs can comprise denaturing the first single-stranded blocking oligonucleotide from the first overhang.

In some embodiments, in methods for joining a first and a second nucleic acid, the separating the second blocking oligonucleotide from the second overhangs can comprise denaturing the second single-stranded blocking oligonucleotide from the second overhang.

In some embodiments, in methods for joining a first and a second nucleic acid, methods for joining a first and a second nucleic acid can further comprise a step: ligating the hybridized first and the second nucleic acid sequences with a ligase enzyme.

In some embodiments, in methods for joining a first and a second nucleic acid, the first nucleic acid sequence so hybridized with the second nucleic acid sequence to join together the first and the second overhangs forms a junction on each nucleic acid strand between the joined first and the second nucleic acid overhangs.

In some embodiments, in methods for joining a first and a second nucleic acid, at least one junction can comprise a nick.

In some embodiments, in methods for joining a first and a second nucleic acid, methods for joining a first and a second nucleic acid can further comprise a step: moving the nick to a new position.

In some embodiments, in methods for joining a first and a second nucleic acid, a nick can be moved to a new position within the polynucleotide.

In some embodiments, in methods for joining a first and a second nucleic acid, the moving the nick to a new position within the polynucleotide can be conducted with a nick translation reaction on the nick.

In some embodiments, in methods for joining a first and a second nucleic acid, a nick translation reaction can be a coupled 5' to 3' DNA polymerization/degradation reaction, or can be a coupled 5' to 3' DNA polymerization/strand displacement reaction.

In some embodiments, in methods for joining a first and a second nucleic acid, the length of time of a nick translation reaction can be modulated to increase or decrease the distance to move the nick to a new position within the polynucleotide of interest.

Provided herein are joined first and second nucleic acid overhangs prepared by the methods of the present teachings.

In some embodiments, methods for joining a first and a second nucleic acid can further comprise the step(s): degrading at least a portion of the strand having the nick, thereby opening the nick into a gap.

In some embodiments, methods for joining a first and a second nucleic acid can further comprise the step(s): cleaving the strand opposite the gap thereby releasing a linear mate pair construct.

In some embodiments, in methods for joining a first and a second nucleic acid, a degrading reaction can be performed with any exonuclease enzyme (e.g., T7 exonuclease).

In some embodiments, in methods for joining a first and a second nucleic acid, a cleaving reaction can be performed with a single-strand specific endonuclease enzyme.

Provided herein are released linear mate pair constructs prepared by the methods of the present teachings.

Provided herein is a mate pair library, comprising two or more released linear mate pair constructs which are prepared by the methods of the present teachings.

In some embodiments, methods for joining a first and a second nucleic acid can further comprise the step of reacting the biotin with streptavidin.

In some embodiments, methods for joining a first and a second nucleic acid can further comprise the step: joining at least one end of a released linear mate pair construct to at least one amplification adaptor and/or sequencing adaptor.

In some embodiments, methods for joining a first and a second nucleic acid can further comprise the step: amplifying the released linear mate pair construct.

In some embodiments, methods for joining a first and a second nucleic acid can further comprise the step: sequencing the released linear mate pair construct.

In some embodiments, methods for joining a first and a second nucleic acid can further comprise the step: sequencing the released linear mate pair construct with a semiconductor based sequencing platform or ion sensitive sequencing platform.

DRAWINGS

The skilled artisan will understand that the drawings, described below, are for illustration purposes only. The drawings are not intended to limit the scope of the present teachings in any way.

FIG. 1A is a schematic showing a non-limiting example of a left and a right blocking oligonucleotide adaptor used to circularize a polynucleotide of interest. (Top) A left and a right blocking oligonucleotide adaptor each comprising a duplex of a first and second single-stranded oligonucleotide with an overhang portion, and a third single-stranded oligonucleotide (blocking oligonucleotide) annealed to an overhang portion. Left and right blocking adaptors can be joined to a double-stranded polynucleotide of interest. (Bottom) A third single-stranded oligonucleotide (blocking oligonucleotide) can be removed and the overhang portions from the left and right blocking oligonucleotide adaptors anneal with each other to circularize the polynucleotide of interest. For the sake of clarity, the diagram shows only a portion of the polynucleotide of interest.

FIG. 1B is a schematic showing a non-limiting example of a left and a right blocking oligonucleotide adaptor used to circularize a polynucleotide of interest. (Top) A left and a right blocking oligonucleotide adaptor each comprising a duplex of a first and second single-stranded oligonucleotide with an overhang portion, and a third single-stranded oligonucleotide (blocking oligonucleotide) annealed to an overhang portion. Left and right blocking adaptors can be joined to a double-stranded polynucleotide of interest. (Bottom) A third single-stranded oligonucleotide (blocking oligonucleotide) can be removed and the overhang portions from the left and right blocking oligonucleotide adaptors anneal with each other to circularize the polynucleotide of interest. For the sake of clarity, the diagram shows only a portion of the polynucleotide of interest.

FIG. 2 is a schematic showing a non-limiting example of a left and a right blocking oligonucleotide adaptor used to circularize a polynucleotide of interest. (Top) a left and a right blocking oligonucleotide adaptor each comprising a duplex of a first and second single-stranded oligonucleotide with an overhang portion, and a third single-stranded oligonucleotide (first blocking oligonucleotide) annealed to an overhang portion, and a fourth single-stranded oligonucleotide (second blocking oligonucleotide) annealed to the overhang portion formed by the third single-stranded oligonucleotide. Left and right blocking adaptors can be joined to a double-stranded polynucleotide of interest. (Bottom) The third and fourth single-stranded oligonucleotides (first and second blocking oligonucleotides) can be removed and the overhang portions from the left and right blocking oligonucleotide adaptors anneal with each other to circularize the polynucleotide of interest. For the sake of clarity, the diagram shows only a portion of the polynucleotide of interest.

Figure 6:
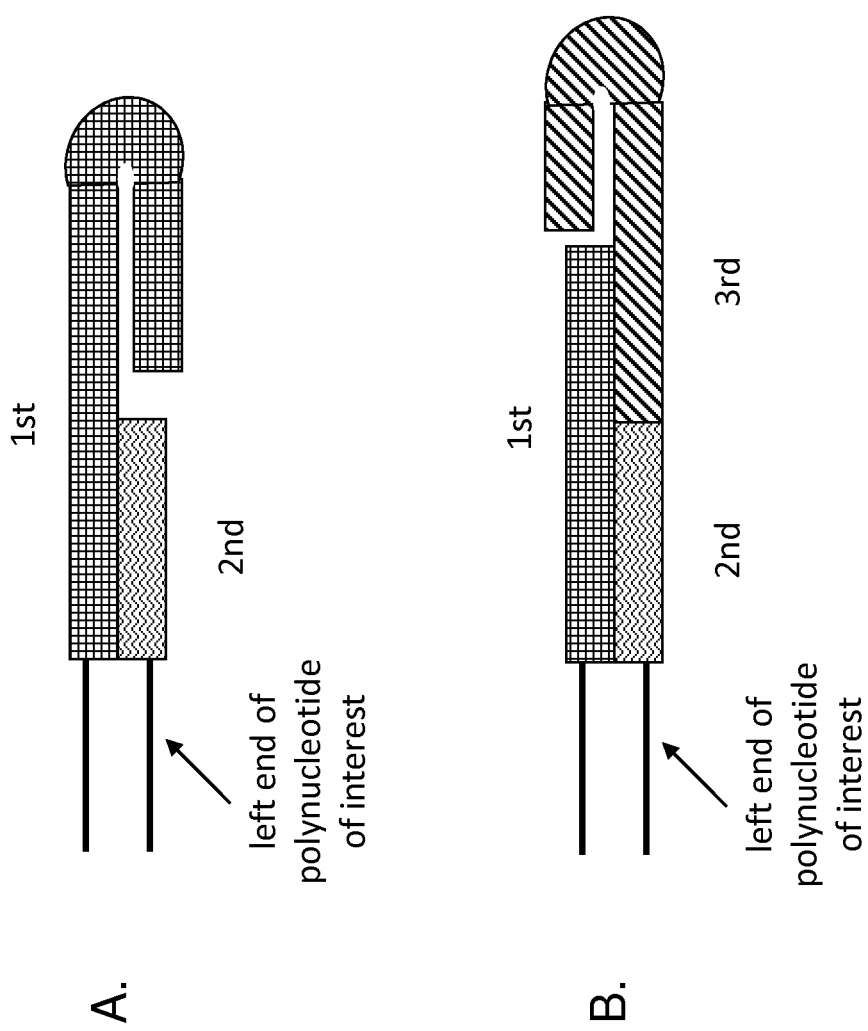

FIGS. 6A and B are schematics showing a non-limiting example of a blocking oligonucleotide adaptor having a hairpin structure.

Figure 7:
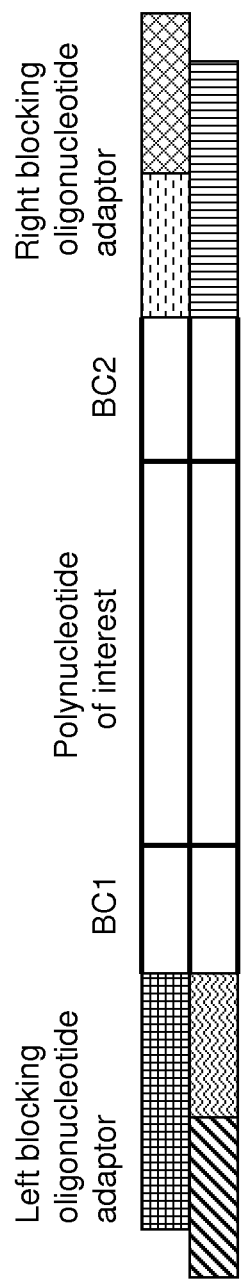

FIG. 7 is a schematic depicting a non-limiting example of a polynucleotide of interest joined to two different barcode adaptors (BC1, BC2) which can be joined to a left and right blocking oligonucleotide adaptor. This construct is shown prior to a circularization step.

DEFINITIONS

Unless otherwise defined, scientific and technical terms used in connection with the present teachings described herein shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used, for example, for nucleic acid purification and preparation, chemical analysis, recombinant nucleic acid, and oligonucleotide synthesis. Enzymatic reactions and purification techniques are performed according to manufacturer's specifications or as commonly accomplished in the art or as described herein. The techniques and procedures described herein are generally performed according to conventional methods well known in the art and as described in various general and more specific references that are cited and discussed throughout the instant specification. See, e.g., Sambrook et al., Molecular Cloning: A Laboratory Manual (Third ed., Cold Spring Harbor Laboratory Press, Cold Spring Harbor, N.Y. 2000). The nomenclatures utilized in connection with, and the laboratory procedures and techniques described herein are those well known and commonly used in the art.

As utilized in accordance with exemplary embodiments provided herein, the following terms, unless otherwise indicated, shall be understood to have the following meanings:

DESCRIPTION OF VARIOUS EMBODIMENTS

The section headings used herein are for organizational purposes only and are not to be construed as limiting the described subject matter in any way. Unless defined otherwise, all technical and scientific terms used herein have the same meaning as is commonly understood by one of ordinary skill in the art to which these inventions belong. All patents, patent applications, published applications, treatises and other publications referred to herein, both supra and infra, are incorporated by reference in their entirety. If a definition and/or description is set forth herein that is contrary to or otherwise inconsistent with any definition set forth in the patents, patent applications, published applications, and other publications that are herein incorporated by reference, the definition and/or description set forth herein prevails over the definition that is incorporated by reference. It will be appreciated that there is an implied "about" prior to the temperatures, concentrations, times, etc discussed in the present teachings, such that slight and insubstantial deviations are within the scope of the present teachings herein. In this application, the use of the singular includes the plural unless specifically stated otherwise. Also, the use of "comprise", "comprises", "comprising", "contain", "contains", "containing", "include", "includes", and "including" are not intended to be limiting. As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present). It is to be understood that both the foregoing general description and the following detailed description are exemplary and explanatory only and are not restrictive of the invention.

Provided herein are compositions, systems, methods, and kits for joining together the ends of one or more polynucleotides using at least one pair of blocking oligonucleotide adaptors. Blocking oligonucleotide adaptors can be used to reduce the formation of adaptor dimers or trimers (or higher-order concatemers) which can improve the yield of desirable polynucleotide-adaptor products in any recombinant nucleic acid workflow. A joining step can include joining together two or more different polynucleotides together, or joining together two ends of one polynucleotide to form a circular molecule.

Figure 1A:
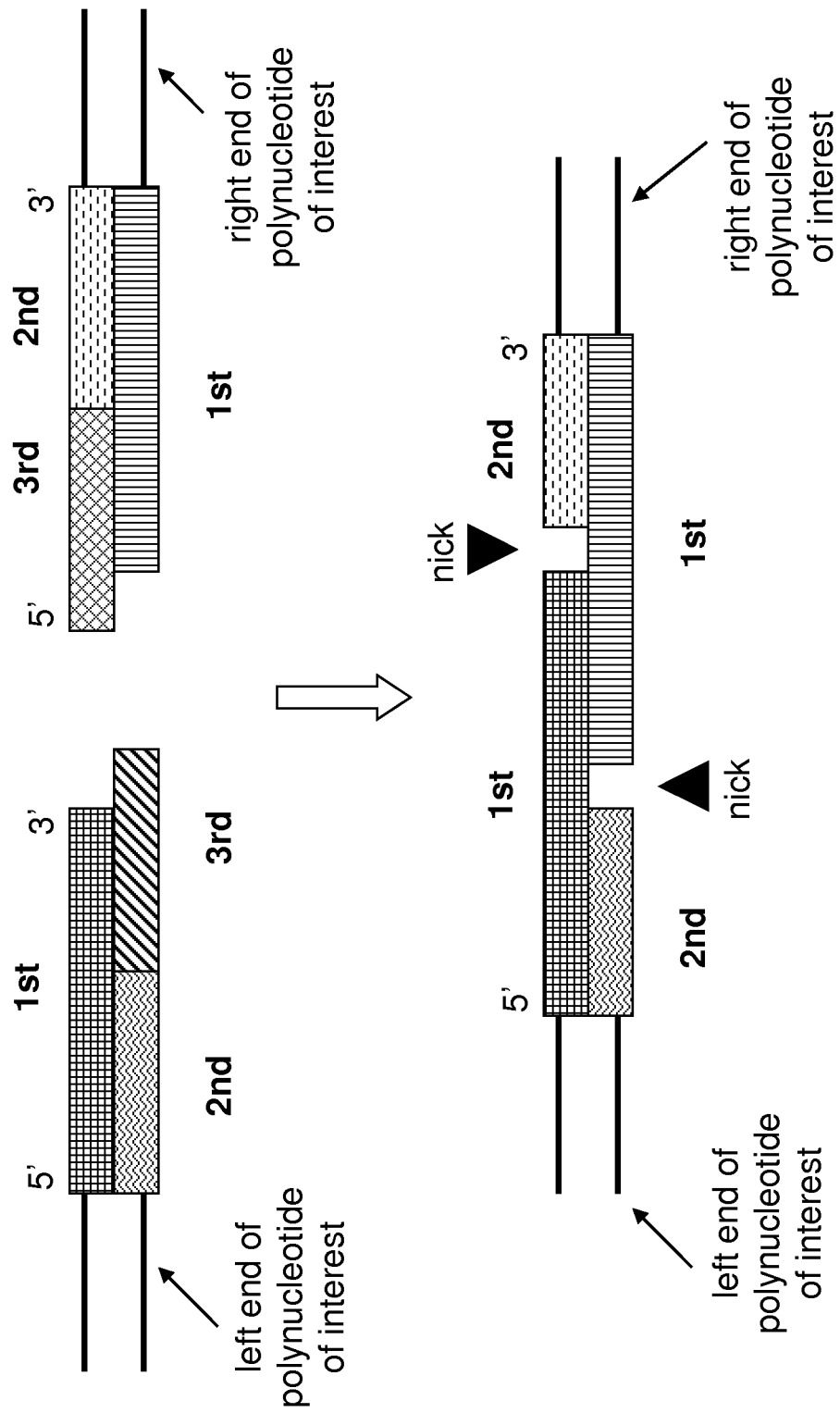

Provided herein are blocking oligonucleotide adaptors which can be used to join together different polynucleotides or for joining together the ends of one polynucleotide. Blocking oligonucleotide adaptors can each comprise: (i) a nucleic acid duplex comprising a first single-stranded oligonucleotide annealed to a second single-stranded oligonucleotide to form an overhang portion; and (ii) a third single-stranded oligonucleotide (a blocking oligonucleotide) that is annealed to the overhang portion (FIGS. 1A and B). An end of the nucleic acid duplex having the overhang portion can form an adaptor-joining end and the other end of the duplex can form a target-joining end. The blocking oligonucleotide (the third single-stranded oligonucleotide) can anneal to the overhang portion to interfere with and/or prevent hybridization between the overhang portions of the blocking oligonucleotide adaptors. Use of blocking oligonucleotide adaptors during a polynucleotide-joining step can reduce or prevent formation of dimers, trimers or other concatemerization of adaptors. Methods for joining together two or more polynucleotides, or for joining together two ends of a polynucleotide, can be practiced on any polynucleotide(s) including DNA, cDNA, RNA, RNA/DNA hybrids, and nucleic acid analogs.

Compositions, systems, methods and kits disclosed herein can be used to join together the ends of one or more polynucleotides. In some embodiments, a polynucleotide-joining step can be part of any recombinant DNA workflow, such as preparing nucleic acid libraries for any type of analysis, including mapping or sequencing. Nucleic acid sequencing techniques, platforms, and systems for which this disclosure is useful include, among others, sequencing-by-synthesis, chemical degradation sequencing (e.g., Maxam-Gilbert), ligation-based sequencing, hybridization sequencing, pyrophosphate detection sequencing, capillary electrophoresis, gel electrophoresis, next-generation, massively parallel sequencing platforms, semiconductor based sequencing platforms, sequencing platforms that detect hydrogen ions or other sequencing by-products, and single molecule sequencing platforms.

Many next-generation or massively parallel sequencing systems can involve the preparation of nucleic acid libraries, which often include steps for joining together two or more polynucleotides, or steps for joining the ends of one polynucleotide to form a circular molecule. For example, many next-generation sequencing systems prepare and analyze mate pair libraries. In some embodiments, a mate pair can include two tags (nucleic acid sequences) that originate from one nucleic acid fragment. A mate pair library can include a collection of mate pairs that can be used as sequencing templates. Typically, mate pair library workflows can include circularizing a linear nucleic acid and releasing a linear mate pair construct. Typically, the ends of the fragments that make up a mate pair library can be sequenced. Generally, the distance between the two ends, or other information regarding the two ends, is known. Sequence information from these ends can be aligned or mapped to a known genomic sequence for sequence assembly (Mullikin and Ning 2003 Genome Res. 13:81-90; Kent 2001 Genome Res. 11:1541-1548). Mate pair libraries are commonly used in genomic DNA physical mapping and sequencing strategies (Siegel 2000 Genomics 68:237-246; Roach 1995 Genomics 26:345-353). Other types of libraries used in or for next-generation sequencing include fragment libraries, RNA libraries (e.g., mRNA libraries, RNA-Seq libraries, whole transcriptome libraries, cell-specific RNA libraries), chromatin immunoprecipitation (ChIP) libraries, and methylated DNA libraries. Compositions, systems, methods, and kits disclosed herein can be useful for preparing nucleic acid libraries for use with any next-generation sequencing system, including: sequencing by oligonucleotide probe ligation and detection (e.g., SOLiD™ from Life Technologies, WO 2006/084131), probe-anchor ligation sequencing (e.g., Complete Genomics™ or Polonator™), sequencing-by-synthesis (e.g., Genetic Analyzer and HiSeq™, from Illumina), pyrophosphate sequencing (e.g., Genome Sequencer FLX from 454 Life Sciences), ion-sensitive sequencing (e.g., Personal Genome Machine from Ion Torrent™ Systems, Life Technologies), and single molecule sequencing platforms (e.g., HeliScope™ from Helicos).

Compositions, systems, methods and kits disclosed herein can be used in a workflow for constructing a nucleic acid library for sequencing in an oligonucleotide probe ligation and detection system (e.g., SOLiD™ from Life Technologies). Provided herein are blocking oligonucleotide adaptors which can be used to join together the ends of a polynucleotide to form a circular molecule. Blocking oligonucleotide adaptors can each comprise: (i) a first and second single-stranded oligonucleotide that are annealed together to form a nucleic acid duplex with an overhang portion; and (ii) a third single-stranded oligonucleotide (blocking oligonucleotide) that is annealed to the overhang portion. The end of the duplex structure having the overhang portion can form an adaptor-joining end and the other end of the duplex structure can form a target-joining end. Methods for preparing a SOLiD mate-pair library can generally include: (a) providing a linear polynucleotide of interest (e.g., a double-stranded polynucleotide) having a first and second end; (b) joining the first end of the linear polynucleotide of interest to a first oligonucleotide adaptor and joining the second end of the linear polynucleotide of interest to a second oligonucleotide adaptor so as to generate an adaptor-polynucleotide-adaptor product; and (c) circularizing the adaptor-polynucleotide-adaptor product. A circularizing step (c) can include removing the third single-stranded oligonucleotide (blocking oligonucleotide) from the overhang portions of the first and second oligonucleotide adaptors so as to expose the overhang portions of the adaptor-joining ends. The exposed overhang ends can be annealed together, thereby circularizing the adaptor-polynucleotide-adaptor product. An exposed overhang ends can hybridize to each other so as to leave a gap or nick on one or both strands at the junction between the adaptor-joining ends of the first and second adaptors. The nick(s) can be moved to a new position within the polynucleotide of interest. For example, the nick(s) can be moved to a new position by conducting a nick translation reaction on the nick. Conducting the nick translation reaction for a shorter or longer period of time can modulate the distance that the nick moves into the polynucleotide of interest. A strand opposite the new position of the nick can be cleaved with a single-strand specific endonuclease enzyme to release a linear mate pair construct having a pair of blocking oligonucleotide adaptors (minus the blocking oligonucleotide) flanked by two portions of the polynucleotide of interest (e.g., tags). The lengths of the tags can be modulated by increasing or decreasing the length of time of the nick translation reaction. The released linear mate pair construct can be joined to additional adaptors to permit amplification and/or sequencing. The mate pair constructs can be sequenced using SOLiD™ sequencing methods.

Compositions, systems, methods and kits disclosed herein can be used in a workflow for constructing a nucleic acid library for sequencing on a semiconductor based-sequencing platform. In some embodiments, compositions, systems, methods and kits disclosed herein can be used in a workflow for constructing a nucleic acid library for Ion Torrent™ Systems (Life Technologies). Provided herein are blocking oligonucleotide adaptors which can be used to join together the ends of a polynucleotide to form a circular molecule. Blocking oligonucleotide adaptors can each comprise: (i) a first and second single-stranded oligonucleotide that are annealed together to form a nucleic acid duplex with an overhang portion; and (ii) a third single-stranded oligonucleotide (blocking oligonucleotide) that is annealed to the overhang portion. The end of the duplex structure having the overhang portion can form an adaptor-joining end and the other end of the duplex structure can form a target-joining end. Methods for preparing a Ion Torrent™ mate-pair library can generally include: (a) providing a linear polynucleotide of interest (e.g., a double-stranded polynucleotide) having a first and second end; (b) joining the first end of the linear polynucleotide of interest to a first oligonucleotide adaptor and joining the second end of the linear polynucleotide of interest to a second oligonucleotide adaptor so as to generate an adaptor-polynucleotide-adaptor product; and (c) circularizing the adaptor-polynucleotide-adaptor product. A circularizing step (c) can include removing the third single-stranded oligonucleotide (blocking oligonucleotide) from the overhang portions of the first and second oligonucleotide adaptors so as to expose the overhang portions of the adaptor-joining ends. An exposed overhang ends can be annealed together, thereby circularizing the adaptor-polynucleotide-adaptor product. An exposed overhang ends can hybridize to each other so as to leave a gap or nick on one or both strands at the junction between the adaptor-joining ends of the first and second adaptors. A nick(s) can be moved to a new position within the polynucleotide of interest. For example, the nick(s) can be moved to a new position by conducting a nick translation reaction on the nick. Conducting a nick translation reaction for a shorter or longer period of time can modulate the distance that the nick moves into the polynucleotide of interest.

The strand opposite the new position of the nick can be cleaved with a single-strand specific endonuclease enzyme to release a linear mate pair construct having a pair of blocking oligonucleotide adaptors (minus the blocking oligonucleotide) flanked by two portions of the polynucleotide of interest (e.g., tags). The lengths of the tags can be modulated by increasing or decreasing the length of time of the nick translation reaction. The released linear mate pair construct can be joined to additional adaptors to permit amplification and/or sequencing. The mate pair constructs can be sequenced using Ion Torrent™ sequencing methods. For example, mate pair constructs can be clonally amplified on Ion Sphere™ Particles as part of the Ion Xpress™ Template Kit (Life Technologies Part No. 4469001) for use in downstream sequencing. Template preparation can be performed essentially accordingly to the protocols provided in the Ion Xpress™ Template Kit v2.0 User Guide (Life Technologies, Part No. 4469004). The amplified DNA can then be sequenced on an Ion PGM™ sequencer (Ion Torrent™, Life Technologies, Part No. 4462917) essentially according to the protocols provided in the Ion Sequencing Kit v2.0 User Guide (Ion Torrent™, Life Technologies, Part No. 4469714) and using the reagents provided in the Ion Sequencing Kit (Ion Torrent™, Life Technologies, Part No. 4468997) and the Ion 314™ Chip Kit (Ion Torrent™, Life Technologies, Part No. 4462923).

Provided herein are blocking oligonucleotide adaptors which can comprise a double-stranded oligonucleotide adaptor having: (i) a first and a second single-stranded oligonucleotide annealed together to form a duplex having an overhang portion and (ii) a third single-stranded oligonucleotide annealed to the overhang portion, wherein the end of the duplex having the overhang portion forms an adaptor-joining end and the other end of the duplex forms a target-joining end (FIGS. 1A and B). In some embodiments, the first single-stranded oligonucleotide can comprise a 5' phosphorylated terminal end. In some embodiments, the second single-stranded oligonucleotide can lack a 5' phosphorylated terminal end. In some embodiments, the third single-stranded oligonucleotide can lack a 5' phosphorylated terminal end. In some embodiments, the double-stranded oligonucleotide adaptor can comprise at least one biotin moiety.

Provided herein are a circularized polynucleotide of interest which can comprise: a linear polynucleotide of interest having a first end and a second end, wherein the first end can be joined to a target-joining end of a first double-stranded oligonucleotide adaptor and the second end can be joined to a target-joining end of a second double-stranded oligonucleotide adaptor, and having the third single-stranded oligonucleotides removed from the first and second double-stranded oligonucleotide adaptors so as to anneal together the overhang portions of the first and second double-stranded oligonucleotide adaptors thereby forming a circular polynucleotide of interest, wherein the first and second double-stranded oligonucleotide adaptors include (i) a first and a second single-stranded oligonucleotide annealed together to form a duplex having an overhang portion and (ii) a third single-stranded oligonucleotide annealed to the overhang portion, wherein the end of the duplex having the overhang portion forms a adaptor-joining end and the other end of the duplex forms a target-joining end, and wherein the overhang portion of the first and second double-stranded oligonucleotide adaptors are capable of annealing with each other (FIGS. 1A and B). In some embodiments, the first single-stranded oligonucleotide can comprise a 5' phosphorylated terminal end. In some embodiments, the second single-stranded oligonucleotide can lack a 5' phosphorylated terminal end. In some embodiments, the third single-stranded oligonucleotide can lack a 5' phosphorylated terminal end. In some embodiments, the double-stranded oligonucleotide adaptor can comprise a biotin moiety. In some embodiments, in the circularized polynucleotide of interest, the junctions between the annealed overhang portions of the first and the second double-stranded oligonucleotide adaptors include a gap or nick. In some embodiments, the linear polynucleotide of interest comprises a double-stranded nucleic acid.

Provided herein are methods for circularizing nucleic acids which can comprise: (a) providing a first and a second double-stranded oligonucleotide adaptor each having (i) a first and a second single-stranded oligonucleotide annealed together to form a duplex having an overhang portion and (ii) a third single-stranded oligonucleotide annealed to the overhang portion, wherein the overhang portion of the first and second double-stranded oligonucleotide adaptors are capable of annealing with each other, and wherein for the first and a second double-stranded oligonucleotide adaptors the end of the duplex having the overhang portion forms an adaptor-joining end and the other end of the duplex forms a target-joining end; (b) joining the target-joining end of the first double-stranded oligonucleotide adaptor to a first end of the linear double-stranded polynucleotide of interest; (c) joining the target-joining end of the second double-stranded oligonucleotide adaptor to a second end of the linear double-stranded polynucleotide of interest; (d) removing the third single-stranded oligonucleotide from the first and the second double-stranded oligonucleotide adaptors so as to expose the overhang portions of the adaptor-joining ends; and (e) annealing the overhang portions of the adaptor-joining ends thereby forming a circular polynucleotide of interest. In some embodiments, the junction between the adaptor-joining ends of the first and the second double-stranded oligonucleotide adaptors which are annealed together in step (e) can include at least one nick. In some embodiments, the method can further comprise the step: moving the at least one nick to a new position within the double-stranded polynucleotide of interest. In some embodiments, the moving the at least one nick to a new position within the double-stranded polynucleotide of interest can comprise performing a nick translation reaction on the at least one nick. In some embodiments, the nick translation reaction can be a coupled 5' to 3' DNA polymerization/degradation reaction, or can be a coupled 5' to 3' DNA polymerization/strand displacement reaction. In some embodiments, the method can further comprise the steps: (f) performing an exonuclease reaction to remove at least a portion of the strand having the nick so as to open the nick into a gap; and (g) cleaving the strand opposite the gap so as to release a linear mate pair construct.

Provided herein are blocking oligonucleotide adaptors that can be used as part of a workflow for joining together the two ends of a polynucleotide to form a circular molecule. In some embodiments, workflows can be used to prepare mate pair libraries for any next generation sequencing platform.

Provided herein are workflows for preparing a next generation sequencing library which can generally include: fragmenting, adaptor-joining, circularizing, and releasing a linear mate pair construct. For example, preparing a next generation mate pair library can include: (a) joining both ends of a polynucleotide of interest to a pair of blocking oligonucleotide adaptors; and (b) circularizing the polynucleotide of interest by removing the blocking oligonucleotide to permit hybridization of the overhang ends and to form at least one nick at the junction of the annealed overhang ends. In some embodiments, methods further comprise: (c) moving the at least one nick to a new position within the polynucleotide of interest; and (d) cleaving strand opposite the new position of the nick so as to release a linear mate pair construct. In some embodiments, released mate pair constructs can be joined to additional adaptors to form adaptor-mate pair constructs which can be compatible with any next generation sequencing platform. In some embodiments, additional adaptors can provide functionality for amplification, attachment to a surface and/or sequencing. In some embodiments, adaptor-mate pair constructs can be immobilized to a surface. In some embodiments, any reaction for preparing a next generation sequencing library can be conducted in a reaction vessel. In some embodiments, any reaction for preparing a next generation sequencing library can be conducted in a thermal-control apparatus.

For example, blocking oligonucleotide adaptors can generally include a nucleic acid duplex having an overhang end, and a third oligonucleotide (blocking oligonucleotide) can be annealed to the overhang end. One or both strands in the nucleic acid duplex can comprise at least one binding partner (e.g., biotin). The end of the duplex having the overhang end can form an adaptor-joining end and the other end of the duplex structure can form a target-joining end. In a pair of blocking oligonucleotide adaptors, the adaptor-joining ends can anneal with each other upon removal of the third polynucleotides (blocking oligonucleotides). A 5' terminal end of a target-joining end can be phosphorylated or can lack phosphorylation. A 5' terminal end of an adaptor-joining end can be phosphorylated or can lack phosphorylation.

In some embodiments, a polynucleotide of interest can be subjected to a nucleic acid workflow for nucleic acid library preparation that includes a fragmentation step followed by any combination and in any order any nucleic acid manipulation step, including: size selection, end repair, adaptor ligation or oligonucleotide ligation (e.g., blocking oligonucleotide adaptors, barcodes adaptors, or P1, P2, A or CAP adaptors), adaptor annealing, circularization, moving-a-nick, releasing a linear mate pair construct, nick translation, tailing, amplification, purification, removing linear nucleic acids, washing, quantization, immobilization, denaturation. In some embodiments, additional nucleic acid manipulation steps can include: exonuclease or endonuclease reactions. In some embodiments, any step or any combination of steps can be conducted by an automated system. For example, an automated system can include robotic delivery of reagents and/or computer-controlled reaction regimen (temperature and time). Any of these steps can be omitted or repeated. For example generating a mate pair library for a 3 kb insert can include: fragmenting the polynucleotide of interest, size-selection, end repair, adaptor ligation or oligonucleotide ligation, and circularization. In some embodiments, generating a mate pair library for a 10 kb insert can include: fragmenting the polynucleotide of interest, end repair, size-selection, adaptor ligation or oligonucleotide ligation, and circularization.

For example, a nucleic acid library preparation workflow can include the steps: fragmentation, size-selection; end repair; ligation to blocking oligonucleotide adaptors; circularization; nick translation; releasing linear mate pair constructs; tailing; ligation to sequencing adaptors; nick translation and amplification.

In another example, a nucleic acid library preparation workflow can include the steps: fragmentation, end repair; size-selection; ligation to blocking oligonucleotide adaptors; circularization; nick translation; releasing linear mate pair constructs; tailing; ligation to sequencing adaptors; nick translation and amplification.

In another example, a nucleic acid library preparation workflow can include the steps: fragmentation, end repair; size-selection; ligation to blocking oligonucleotide adaptors; circularization; nick translation; releasing linear mate pair constructs; end repair; ligation to sequencing adaptors; amplification; and size-selection.

In another example, a nucleic acid library preparation workflow can include the steps: fragmentation; end repair; size-selection; circularization (without circularization adaptor); fragmentation of circularized constructs; end repair; tailing; ligation to sequencing adaptors; amplification; size-selection; and immobilization.

In another example, a nucleic acid library preparation workflow can include the steps: fragmentation; end repair; ligation to circularization adaptors (e.g., loxP adaptors); size-selection; fill-in reaction; circularization (e.g., via Cre recombinase); fragmentation of circularized constructs; end repair; ligation to sequencing adaptors; amplification; size-selection; immobilization; and nucleic acid denaturation.

In some embodiments, a polynucleotide of interest can be isolated from any source including: an organism; normal or diseased cells or tissues; fresh or archived (e.g., formalin and/or paraffin) cell or tissue samples; chromosomal, genomic, organellar, methylated, cloned, amplified, DNA, cDNA, RNA, RNA/DNA or synthesized.

In some embodiments, a polynucleotide of interested can be fragmented by mechanical stress, enzymatic or chemical methods. Mechanical stress includes sonication, nebulization or cavitation. Enzymatic fragmentation includes any restriction endonuclease, nicking endonuclease or exonuclease. Chemical fragmentation includes dimethyl sulfate, hydrazine, NaCl, piperidine, or acid. In some embodiments, polynucleotides of interest can be fragmented to yield fragments that are about 3 kb or about 10 kb in length.

In some embodiments, fragmented polynucleotides of interest can be subjected to any size-selection procedure to obtain any desired size range. In some embodiments, nucleic acid size selection method includes without limitation: solid phase adherence or immobilization; electrophoresis, such as gel electrophoresis; and chromatography, such as HPLC and size exclusion chromatography. In some embodiments, size-selected fragments can include about 0.9-1.3 kb, or about 0.8-1.4 kb, or about 1.5-6 kb, or about, or about 2-5 kb, or about 2.8-3.5 kb, or about 6.5-9.5 kb, or about 10-11 kb, or about 17-25 kb. In some embodiments, fragmented polynucleotides of interest can be size selected from a 1% or a 0.6% agarose gel.

In some embodiments, the ends and/or internal portions of a fragmented polynucleotide of interest can be repaired to remove 5' and/or 3' overhang ends, or to phosphorylate an end or remove a terminal phosphate group. For example, an overhang end can be filled-in with a polymerase, such as a DNA polymerase (e.g., T4 DNA polymerase or Bst DNA polymerase) or a Klenow (e.g., large fragment and/or exonuclease minus). In some embodiments, an overhang end can be filled-in with natural nucleotides or analogs, including biotinylated nucleotides. In some embodiments, terminal 5' phosphate groups can be removed with a kinase enzyme. In some embodiments, an end repair reaction can include adding a phosphate to a 5' end and/or removing a phosphate from a 3' end. These reactions can be conducted with one or more enzymes that catalyze addition of a phosphate group to a 5' terminus of a single-stranded or double-stranded nucleic acid and/or that catalyze removal of 3' phosphoryl groups from a nucleic acid. In some embodiments, addition or removal of a phosphate group can be catalyzed by a polynucleotide kinase. A polynucleotide kinase can be a T4 polynucleotide kinase, or can be isolated from other sources (e.g., human). A polynucleotide kinase reaction can be conducted in the presence of ATP. In some embodiments, an end repair reaction resulting in a phosphate to a 5' end catalyzed by one or more enzymes can be terminated by a heat inactivation step.

In some embodiments, a polynucleotide of interest can have a first end and a second end. In some embodiments, a first end can be joined to the target-joining end of a first blocking oligonucleotide adaptor. In some embodiments, a second end can be joined to the target-joining end of a second blocking oligonucleotide adaptor. In some embodiments, one or more blocking oligonucleotide adaptors can be joined to a polynucleotide of interest enzymatically or by annealing. In some embodiments, adaptor-joining can be conducted with a ligase enzyme. In some embodiments, each end of a polynucleotide of interest can be joined to a separate blocking oligonucleotide adaptor to form an adaptor-polynucleotide-adaptor product.

In some embodiments, polynucleotides of interest can be subjected to any purification procedure to remove non-desirable materials. In some embodiments, purification procedures can include: bead purification, column purification, gel electrophoresis, dialysis, alcohol precipitation, and size-selective PEG precipitation. For example, a purification step can be conducted with solid phase adherence/immobilization paramagnetic beads (AMPure XP beads from Agencourt) or streptavidin paramagnetic beads (Dynabeads™ from Invitrogen). In another example, PureLink™ (Invitrogen) or Microcon™ (Millipore) columns or can be used for purification.

In some embodiments, an adaptor-polynucleotide-adaptor product can be circularized by removing the blocking oligonucleotides (third oligonucleotides) to permit annealing between the overhang ends (adaptor-joining ends) of the two adaptors thereby circularizing the adaptor-polynucleotide-adaptor product. In some embodiments, a blocking oligonucleotide (e.g., third oligonucleotide) can be separated (denatured) from an overhang portion by heat denaturation and/or modulating the salt and/or sodium and/or formamide concentration(s). In some embodiments, a blocking oligonucleotide can be removed, and a first and a second overhang end can anneal with each other at about 30° C., or about 50-80° C. or about 70° C. In some embodiments, a polynucleotide of interest can undergo intramolecular circularization (via ligation or annealing) without joining to a circularization adaptor (e.g., self-circularization). Circularization (without a circularization adaptor) can be achieved with a ligase at about 4-35° C. In some embodiments, a polynucleotide of interest can be joined to a loxP adaptor and circularization can be mediated by a Cre recombinase enzyme reaction. Circularization with Cre recombinase can be achieved at about 4-35° C.

In some embodiments, in a circularized construct, the junctions between the annealed overhang ends can include at least one nick or gap. Nicks or gaps can serve as an initiation site for an enzymatic reaction to move the position of the nick or gap to a new position.

In some embodiments, the position of the nick or gap at the junction between the annealed overhang ends can be moved to a new position within the polynucleotide of interest. For example, a nick translation reaction can be conducted for a period of time to move the position of the nick to a new position within the polynucleotide of interest. The nick translation reaction can be stopped at a desired time. The length of time for conducting the nick translation reaction can provide size-tunable tags in the released mate pair construct. In some embodiments, a nick translation reaction can be conducted with an enzyme that couples a 5'→3' polymerization/degradation reaction, such as *E. coli* DNA polymerase I or Bst DNA polymerase.

In some embodiments, after conducting a nick translation reaction, a linear mate pair construct can be released from a circular molecule by cleaving the strand opposite the new position of the nick. A cleaving step can be conducted with an enzyme or chemical compound. For example, cleavage can be conducted with one or more endonucleases and/or exonucleases together or serially. In some embodiments, releasing a linear mate pair construct can include the steps: enzymatically opening/widening the nick (at the new position) and cleaving the strand opposite the widened nick site. In some embodiments, a T7 exonuclease can be used to widen the nick, and an S1 nuclease can be used to cleave the strand opposite the nick. In some embodiments, a released linear mate pair construct can include a pair of blocking oligonucleotide adaptors (joined together) flanked on both sides by paired polynucleotide sequences of interest (e.g., left and right paired tags). In some embodiments the polynucleotide sequence of interest (e.g., left or right paired tag) can be about 25 to about 1000 base pairs, about 25 to about 500 base pairs, about 25 to about 300 base pairs, about 50 to about 200 base pairs, or about 50 to about 100 base pairs in length.

In some embodiments, a non-template-dependent terminal transferase reaction can be conducted for a tailing step. In some embodiments, a non-template-dependent terminal transferase reaction can be catalyzed by a Taq polymerase, Tfi DNA polymerase, 3' exonuclease minus-large (Klenow) fragment, or 3' exonuclease minus-T4 polymerase.

In some embodiments, one or both ends of a released mate pair construct can be joined to at least one additional adaptor. Such additional adaptors can include functionalities for further nucleic acid manipulations such as amplification, immobilization, sequencing and/or unique identification. In some embodiments, each end of a released mate pair construct can be joined to the same or different additional adaptors. In some embodiments, a released mate pair construct can be joined to at least one additional adaptor with a ligase enzyme or by hybridization. In some embodiments, additional adaptors can have any structure, including linear, hairpin, forked, or stem-loop. A released mate pair construct can be joined to an adaptor to permit attachment to a particle (e.g., bead) or to a surface. For example, an adaptor can include a nucleotide sequence that is complementary to an oligonucleotide capture primer that is attached to a particle or surface. An immobilized oligonucleotide capture primer can anneal to an immobilization adaptor that is joined to a released mate pair construct, and a primer extension reaction can be conducted to generate a complementary copy of the released mate pair construct attached to a surface. In some embodiments, a bridge amplification reaction can be conducted by joining a released mate pair construct to different adaptors at each end (where the adaptors are complementary to different oligonucleotide capture primers that are attached to a surface) and conducting multiple primer extension reactions. In some embodiments, attachment of a released mate pair construct to a particle or surface can be achieved by conducting a primer extension reaction or an amplification reaction in an aqueous condition. Primer extension and amplification reactions can be conducted under isothermal or thermocyclic conditions, or can be reacted in a tube, a well, an oil-and-water emulsion droplet or an agarose droplet (Yang 2010 Lab Chip 10(21):2841-2843).

In some embodiments, a released mate pair construct can be amplified using at least one type of polymerase, nucleotides (natural or analogs thereof), and one or more amplification primers (e.g., forward and/or reverse primers). In some embodiments, the linear mate pair can be amplified by emulsion polymerase chain reaction (EmPCR). In some embodiments, multiple amplification cycles can be conducted. For example, a limited number of amplification cycles can be conducted (e.g., 10-14, 12-16, 16-20 or 20 cycles or more), or amplification can be conducted until product plateau is achieved. In some embodiments, amplification can be conducted with a thermostable or thermolabile polymerase. In some embodiments, amplification can be conducted with a polymerase having proofreading capability. In some embodiments, amplification can be conducted with a Taq polymerase, Phusion™ polymerase (Finnzyme, Finland), a GC-rich DNA polymerase such as one isolated from *Pyrolobus fumarius* (e.g., AccuPrime™ from Invitrogen, Carlsbad, Calif.), or a blend of different DNA polymerases for amplifying GC-rich sequences (e.g., GC-rich PCR system from Roche).

In some embodiments, one or both ends of a released mate pair construct can be modified for attachment to a surface or particle. For example, a 5' or 3' end can be modified to include an amino group that can bind to a carboxylic acid compound on a surface or a particle. A 5' end can include a phosphate group for reacting with an amine-coated surface (or particle) in the presence of a carbodiimide (e.g., water soluble carbodiimide). A nucleic acid can be biotinylated at one end to bind with an avidin-like compound (e.g. streptavidin) attached to a surface.

In some embodiments, a surface can be planar, convex, concave, or any combination thereof. A surface can be porous, semi-porous or non-porous. A surface can comprise an inorganic material, natural polymers, synthetic polymers, or non-polymeric material. A surface includes a flowcell, well, groove, channel, reservoir, filter, gel or inner walls of a capillary. A surface can be coated with an acrylamide compound. A mate pair construct can be immobilized to an acrylamide compound coating on a surface.

In some embodiments, a mate pair construct can be attached to a particle. In some embodiments, a particle can have a shape that is spherical, hemispherical, cylindrical, barrel-shaped, toroidal, rod-like, disc-like, conical, triangular, cubical, polygonal, tubular, wire-like or irregular. A particle can have an iron core or comprise a hydrogel or agarose (e.g., Sepharose™). A particle can be paramagnetic. A particle can be spherical or irregular shape. A particle can have cavitation or pores, or can include three-dimensional scaffolds. A particle can be coated with a carboxylic acid compound or an amine compound for attaching nucleic acid fragments. A particle can be coated with an avidin-like compound (e.g., streptavidin) for binding biotinylated nucleic acid fragments. Particles can be deposited to a surface of a sequencing instrument. Sequencing reagents can be delivered to the deposited particles to conduct sequencing reactions. In some embodiments, a mate pair construct can be attached or immobilized to Ion Sphere™ Particles (sold as a component of the Ion Xpress Template Kit (Part No. 4469001)) for clonal amplification and use in downstream sequencing Immobilization to Ion Sphere™ Particles can be performed essentially according to the protocols provided in the Ion Xpress™ Template Kit v2.0 User Guide (Part No.: 4469004)).

In some embodiments, any step for preparing a next generation library can be conducted in any type of reaction vessel. For example, a reaction vessel includes any type of tube, column or well (e.g., 96-well plate).

In some embodiments, any step for preparing a next generation library (e.g., a mate pair library) can be practiced in any type of thermal-control apparatus. In some embodiments, a thermal-control apparatus can maintain a desired temperature, or can elevate and decrease the temperature, or can elevate and decrease the temperature for multiple cycles. In some embodiments, a thermal-control apparatus can maintain a temperature range of about 0° C.-100° C., or can cycle between different temperature ranges of about 0° C.-100° C. Examples of thermal-control apparatus include: a water bath and thermal cycler machine. Many thermal cycler machines are commercially-available, including (but not limited to) Applied Biosystems, Agilent, Eppendorf, Bio-Rad and Bibby Scientific.

Blocking Oligonucleotide Adaptors

Provided herein are blocking oligonucleotide adaptors for joining together the ends of one or more polynucleotides. A joining step can include joining together two or more different polynucleotides together, or joining together two ends of one polynucleotide to form a circular molecule. Blocking oligonucleotide adaptors can be used in a recombinant nucleic acid workflow to reduce the formation of adaptor dimers or trimers (or higher-order concatemers) which can improve the yield of desirable polynucleotide-adaptor products.

In some embodiments, a blocking oligonucleotide adaptor can comprise one or more single-stranded oligonucleotides (e.g., a first and second single-stranded oligonucleotide) which can anneal to each other to form a duplex structure having an overhang portion. The duplex structure can have a 5' or 3' overhang portion (FIGS. 1A and B). A third single-stranded oligonucleotide (or a single-stranded portion of an oligonucleotide) can anneal to the overhang portion. In some embodiments, the end of the duplex structure having the overhang portion can form an adaptor-joining end and the other end of the duplex structure can form a target-joining end (FIGS. 1-5). The term "oligonucleotide", refers to polydeoxyribonucleotides (containing 2-deoxy-D-ribose), to polyribonucleotides (containing D-ribose) and to any polynucleotide, which can be a ribo sugar-phosphate backbone consisting of an N-glycoside of a purine or pyrimidine base, or modified purine or pyrimidine base. There is no intended distinction between the length of a "nucleic acid", "polynucleotide" or an "oligonucleotide".

In some embodiments, a first and/or second single-stranded oligonucleotide can include a binding partner moiety (e.g., biotin). In some embodiments, the first single-stranded oligonucleotide can comprise a 5' phosphorylated terminal end. In some embodiments, the second single-stranded oligonucleotide can lack a 5' phosphorylated terminal end. In some embodiments, the third single-stranded oligonucleotide can lack a 5' phosphorylated terminal end.

In some embodiments, a blocking oligonucleotide adaptor can comprise (i) a first single-stranded oligonucleotide annealed to a second single-stranded oligonucleotide to form a duplex having an overhang portion and (ii) a third single-stranded oligonucleotide (blocking oligonucleotide) annealed to the overhang portion, where the end of the duplex having the overhang portion forms a adaptor-joining end and the other end of the duplex forms a target-joining end. The overhang portion can be exposed by removal of the third single-stranded oligonucleotide. An exposed overhang portion of a first blocking oligonucleotide adaptor can anneal to an exposed overhang portion of a second blocking oligonucleotide adaptor thereby joining the two adaptors together (FIGS. 1-5). In some embodiments, a first and/or second single-stranded oligonucleotide can include a binding partner moiety (e.g., biotin).

Linear and Circular Polynucleotide Constructs

Provided herein are linear polynucleotide constructs, comprising a linear polynucleotide of interest joined at one or both ends with a blocking oligonucleotide adaptor.

For example, a polynucleotide of interest having a first end and a second end can be joined at the first end to a target-joining end of a first blocking oligonucleotide adaptor. In some embodiments, a polynucleotide of interest (which is joined to a first blocking oligonucleotide adaptor) can further include a second end joined to a target-joining end of a second blocking oligonucleotide adaptor. In some embodiments, a linear construct comprises a polynucleotide of interest flanked on one or both sides with a blocking oligonucleotide adaptor.

In some embodiments, the overhang portion of the first and second blocking oligonucleotide adaptors are capable of annealing with each other. In some embodiments, the third single-stranded oligonucleotide (blocking oligonucleotide) of the first and second blocking oligonucleotide adaptors can be removed to expose the overhang portions. In some embodiments, the overhang portions of the first and second blocking oligonucleotide adaptors can anneal with each other thereby joining together the first and second adaptors (at their adaptor-joining ends) so as to circularize the polynucleotide of interest. In some embodiments, one or both polynucleotide strands at the junction between the adaptor-joining ends of the first and second adaptors can include a nick or gap.

Embodiments of Blocking Oligonucleotide Adaptors

Figure 1B:
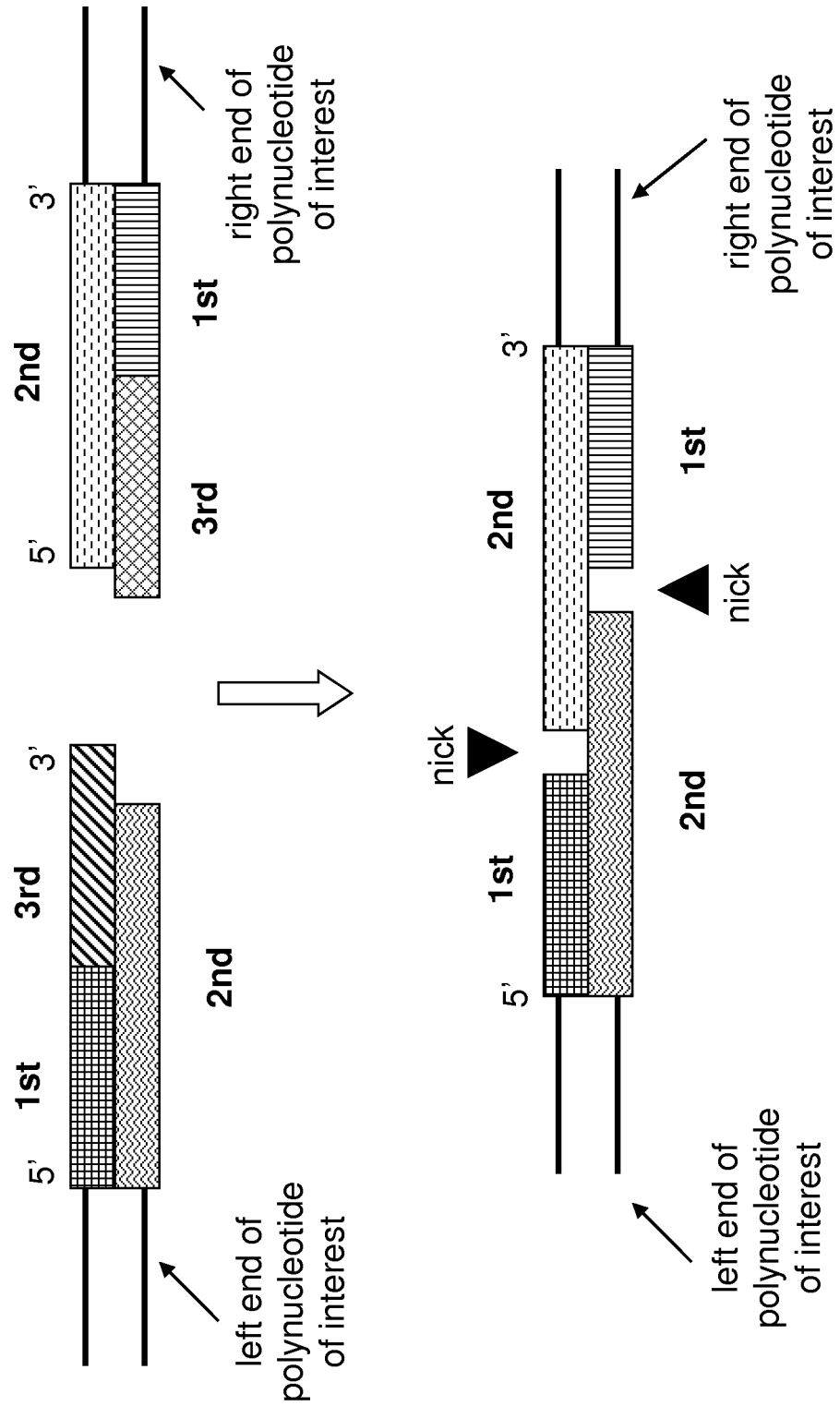
Figure 2:
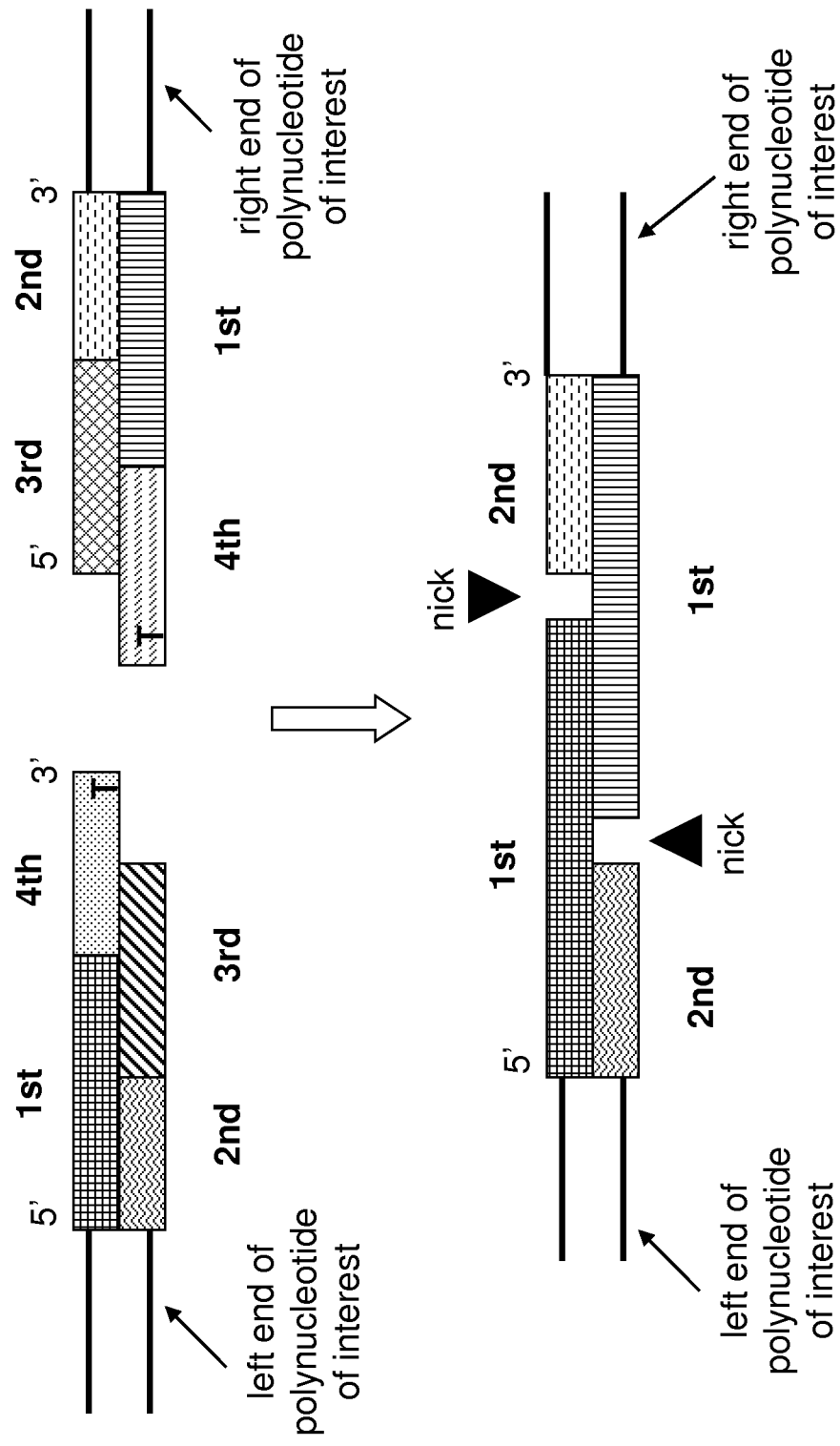

In some embodiments, blocking oligonucleotide adaptors comprise at least one single-stranded oligonucleotide(s) (strand(s)) (FIGS. 1 and 2). For example, a first and a second single-stranded oligonucleotide can anneal to each other to form a double-stranded adaptor (a duplex) having a 3' or 5' overhang portion. A third single-stranded oligonucleotide can anneal to an overhang portion. The third oligonucleotide can be a blocking oligonucleotide. One end of the double-stranded adaptor can be a target-joining end that can be joined to the polynucleotide of interest. The other end of the double-stranded adaptor can be an adaptor-joining end that can be joined to another adaptor (e.g., another blocking oligonucleotide adaptor) (FIGS. 1 and 2).

In some embodiments, a blocking oligonucleotide adaptor can have more than one blocking oligonucleotide. For example, a third single-stranded oligonucleotide can be a first blocking oligonucleotide that anneals to an overhang portion. A third single-stranded oligonucleotide can form an overhang portion. A fourth single-stranded oligonucleotide can be a second blocking oligonucleotide that can anneal to an overhang formed by the third single-stranded oligonucleotide (FIG. 2). In some embodiments, a fourth single-stranded oligonucleotide can form an overhang portion. It will become readily apparent to the skilled artisan that multiple blocking oligonucleotides can be formed from additional single-stranded oligonucleotides. Thus, the overhang portion(s) can be formed by the first or second single-stranded oligonucleotide or can be formed by any of the blocking oligonucleotides. A blocking oligonucleotide (e.g., third or fourth single-stranded oligonucleotide) can interfere with and/or prevent undesirable hybridization of the overhang portion to another nucleic acid, such as an overhang portion from another blocking oligonucleotide adaptor or a polynucleotide of interest.

In some embodiments, a first portion of the first single-stranded oligonucleotide can anneal with a second single-stranded oligonucleotide, and a second portion of the first single-stranded oligonucleotide can form a hairpin structure which can block hybridization of the first single-stranded oligonucleotide with another nucleic acid (FIG. 6A). In some embodiments, a portion of the third (or fourth) single-stranded oligonucleotide can form a hairpin structure which can block hybridization of the third (or fourth) single-stranded oligonucleotide with another nucleic acid (FIG. 6B).

In some embodiments, the blocking oligonucleotide adaptors can be prepared by annealing together a first and second single-stranded oligonucleotide under conditions suitable for nucleic acid hybridization to form a nucleic acid duplex having an overhang portion. In some embodiments, the overhang portion of the nucleic acid duplex can be annealed with a third single-stranded oligonucleotide under conditions suitable for nucleic acid hybridization to form a blocking oligonucleotide adaptor (FIGS. 1 and 2, left or right adaptors).

In some embodiments, the first, second, third, fourth (and other) single-stranded oligonucleotides can hybridize (e.g., anneal) under conditions suitable for increasing or decreasing the stability of the annealed oligonucleotides. Such conditions can include salts (e.g., sodium), temperature, pH, buffers, formamide, and the like.

In some embodiments, the blocking oligonucleotide adaptors, comprising the first, second, third, and optionally fourth (or more) single-stranded oligonucleotides, can be pre-assembled (annealed or hybridized) prior to joining to the polynucleotide of interest.

In some embodiments, a duplex formed by annealing a first and second single-stranded oligonucleotide can be joined to a polynucleotide of interest, and a blocking oligonucleotide can be annealed to an overhang portion after the joining step.

In some embodiments, the first and/or second single-stranded oligonucleotides and/or any of the blocking oligonucleotides can include deoxyribonucleotides (e.g., DNA) or ribonucleotides (e.g., RNA) or can be a DNA/RNA hybrid.

In some embodiments, first and/or second single-stranded oligonucleotides and/or any of the blocking oligonucleotides can be any length, including about 2-25 bases, or about 25-50 bases, or about 50-75 bases, or about 75-100 bases, or about 100-150 bases, or about 150-200 bases, or longer. In some embodiments, first and/or second single-stranded oligonucleotides and/or any of the blocking oligonucleotides can about 0.2-1 kb, or about 1-100 kb, or about 0.1-100 mega bases, or longer.

In some embodiments, any of the overhang portions formed by the first or second single-stranded oligonucleotide or formed by any of the blocking oligonucleotides can be any length, such as for example, about 1-20 bases, or about 20-40 bases, or about 40-60 bases, or about 60-80 bases, or about 80-100 bases, or about 100-200 bases, or longer. In some embodiments, any of the overhang portions can about 0.2-1 kb, or about 1-100 kb, or about 0.1-100 mega bases, or longer.

In some embodiments, the blocking oligonucleotide can be the same length, or shorter or longer than the overhang portion to which it anneals. In some embodiments, the blocking oligonucleotide can having same number of bases, or fewer or more bases compared to the overhang portion to which it anneals.

In some embodiments, the first and/or second single-stranded oligonucleotides and/or any of the blocking oligonucleotides can have any nucleotide sequence. For example, the sequence can be monomeric (e.g., TTTT or GGGG), polymeric, palindrome, non-palindrome, repetitive, or any other type of sequence.

In some embodiments, the first and/or second single-stranded oligonucleotides and/or any of the blocking oligonucleotides can include natural or analogs of nucleosides: adenosine, thymidine, cytosine, guanine, uridine or inosine (or analogs thereof).

In some embodiments, the members of a pair of blocking oligonucleotide adaptors (e.g., left and right adaptors), can have the same or different sequences.

In some embodiments, the first and/or second single-stranded oligonucleotides and/or any of the blocking oligonucleotides can have any percent GC content.

In some embodiments, the portion of the first and second single-stranded oligonucleotides that anneal to each other can be partially or wholly complementary to each other.

In some embodiments, the overhang portion and the blocking oligonucleotide that anneals to the overhang portion can be partially or wholly complementary to each other.

A nucleic acid strand that is "complementary" refers to a nucleic acid sequence-strand or a peptide nucleic acid sequence strand which when aligned with the nucleic acid sequence of one strand of the target nucleic acid, such that the 5' end of the sequence is paired with the 3' end of the other sequence in antiparallel association, a stable duplex is formed. Complementarity need not be perfect. Stable duplexes can be formed that include mismatched nucleotides. Complementary nucleic acid strands need not hybridize with each other across their entire length.

In some embodiments, a blocking oligonucleotide can be hybridized to an overhang portion and then separated (e.g., denatured) from the overhang portion. For example, a blocking oligonucleotide can be denatured from an overhang portion under conditions that are suitable for decreasing the stability of the annealed oligonucleotides thereby causing partial or complete denaturation. Parameters for decreasing the stability of hybridized nucleic acids can be predicted from the length, % GC content, and/or degree of complementarity of the nucleic acid(s) to be hybridized or denatured. In some embodiments, thermal melting temperature ($T_m$) for nucleic acids can be a temperature at which half of the nucleic acid strands are double-stranded and half are single-stranded under a defined condition. In some embodiments, a defined condition can include ionic strength and pH in an aqueous reaction condition. A defined condition can be modulated by altering the concentration of salts (e.g., sodium), temperature, pH, buffers, and/or formamide. Typically, the calculated thermal melting temperature can be considered to be a very stringent hybridization condition under which the nucleic acids remain hybridized. A less stringent hybridization condition can be at about 5-30° C. below the $T_m$, or about 5-25° C. below the $T_m$, or about 5-20° C. below the $T_m$, or about 5-15° C. below the $T_m$, or about 5-10° C. below the $T_m$. Methods for calculating a $T_m$ are well known and can be found in Sambrook (1989 in "Molecular Cloning: A Laboratory Manual", $2^{nd}$ edition, volumes 1-3). Other sources for calculating a $T_m$ for hybridizing or denaturing nucleic acids include OligoAnalyze (from Integrated DNA Technologies) and Primer3 (distributed by the Whitehead Institute for Biomedical Research). In some embodiments, two nucleic acids can denature from each other (e.g., blocking oligonucleotide and overhang portion) at about 35-40° C., or about 40-45° C., or about 45-50° C., or about 50-55° C., or about 55-60° C., or about 60-65° C., or about 65-70° C., or about 70-75° C., or about 75-80° C., or about 80-85° C., or 85-90° C., or higher temperature ranges.

In some embodiments, a duplex having first oligonucleotide hybridized to a second oligonucleotide can be more stable (e.g., have a higher melting point) compared to a duplex having an overhang hybridized to a blocking oligonucleotide. In some embodiments, in a first blocking oligonucleotide adaptor, a first duplex comprises a first oligonucleotide hybridized to a second oligonucleotide, where one end of the first oligonucleotide extends beyond the area of hybridization to form a first overhang. In some embodiments, in a second blocking oligonucleotide adaptor, a second duplex comprises a third oligonucleotide hybridized to a fourth oligonucleotide, where one end of the third oligonucleotide extends beyond the area of hybridization to form a second overhang. In some embodiments, a first blocking oligonucleotide can be hybridized to the first overhang to form a third duplex. In some embodiments, a second blocking oligonucleotide can be hybridized to the second overhang to form a fourth duplex. In some embodiments, the melting points of the first and second duplexes can be greater than (e.g., a range of slightly through substantially greater than) the melting points of the third and fourth duplexes. In some embodiments, conditions used to denature (separate) the first and second blocking oligonucleotides from their respective overhangs does not destabilized hybridization (or does not substantially destabilize hybridization) between the first and second oligonucleotides or between the third and fourth oligonucleotides.

In some embodiments, the first and/or second single-stranded oligonucleotides and/or any of the blocking oligonucleotides can include natural nucleotides and/or nucleotide analogs. For example, first and/or second single-stranded oligonucleotides and/or any of the blocking oligonucleotides can include an nucleotide analog that can increase or decrease the stability of the annealed first, second, third or fourth single-stranded oligonucleotides (other additional single-stranded oligonucleotides) using any combination of PNA, L-DNA, LNA (locked nucleic acids), iso-C/iso-G, L-RNA, and/or O-methyl RNA.

In some embodiments, the 5' end of the first or second single-stranded oligonucleotide includes or lacks a terminal phosphate group.

In some embodiments, the 3' end of the first or second single-stranded oligonucleotide includes or lacks a nucleoside tail of one or more nucleosides (e.g., a tail comprising A, G, C, T, U and/or I).

Figure 3:
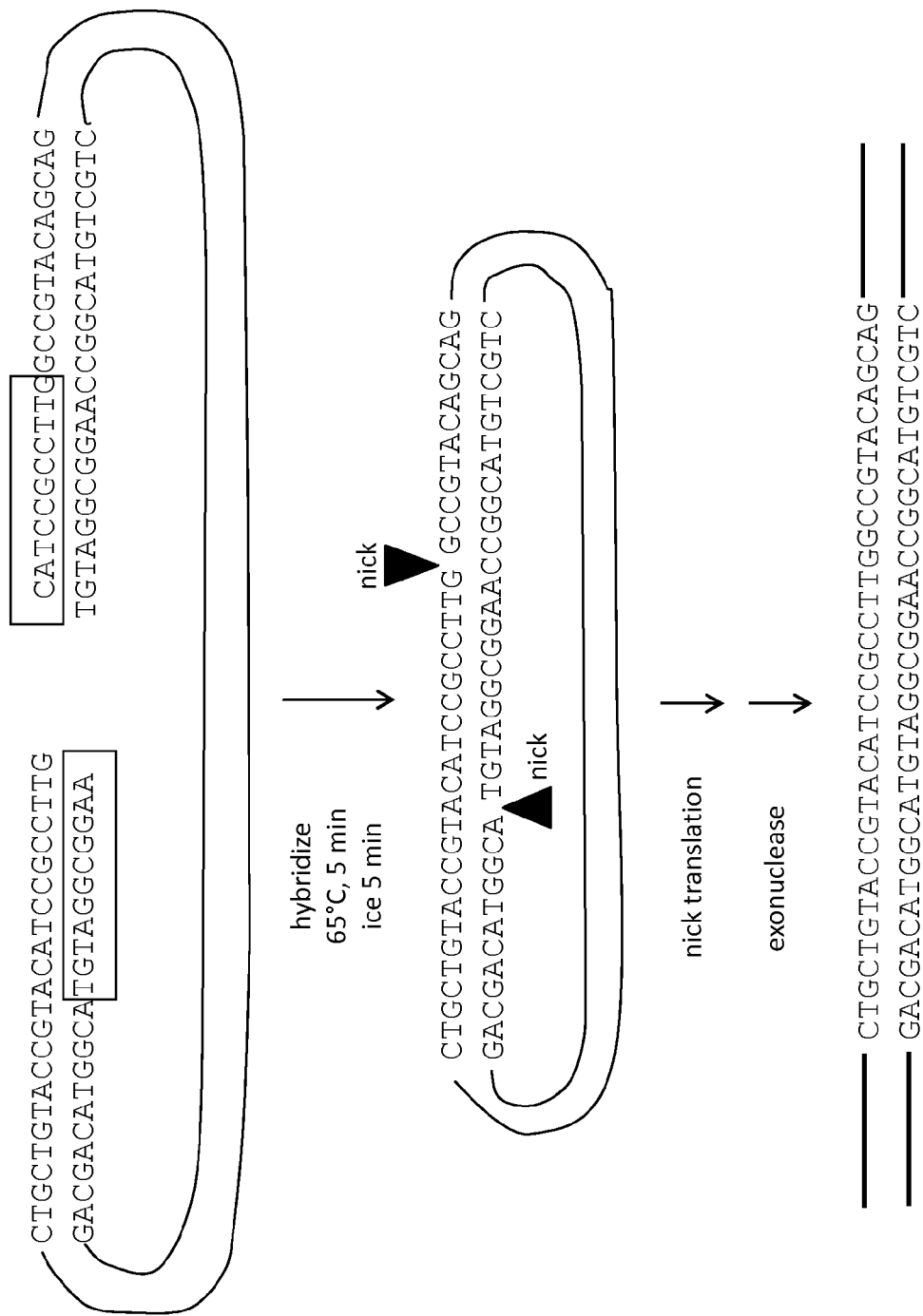
FIG. 3 is a schematic showing a non-limiting example of a nucleotide sequence of a left and right blocking oligonucleotide adaptor, and a method for circularizing a polynucleotide of interest which includes moving nicks to a new position on the circular molecule with a nick translation reaction, and releasing a linear mate pair construct with exonuclease.

In some embodiments, a nick can be located at or near the overhang portions that are annealed together (FIGS. 1-3). In some embodiments, the number and location of the nick(s) can be adjusted by varying the length and/or number of the overhang portions and/or by varying the length and/or number of blocking oligonucleotides. In some embodiments, a nick can be located on different strands. In some embodiments, a first or second single-stranded oligonucleotide can include at least one nick.

In some embodiments, the target-joining end can have a blunt end, a 3' overhang end, or a 5' overhang end.

Figure 4:
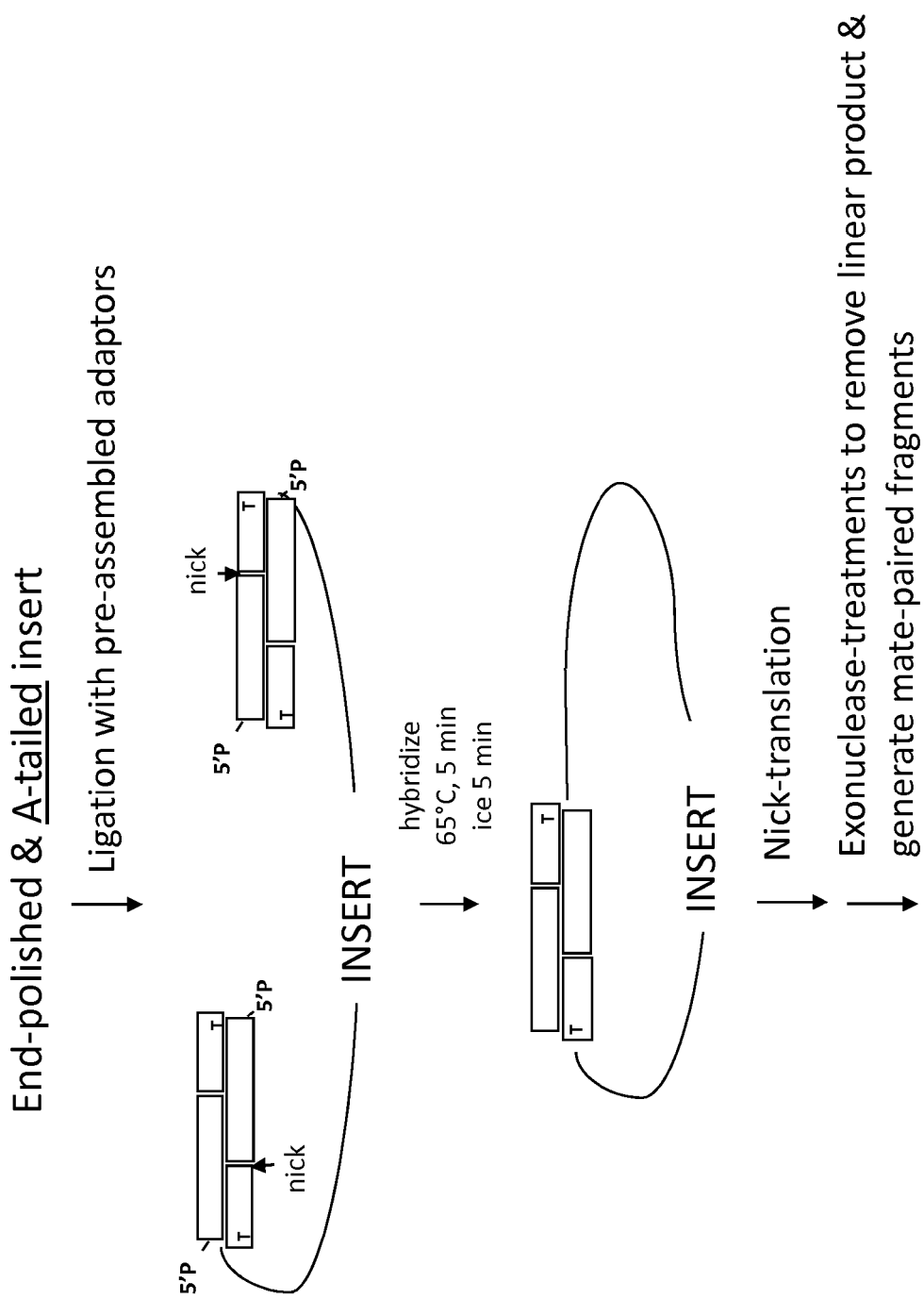
FIG. 4 is a schematic showing a non-limiting example of a method for circularizing a polynucleotide of interest using a pair of blocking oligonucleotide adaptors and releasing a mate pair construct.

In some embodiments, an adaptor-joining end can include a feature that reduces adaptor annealing. For example, in a pair of blocking oligonucleotide adaptors, an adaptor-joining end can include one or more terminal non-complementary bases (e.g., terminal T shown in FIGS. 2 and 4). In some embodiments, a 5' end of the third single-stranded oligonucleotide or a 3' end of the fourth single-stranded oligonucleotide can include terminal non-complementary base(s) (FIGS. 2 and 4). In some embodiments, a 5' end of the second oligonucleotide can include or lack a terminal 5' phosphate group (FIGS. 1-5). One skilled in the art will readily recognize that other embodiments are possible for blocking oligonucleotide adaptors having single-stranded oligonucleotides forming a 5' overhang end.

In some embodiments, a blocking oligonucleotide adaptor can include one or more barcode sequence. For example, any of the oligonucleotides that make up the blocking oligonucleotide adaptors can include one or more barcode sequences (FIG. 7). In some embodiments, a blocking oligonucleotide adaptor can be joined to one or more barcoded nucleic acid (e.g., barcoded adaptor). A barcode sequence can be a unique identifying sequence. A barcode sequence can be used for identifying, sorting, tracking, capture or multiplex reactions.

In some embodiments, any of the oligonucleotides that make up the blocking oligonucleotide adaptors can include one or more primer sequences for amplification or sequencing.

In one example, a pair of blocking oligonucleotide adaptors (left and right) each comprises a first, second and third single-stranded oligonucleotide having an overhang portion that is 12 nucleotides in length. The annealed adaptor-joining ends of left and right adaptors can have two nicks, with one nick on opposite strands (e.g., see FIGS. 1A and B).

In some embodiments, the left and right adaptors can comprise the following sequences:

```
Left adaptor 1:
1st strand: (24-mer)
                                         (SEQ ID NO: 1)
5'-CTGCTGTACCGTACATCCGCCTTG-3'

2nd strand: (12-mer)
                                         (SEQ ID NO: 2)
3'-GACGACATGGCA-5'

3rd strand: (11-mer)
                                         (SEQ ID NO: 3)
3'-TGTAGGCGGAA-5'

Right adaptor 1:
3rd strand: (11-mer)
                                         (SEQ ID NO: 4)
5'-CATCCGCCTTG-3'

2nd strand: (12-mer)
                                         (SEQ ID NO: 5)
5'-GCCGTACAGCAG-3'

1st strand: (24-mer)
                                         (SEQ ID NO: 6)
3'-TGTAGGCGGAACCGGCATGTCGTC-5'
```

Annealed right and left adaptors (strands 1 and 2):

```
                        ▼(nick)
                                         (SEQ ID NO: 7)
5'-CTGCTGTACCGTACATCCGCCTTG GCCGTACAGCAG-3'

(SEQ ID NO: 8)
3'-GACGACATGGCA TGTAGGCGGAACCGGCATGTCGTC-5'
             ▲(nick)
```

In some embodiments, a pair of a left adaptor 1 and a right adaptor 1 can be annealed together to form a first strand having a sequence:

```
                                         (SEQ ID NO: 9)
5'-CTGCTGTACCGTACATCCGCCTTGGCCGTACAGCAG-3'
```

In some embodiments, a pair of a left adaptor 1 and a right adaptor 1 can be annealed together to form a second strand having a sequence:

```
                                         (SEQ ID NO: 10)
3'-GACGACATGGCATGTAGGCGGAACCGGCATGTCGTC-5'

Left adaptor 2:
3rd strand: (12-mer)
                                         (SEQ ID NO: 11)
5'-ACATCCGCCTTG-3'

2nd strand: (9-mer)
                                         (SEQ ID NO: 12)
5'-GTACAGCAG-3'
```

```
1st strand: (24-mer)
                                         (SEQ ID NO: 13)
3'-GCATGTAGGCGGAACCGGCATGTCGTC-5'

Right adaptor 2:
1st strand: (27-mer)
                                         (SEQ ID NO: 14)
5'-CTGCTGTACCGTACATCCGCCTTGGCC-3'

2nd strand: (9-mer)
                                         (SEQ ID NO: 15)
3'-GACGACATG-5'

3rd strand: (12-mer)
                                         (SEQ ID NO: 16)
3'-TGTAGGCGGAAC-5'
```

In some embodiments, a pair of a left adaptor 2 and a right adaptor 2 can be annealed together to form a first strand having a sequence:

```
                                         (SEQ ID NO: 17)
5'-CTGCTGTACCGTACATCCGCCTTGGCCGTACAGCAG-3'
```

In some embodiments, a pair of a left adaptor 2 and a right adaptor 2 can be annealed together to form a second strand having a sequence:

```
                                         (SEQ ID NO: 18)
3'-GACGACATGGCATGTAGGCGGAACCGGCATGTCGTC-5'
```

In some embodiments, adaptors can include a 3' overhang portion.

```
Left adaptor 3:
                                         (SEQ ID NO: 1)
5'-Phos-CTGCTGTACCGTACATCCGCCTTG-3'

(SEQ ID NO: 2)
3'-GACGACATGGCA-5'

Right adaptor 3:
                                         (SEQ ID NO: 19)
5'-Phos-CTGCTGTACGGCCAAGGCGGATGT-3'

(SEQ ID NO: 20)
3'-GACGACATGCCG-5'
```

In some embodiments, adaptors can include a palindromic or non-palindromic sequence.

```
                                         (SEQ ID NO: 21)
     5'-Phos-ATTATAATTGCGGCCGC-3'

(SEQ ID NO: 22)
         3'-TAATATTAA-5'
```

In some embodiments, a nick can be a site located on one strand of a double-stranded nucleic acid where the site lacks a phosphodiester bond between adjacent nucleotides, while the other strand has adjacent nucleotides joined by a phosphodiester bond at that same location. In some embodiments, a phosphodiester bond can be replaced with analog linkages that join adjacent nucleotides (or nucleotide analogs). In some embodiments, a gap can be a region on one strand of a double stranded polynucleotide that is missing one or more nucleotide resides. In some embodiments, the nucleotide residue at the 3' end of the gap can lack a 5' phosphate residue. In some embodiments, in step (b), one or both strands of the polynucleotide of interest is/are joined to the blocking oligonucleotide adaptor. For example, when one strand of a double-stranded polynucleotide is joined to a blocking oligonucleotide adaptor, a nicked can be formed.

The terms "binding partner(s)" and "binding partner moiet(ies)" can be used interchangeably and in some embodiments, refers to two molecules, or portions thereof, which have a specific binding affinity for one another and typically will bind to each other in preference to binding to other molecules. Typically, binding partners can be polypeptides that can bind or associate with each other. Interactions between the binding partners can be strong enough to allow enrichment and/or purification of a conjugate that comprises a binding partner and a molecule associated with it (e.g., a biotinylated blocking oligonucleotide adaptor). An example of commonly used binding partners includes biotin and streptavidin. Other examples include: biotin or desthiobiotin or photoactivatable biotin and their binding partners avidin, streptavidin, Neutravidin™, or Captavidin™. Another binding partner for biotin can be a biotin-binding protein from chicken (Hytonen, et al., BMC Structural Biology 7:8). Other examples of molecules that function as binding partners include: His-tags which bind with nickel, cobalt or copper; Ni-NTA which binds cysteine, histidine, or histidine patch; maltose which binds with maltose binding protein (MBP); lectin-carbohydrate binding partners; calcium-calcium binding protein (CBP); acetylcholine and receptor-acetylcholine; protein A and anti-FLAG antibody; GST and glutathione; uracil DNA glycosylase (UDG) and ugi (uracil-DNA glycosylase inhibitor) protein; antigen or epitope tags which bind to antibody or antibody fragments, particularly antigens such as digoxigenin, fluorescein, dinitrophenol or bromodeoxyuridine and their respective antibodies; mouse immunoglobulin and goat anti-mouse immunoglobulin; IgG bound and protein A; receptor-receptor agonist or receptor antagonist; enzyme-enzyme cofactors; enzyme-enzyme inhibitors; and thyroxine-cortisol.

Methods for Adaptor-Polynucleotide Joining:

Provided herein are methods for joining together the ends of one or more polynucleotides of interest to one or more blocking oligonucleotide adaptors. For example, methods include joining together one end of a polynucleotide of interest to a blocking oligonucleotide adaptor, or joining together each end of a polynucleotide of interest to a separate blocking oligonucleotide adaptor. Joining together blocking oligonucleotide adaptors and polynucleotides of interest can be used as part of a nucleic acid workflow for preparing one or more nucleic acid constructs.

FIGS. 1A-B and 2 show some embodiments of blocking oligonucleotide adaptors in which left and right blocking oligonucleotide adaptors are joined to a single polynucleotide of interest. For the sake of clarity, the diagram shows only a portion of the polynucleotide(s) of interest.

In some embodiments, methods for joining blocking oligonucleotide adaptors to polynucleotides of interest comprise: joining a linear polynucleotide of interest at its first end to a first oligonucleotide adaptor, and joining the linear polynucleotide of interest at its second end to a second oligonucleotide adaptor, and circularizing the resulting linear construct. A "first end" and a "second end" of a polynucleotide can refer to the 5' end or the 3' end of a polynucleotide of interest. Either the first end or second end of a polynucleotide can be the 5' end or the 3' end of the polynucleotide. In some embodiments, the circularized construct can include nicks on opposite nucleic acid strands.

In some embodiments, methods for preparing mate pair constructs and mate pair libraries comprise joining each end of a linear polynucleotide of interest to a blocking oligonucleotide adaptor which comprise a double-stranded oligonucleotide adaptor (duplex) having an overhang cohesive portion that anneals with a blocking oligonucleotide which can be a separate single-stranded oligonucleotide. In some embodiments, the blocking oligonucleotide adaptor comprises (i) a first and a second single-stranded oligonucleotide annealed together to form a duplex having an overhang portion and (ii) a third single-stranded oligonucleotide annealed to the overhang portion, wherein the overhang portion of the first and second double-stranded oligonucleotide adaptor are capable of annealing with each other, and wherein for the first and second double-stranded oligonucleotide adaptors the end of the duplex having the overhang portion forms an adaptor-joining end and the other end of the duplex forms a target-joining end. In some embodiments, circularizing the linear construct includes removing the third single-stranded oligonucleotide (or a single-stranded portion of an oligonucleotide) from the overhang portions of the first and/or second oligonucleotide adaptors so as to expose the overhang portions of the adaptor-joining ends. In some embodiments, the exposed overhang ends of two separate blocking oligonucleotide adaptors can be annealed together, thereby joining together the adaptor-joining ends of the first and second blocking oligonucleotide adaptors so as to circularize the linear construct. In some embodiments, the adaptors can hybridize without complete overlap between the overhang ends, so as to leave a gap or nick on one or both strands at the junction between the adaptor-joining ends of the first and second adaptors (FIGS. 1A and B-3). In some embodiments, the circularized construct can include nicks on opposite strands. In some embodiments, removing the third single-stranded oligonucleotide from the overhang portions can include a denaturation step using any combination of: elevated temperature, decrease/increase salt concentration (e.g., sodium), and/or formamide.

In some embodiments, methods for preparing a mate pair constructs and mate pair libraries comprise: (a) providing one or more blocking oligonucleotide adaptors; (b) joining one or both ends of a polynucleotide of interest fragment to a separate blocking oligonucleotide adaptor to generate an adaptor-fragment construct; and (c) circularizing the adaptor-fragment construct to generate a circular-adaptor construct having at least one nick in the adaptor region on at least one strand. In some embodiments, the circularized construct can include at least two nicks, one each on opposite strands. In some embodiments, the method further comprises: (d) moving the position of the at least one nick to a new position within the polynucleotide of interest. In some embodiments, the method further comprises: (e) releasing a mate pair construct from the nicked construct by cleaving the strand opposite the at least one nick at the new position.

In some embodiments, methods for preparing mate pair constructs and mate pair libraries comprise: (a) providing a first and a second double-stranded oligonucleotide adaptor each having (i) a first and a second single-stranded oligonucleotide annealed together to form a duplex having an overhang portion and (ii) a third single-stranded oligonucleotide annealed to the overhang portion, wherein the overhang portion of the first and second double-stranded oligonucleotide adaptors are capable of annealing with each other, and wherein for the first and a second double-stranded oligonucleotide adaptors the end of the duplex having the overhang portion forms an adaptor-joining end and the other end of the duplex forms a target-joining end; (b) joining the target-joining end of the first double-stranded oligonucleotide adaptor to at least one strand of the first end of the linear double-stranded polynucleotide of interest; (c) joining the target-joining end of the second double-stranded oligonucleotide adaptor to at least one strand of the second end of the linear double-stranded polynucleotide of interest; (d) removing the third single-stranded oligonucleotide from the first and the second double-stranded oligonucleotide adaptors so as to expose the overhang portions of the adaptor-joining ends; and (e) annealing the exposed overhang portions of the adaptor-joining ends thereby joining together the adaptor-joining ends of the first and the second blocking oligonucleotide adaptors so as to circularize the linear construct. In some embodiments, the circular polynucleotide of interest comprises at least one nick at a junction between the adaptor-joining ends of the first and the second double-stranded oligonucleotide adaptors that were annealed together in step (e). In some embodiments, the circularized construct can include at least two nicks, one each on opposite strands. In some embodiments, annealing the adaptor-joining ends of a first and second blocking oligonucleotide adaptor can include a hybridization step using any combination of: elevated temperature, decrease/increase salt concentration (e.g., sodium), and/or formamide. In some embodiments, removing the third single-stranded oligonucleotide from the overhang portions can include a denaturation step using any combination of: elevated temperature, increase/decrease salt concentration (e.g., sodium), and/or formamide.

In some embodiments, a barcode sequence can be joined to a polynucleotides of interest and/or to a blocking oligonucleotide adaptor to generate barcoded mate pair constructs and barcoded mate pair libraries (FIG. 7). For example, methods for preparing barcoded mate pair constructs and barcoded mate pair libraries can comprise: (a) providing one or more types of barcode adaptors (e.g., BC1 and BC2) and one or more types of blocking oligonucleotide adaptors; (b) joining one or both ends of a polynucleotide of interest to a barcode adaptor to generate a barcode-fragment construct; (c) joining one or both ends of the barcode-fragment construct to a blocking oligonucleotide adaptor to generate a blocking oligonucleotide-barcode-fragment construct; and (d) circularizing the blocking oligonucleotide-barcode-fragment construct.

In some embodiments, preparing a barcoded mate pair construct comprises: (a) providing a first and second double-stranded barcoded adaptor; (b) providing a first and a second double-stranded oligonucleotide adaptor each having (i) a first and a second single-stranded oligonucleotide annealed together to form a duplex having an overhang portion and (ii) a third single-stranded oligonucleotide annealed to the overhang portion, wherein the overhang portion of the first and second double-stranded oligonucleotide adaptors are capable of annealing with each other, and wherein for the first and a second double-stranded oligonucleotide adaptors the end of the duplex having the overhang portion forms an adaptor-joining end and the other end of the duplex forms a target-joining end; (c) joining the first double-stranded barcoded adaptor to the first end of a linear double-stranded polynucleotide of interest; (d) joining the second double-stranded barcoded adaptor to the second end of the linear double-stranded polynucleotide of interest; (e) joining the target-joining end of the first double-stranded oligonucleotide adaptor to the first barcoded adaptor; (f) joining the target-joining end of the second double-stranded oligonucleotide adaptor to the second barcoded adaptor; (g) removing the third single-stranded oligonucleotide from the first and the second double-stranded oligonucleotide adaptors so as to expose the overhang portions of the adaptor-joining ends; and (h) annealing the exposed overhang portions of the adaptor-joining ends thereby joining together the adaptor-joining ends of the first and second blocking oligonucleotide adaptors so as to circularize the barcoded linear polynucleotide of interest. In some embodiments, the overhang portions of first and second double-stranded oligonucleotide adaptors are capable of annealing with each other. In some embodiments, the barcoded circular polynucleotide of interest comprises at least one nick at a junction between the adaptor-joining ends of the first and the second double-stranded oligonucleotide adaptors annealed together in step (h).

Releasing a Mate Pair Construct

Moving a Nick:

In some embodiments, methods for preparing mate pair constructs and barcoded mate pair constructs further comprises the step: moving the at least one nick to a different/new position within a circularized construct. In some embodiments, the at least one nick can be moved to a new position within the double-stranded polynucleotide of interest. For example, the at least one nick can be moved to a new position by conducting a nick translation reaction, or by conducting a combination of exonuclease and strand extension reactions, or by conducting a combination of an exonuclease and cleavage reactions. A nick translation reaction or exonuclease reaction can proceed to the end of the polynucleotide of interest, or can stop at any position along the polynucleotide of interest.

Moving a Nick with a Nick Translation Reaction:

In some embodiments, a nick can be moved to a new position within the double-stranded polynucleotide of interest by conducting a nick translation reaction. For example, a nick translation reaction can be a coupled 5' to 3' DNA polymerization/degradation reaction, or a coupled 5' to 3' DNA polymerization/strand displacement reaction. A nick translation reaction can proceed in a 5' to 3' direction on the nucleic acid strand having a nick.

In some embodiments, moving the at least first nick comprises performing a nick translation reaction on the circularized polynucleotide of interest. In some embodiments, the nick translation reaction can be performed using deoxyribonucleoside triphosphates and an enzyme selected from the group consisting of *E. coli* DNA polymerase I, Taq DNA polymerase, Vent DNA polymerase, Klenow DNA polymerase I, Tfi DNA polymerase, Bst DNA polymerase, and phi29 DNA polymerase.

In some embodiments, the at least one nick can be moved to a new position that is less than about 500 bases, or about 400 bases, or about 300 bases, or about 200 bases, or about 100 bases within the polynucleotide of interest. In some embodiments, the at least one nick can be moved about 25-50 bases, or about 50-75 bases, or about 75-100 bases, or about 100-125 bases, or about 125-150 bases, or about 150-175 bases, or about 175-200 bases, or about 200-300 bases, or about 300-400 bases, or about 400-500 bases, or more. Thus, the length of the polynucleotide of interest in the released mate pair construct can be modulated by adjusting the length of time that the nick translation reaction is permitted to occur.

In some embodiments, methods for preparing mate pair constructs and barcoded mate pair constructs further comprise the step: opening the at least one nick into a gap. In some embodiments, the at least one nick can be opened into a gap by conducting an exonuclease reaction so as to remove at least a portion of the strand having the nick. In some embodiments, a nick can be opened to a gap with an exonuclease which can be a T7 exonuclease, lambda exonuclease, *E. coli* exonuclease III, DNase, or an ATP-dependent DNase.

In some embodiments, methods for preparing mate pair constructs and barcoded mate pair constructs further comprise the step: cleaving the strand opposite the gap so as to release a linear mate pair construct or a barcoded mate pair construct. In some embodiments, the strand opposite the gap can be cleaved with a single-strand specific endonuclease enzyme to release a linear mate pair construct or a barcoded mate pair construct. In some embodiments, the circular polynucleotide of interest can be cleaved with a single-strand specific endonuclease enzyme opposite the new position of the nick (or gap) to release a linear mate pair. In some embodiments, the cleaving can be performed by an enzyme selected from the group consisting of S1 nuclease, mung bean nuclease, nuclease P1, nuclease BAL-31 and nucleases isolated from *Neurospora crassa* or *Ustilago maydis*.

Moving a Nick with Exonuclease and Strand Extension Reactions:

In some embodiments, the moving the at least first nick to a new position can comprise conducting an exonuclease reaction at the nick, and a nucleic acid strand extension reaction.

For example, moving the at least first nick can comprise: (a) conducting an exonuclease reaction on the at least first nick into the polynucleotide of interest so that at least a portion of the polynucleotide of interest is single-stranded (and leaving a terminal 3' end at or near the original location of the at least first nick); and (b) conducting a nucleic acid strand extension reaction at the terminal 3' end and stopping the strand extension reaction prior to the stop position of the exonuclease reaction, so as to leave a portion of the polynucleotide of interest single-stranded. A linear mate pair construct can be released by cleaving the single-stranded portion of the polynucleotide of interest with a single-stranded specific endonuclease enzyme. In some embodiments, an exonuclease reaction can remove a portion or the entire region of the polynucleotide of interest.

In some embodiments, the exonuclease can be conducted with a 5' to 3' exonuclease, such as T7 exonuclease or lambda exonuclease.

In some embodiments, the DNA strand extension reaction can be conducted using a DNA polymerase enzyme.

In some embodiments, a linear mate pair construct can be released by cleaving the single-stranded portion of the polynucleotide of interest with a single-strand specific endonuclease, such as S1 nuclease, mung bean nuclease, P1 nuclease and/or BAL 31 nuclease.

The length of time of the exonuclease and/or strand extension reaction(s) can be modulated to increase or decrease the distance to move the at least one nick to a new position within the polynucleotide of interest.

Moving a Nick with Exonuclease Reactions:

In some embodiments, the moving the at least first nick to a new position can comprise: (a) conducting an exonuclease reaction on the at least first nick so that at least a portion of the polynucleotide of interest is single-stranded; and (b) cleaving the single-stranded portion of the polynucleotide of interest with a single-stranded specific endonuclease enzyme so as to release a linear mate pair construct.

In some embodiments, the exonuclease can be conducted with a 5' to 3' exonuclease, such as T7 exonuclease or lambda exonuclease. In some embodiments, an exonuclease reaction can remove a portion or the entire region of the polynucleotide of interest.

In some embodiments, the single-strand specific endonuclease can be an S1 nuclease, mung bean nuclease, P1 nuclease or BAL 31 nuclease.

Embodiments of Methods

Provided herein are various embodiments for practicing methods of the present teachings. In some embodiments, a workflow for preparing a mate pair library (with or without barcoded adaptors) can include fragmenting the polynucleotide of interest. In some embodiments, the fragmented polynucleotide of interest can be further manipulated, including any combination and in any order: size selection, end repair, adaptor ligation or oligonucleotide ligation (e.g., blocking oligonucleotide adaptors, barcodes adaptors, P1, P2 or A adaptors), adaptor annealing, circularization, moving-a-nick, releasing a linear mate pair construct, nick translation, tailing, amplification, purification, removing linear nucleic acids, washing, quantization, immobilization, and/or denaturation. In some embodiments, additional nucleic acid manipulation steps can include: exonuclease or endonuclease reactions. Any of these steps can be omitted or repeated. In some embodiments, nucleic acid manipulation steps can be conducted under suitable conditions, and include ATP, nucleotides (e.g., dNTPs) or nucleosides, salts, magnesium, manganese, or sodium, or be conducted under suitable pH or temperatures.

In some embodiments, one end of a first polynucleotide of interest can be joined to a first blocking oligonucleotide adaptor, and one end of a second polynucleotide of interest can be joined to a second blocking oligonucleotide adaptor, where the first and second blocking oligonucleotide adaptors can be the same or different.

In some embodiments, polynucleotides of interest can be joined to blocking oligonucleotide adaptors and/or to barcoded adaptors with a ligase enzyme (e.g., T4 DNA ligase).

In some embodiments, methods for preparing a mate pair library can comprise: (A) fragmenting a polynucleotide of interest to generate polynucleotide fragments; (B) size-selecting the polynucleotide fragments; (C) repairing the ends of the polynucleotide fragments to generate repaired polynucleotide fragments; (D) joining each end of the repaired polynucleotide fragments to a biotinylated blocking oligonucleotide adaptor to generate adaptor-fragment constructs, wherein the biotinylated blocking oligonucleotide adaptors include (i) a first and a second single-stranded oligonucleotide annealed together to form a duplex having an overhang portion and (ii) a third single-stranded oligonucleotide annealed to the overhang portion, wherein the overhang portions of the first and second double-stranded oligonucleotide adaptor are capable of annealing with each other, and wherein for the first and second double-stranded oligonucleotide adaptors the end of the duplex having the overhang portion forms an adaptor-joining end and the other end of the duplex forms a target-joining end, and wherein the ends of the repaired polynucleotide fragments are joined to the target-joining end of the blocking oligonucleotide adaptors, and wherein the first or second single-stranded oligonucleotides include at least one biotin moiety; (E) removing the third single-stranded oligonucleotides from the overhang portions so as to expose the overhang portions; (F) annealing together the overhang portions of the biotinylated blocking oligonucleotide adaptors so as to join the adaptor-joining ends thereby circularizing the polynucleotide fragments, wherein the junctions between the adaptor-joining ends includes a nick, and wherein the nicks are located on opposite nucleic acid strands; (G) conducting a nick translation reaction on the nicks so as to move the nicks to a new position within the polynucleotide fragments; (H) stopping the nick translation reaction; (I) conducting an exonuclease reaction at the nicks at the new position so as to open the nicks into gaps; (J) cleaving the strands opposite the gaps with a single-strand specific endonuclease so as to release linear mate pair constructs; (K) adding a non-template nucleotide tail (e.g., A-tail) to the 3' ends of the linear mate pair constructs to generate tailed mate pair constructs; and (L) joining each end of the tailed mate pair constructs to tailed adaptors (e.g., T-tail) having amplification primer sequences and/or sequencing primer sequences (e.g., P1, P2 and/or A adaptors) so as to generate primer-mate-pair constructs having nicks at the junctions between the tailed adaptors and the tailed mate pair constructs; (M) conducting a nick translation to close the nick(s); and (N) amplifying the mate pair construct of step (M).

In some embodiments, an end-repair reaction (step C) can be performed before size-selection (step B). Conducting an end-repair reaction prior to size-selection can improve isolation of larger polynucleotide fragments for preparation of a mate pair library. In some embodiments, conducting an end-repair reaction prior to size-selection can yield a narrower size range for larger polynucleotide fragments such as about 4-6 kb, or about 6-8 kb, or about 8-10 kb, or about 10-12 kb, or about 12-14 kb, or about 14-16 kb, or about 16-18 kb, or about 18-20 kb.

In some embodiments, released mate pair constructs (e.g. at step (J)) can be subjected to an end-repair reaction to generate blunt or overhang ends. In some embodiments, the tailing step (K) can be omitted. In some embodiments, amplification primer adaptors and/or sequencing primer adaptors (e.g., at step L)) need not be tailed adaptors. In some embodiments, joining amplification primer adaptors and/or sequencing primer adaptors (e.g., at step (L)) need not generate a nick at the junction between the adaptors and mate pair constructs. Accordingly, a nick translation step (e.g., step (M)) need not be performed.

Joining Together Two Polynucleotides of Interest

Provided herein are methods for joining together two polynucleotides of interest using blocking oligonucleotide adaptors. For example, one end of a first polynucleotide of interest can be joined to a first blocking oligonucleotide of interest and one end of a second polynucleotide of interest can be joined to a second blocking oligonucleotide of interest, and the overhang portions of the first and second blocking oligonucleotide adaptors can be exposed to permit annealing between the two overhang portions thereby joining together the first and second polynucleotides of interest.

In some embodiments, a first polynucleotide of interest can be joined at its first end to a first blocking oligonucleotide adaptor and a second polynucleotide of interest can be joined at its first end to a second blocking oligonucleotide adaptor. In some embodiments, the first and second blocking oligonucleotide adaptors have a third single-stranded oligonucleotides (or a single-stranded portion of an oligonucleotide) that anneals to the overhang portions. In some embodiments, the third single-stranded oligonucleotides (of the first and second blocking oligonucleotide adaptors) can be removed to expose the overhang portions. In some embodiments, the overhang portions can anneal together thereby joining together the first and second polynucleotides of interest.

In some embodiments, the first and second blocking oligonucleotide adaptors can be joined to first and second polynucleotides of interest, respectively, by hybridization and/or enzymatic ligation.

In some embodiments, one or more junctions between the annealed overhang portions can include a nick or gap. In some embodiments, the nick can be ligated to covalently join together the first and second blocking oligonucleotide adaptors, thereby joining together the first and second polynucleotides of interest. In some embodiments, a nick translation reaction can be conducted on the nick(s). In some embodiments, the nick translation reaction can move in the direction towards and within the polynucleotide of interest. In some embodiments, the nick translation reaction can move to the end(s) of the polynucleotide of interest so as to covalently join together the first and second polynucleotides of interest.

Polynucleotides of Interest

The terms "polynucleotide(s) of interest" and "polynucleotide fragment(s)" can be used interchangeably and refer to nucleic acids that are being analyzed, characterized or manipulated. In some embodiments, polynucleotides of interest can include single-stranded and double-stranded nucleic acids. In some embodiments, polynucleotides of interest can include DNA, RNA or chimeric RNA/DNA. In some embodiments, polynucleotides of interest can be isolated in any form including chromosomal, genomic, organellar (e.g., mitochondrial, chloroplast or ribosomal), recombinant molecules, cloned, subcloned, amplified (e.g., PCR amplified), cDNA, RNA such as precursor mRNA or mRNA, oligonucleotide, or any type of nucleic acid library. In some embodiments, polynucleotides of interest can be isolated from any source including from organisms such as prokaryotes, eukaryotes (e.g., humans, plants and animals), fungus, and viruses; cells; tissues; normal or diseased cells or tissues or organs, body fluids including blood, urine, serum, lymph, tumor, saliva, anal and vaginal secretions, amniotic samples, perspiration, and semen; environmental samples; culture samples; or synthesized nucleic acid molecules prepared using recombinant molecular biology or chemical synthesis methods. In some embodiments, polynucleotides of interest can be chemically synthesized to include any type of natural and/or analog nucleic acid. In some embodiments, polynucleotides of interest can be isolated from a formalin-fixed tissue, or from a paraffin-embedded tissue, or from a formalin-fix paraffin-embedded (FFPE) tissue. In some embodiments, polynucleotides of interest can be associated with counter ions, including $H^+$, $NH_4^+$, trialkylammonium, $Mg^{2+}$ or Nat In some embodiments, the amount of starting material (e.g., polynucleotide of interest) can be about 1 ng-50 ug, or about 1 ng-1 ug, or about 1 ug-5 ug, or about 5 ug-25 ug, or about 25 ug-50 ug.

Fragmentation Methods:

Provided herein are methods for preparing mate pair constructs and mate pair libraries which can comprise a fragmenting step. One or more polynucleotides of interest can be fragmented using mechanical stress, including without limitation: shearing forces, fluid shear, hydrodynamic shear, or pulsatile shear. Mechanical stress can be applied to a polynucleotide of interest by: sonication, nebulization, or cavitation. Mechanical stress can randomly fragment nucleic acids. A polynucleotide of interest can be fragmented with enzymatic reactions, such as: any type I, type II, type IIs, type IIB, type III or type IV restriction endonucleases; any nicking endonuclease restriction enzymes; endonuclease (e.g., DNase I); and/or exonuclease enzymes. A polynucleotide of interest can be fragmented with an enzyme cocktail, for example Fragmentase™ (New England Biolabs). A polynucleotide of interest can be fragmented with a transposase and transposable element, for example Nextera™ technology from Epicentre. A polynucleotide of interest can be fragmented using any chemical reactions, including: dimethyl sulfate; hydrazine, NaCl, piperidine, or acid. A polynucleotide of interest can be fragmented using any type of high energy radiation, such as ultraviolet radiation. In some embodiments, polynucleotides of interest can be fragmented to a size range of about 200 bp-1 kb, or about 500 bp-1 kb, or about 700 bp-1 kb, or about 1 kb-2 kb, or about 1 kb-3 kb, or about 1 kb-4 kb, or about 1 kb-5 kb, or about 1 kb-6 kb, or about 1 kb-7 kb or larger.

Size Selection Methods:

Provided herein are methods for preparing mate pair constructs and mate pair libraries which can comprise a size-selecting step to obtain polynucleotide fragments having any desired size or size range. In some embodiments, polynucleotide fragments are not size-selected. A nucleic acid size selection method can include without limitation: solid phase adherence or immobilization; electrophoresis, such as gel electrophoresis; and chromatography, such as HPLC and size exclusion chromatography. A solid phase adherence/immobilization method can typically involve micro paramagnetic beads coated with a chemical functional group that interacts with nucleic acids under certain ionic strength conditions with or without polyethylene glycol or polyalkylene glycol.

Examples of solid phase adherence/immobilization methods include but are not limited to; SPRI (Solid Phase Reversible Immobilization) beads from Agencourt (see Hawkins 1995 Nucleic Acids Research 23:22) which are carboxylate-modified paramagnetic beads; MagNA Pure™ magnetic glass particles (Roche Diagnostics, Hoffmann-La Roche Ltd.); MagneSil™ magnetic bead kit from Promega; Bilatest™ magnetic bead kit from Bilatec AG; Magtration™ paramagnetic system from Precision System Science, Inc.; Mag-Bind™ from Omega Bio-Tek; MagPrep™ silica from Merck/Estapor; SNARe™ DNA purification system from Bangs; and Chemagen™ M-PVA beads from Chemagen.

In some embodiments, size-selected polynucleotide fragments can be about 50-3000 base pairs in length, or about 50-2000 base pairs in length, or about 50-1500 base pairs in length, or about 50-1000 base pairs in length, or about 50-700 base pairs in length. In some embodiments, size-selected nucleic acid fragments can be about 50-150 bases, or about 150-250 bases, or about 250-500 bases, or about 500-1000 bases, or about 1000-2000 bases in length. In some embodiments, size-selected nucleic acid fragments can be about 1-3 kb, or about 3-6 kb, or about 6-10 kb, or about 10-15 kb, or about 15-20 kb, or about 20-25 kb, or about 25-30 kb, or about 30-40 kb, or about 40-50 kb, or about 50-75 kb, or about 75-100 kb, or about 100-150 kb, or about 150-200 kb, or longer.

Repairing Methods:

Provided herein are methods for preparing mate pair constructs and mate pair libraries which can comprise a repair step (e.g., "end repairing" or "repairing the ends" or "repair"). Polynucleotide fragments can be fragmented to generate nucleic acid fragments having a first end and a second end. A fragmenting step can generate first ends, second ends, or internal portions, having undesirable features, such as nicks, overhang ends, ends lacking a phosphorylated end, ends having a phosphorylated end, or nucleic acid fragments having apurinic or apyrimidinic residues. Polynucleotide fragments can be repaired at one or both ends, and/or repaired at an internal region. In some embodiments, enzymatic reactions can be conducted to repair one or more ends or internal portions. In some embodiments, enzymatic reactions can be conducted to convert overhang ends to blunt ends, or to phosphorylate or de-phosphorylate the 5' end of a strand, or to close nicks, or to repair oxidized guanines or pyrimidines, or to repair deaminated cytosines, or to hydrolyze the apurinic or apyrimidinic residues. In some embodiments, an enzymatic reaction can generate an overhang end (e.g., sticky end). For example, restriction endonucleases or a tailing enzyme can generate an overhang end.

In some embodiments, repairing or end-repairing nucleic acid fragments includes contacting nucleic acid fragments, or contacting a plurality of first ends and/or second ends with: an enzyme to close single-stranded nicks in duplex DNA (e.g., T4 DNA ligase); an enzyme to phosphorylate the 5' end of at least one strand of a duplex DNA (e.g., T4 polynucleotide kinase); an enzyme to remove a 5' phosphate (e.g., any phosphatase enzyme, such as calf intestinal alkaline phosphatase, bacterial alkaline phosphatase, shrimp alkaline phosphatase, Antarctic phosphatase, and placental alkaline phosphatase); an enzyme to remove 3' overhang ends (e.g., DNA polymerase I, Large (Klenow) fragment, T4 DNA polymerase, mung bean nuclease); an enzyme to fill-in 5' overhang ends (e.g., T4 DNA polymerase, Tfi DNA polymerase, Tli DNA polymerase, Taq DNA polymerase, Large (Klenow) fragment, phi29 DNA polymerase, Mako DNA polymerase (Enzymatics, Beverly, Mass.), or any heat-stable or heat-labile DNA polymerase); an enzyme to remove 5' overhand ends (e.g., S1 nuclease); an enzyme to remove 5' or 3' overhang ends (e.g., mung bean nuclease); an enzyme to hydrolyze single-stranded DNA (e.g., nuclease P1); an enzyme to remove both strands of double-stranded DNA (e.g., nuclease Bal-31); and/or an enzyme to remove an apurinic or apyrimidinic residue (e.g., endonuclease IV). In some embodiments, a polymerase can have exonuclease activity, or have a reduced or lack of nuclease activity.

A repairing or end-repairing reaction can be supplemented with additional repairing enzymes in any combination and in any amount, including: endonuclease IV (apurinic-apyrimidinic removal), Bst DNA polymerase (5'>3' exonuclease for nick translation) formamidopyrimidine DNA glycosylase (FPG) (e.g., base excision repair for oxidized purines) uracil DNA glycosylase (uracil removal), T4 endonuclease V (pyrimidine removal) and/or endonuclease VIII (removes oxidized pyrimidines). In some embodiments, a repairing or end-repairing reaction can be conducted in the presence of appropriate co-factors, including dNTPs, NAD, $(NH_4)SO_4$, KCl, and/or $MgSO_4$. In some embodiments, the additional repairing enzymes can be included in a repair or end-repairing reaction at any concentration, including: about 0.1-1 U/uL, or about 1-2 U/uL, or about 2-3 U/uL, or about 3-4 U/uL, or about 5 U/uL, or about 5-10 U/uL, or about 10-15 U/uL, or about 15-20 U/uL, or more.

In some embodiments, a repairing or end-repairing step can be performed in the presence of appropriate buffers and/or nucleotides (including nucleotide analogs or biotinylated nucleotides), and at an appropriate pH and temperature(s). A repairing or end-repairing step can be conducted in the presence of a nucleic acid damage-mitigating composition.

Tailing Methods:

Provided herein are methods for preparing mate pair constructs and mate pair libraries which can comprise a tailing step. One or more non-template nucleotides can be enzymatically added to a first end and/or a second end of a nucleic acid (e.g., polynucleotide fragment, or a first or second single-stranded oligonucleotide). In some embodiments, a DNA polymerase can be used to add one or more non-template nucleotides to a terminal 3' end of a nucleic acid strand. In some embodiments, a non-proofreading DNA polymerase can be used to add a single non-template A-residue to a 3' end a of a nucleic acid strand. In some embodiments, a DNA polymerase can be a Taq DNA polymerase (or a derivative thereof). In some embodiments, DNA polymerases having proofreading activity can be used to add a single non-template 3' A-tail. In some embodiments, a DNA polymerase can be a Tfi (exo minus) DNA polymerase, large (Klenow) fragment (3'>5' exo minus), or derivative polymerases thereof. In some embodiments, T4 DNA polymerase (e.g., exo-) can be used to add a non-template, single nucleotide residue to a 3' end of a nucleic acid strand. In some embodiments, a first end and/or a second end of a nucleic acid lack a nucleotide tail.

Adaptor-Joining Methods:

Provided herein are methods for preparing mate pair constructs and mate pair libraries which can comprise an adaptor-joining step. A polynucleotide fragment (e.g., fragments of polynucleotides of interest) can be joined to one or more nucleic acid adaptors by hybridization or enzymatic ligation to generate adaptor-fragment constructs.

In some embodiments, one end or both ends of nucleic acid fragments can be joined to at least one type of adaptor. One or both ends of a polynucleotide fragment can be joined to at least one nucleic acid adaptor, including blocking oligonucleotide adaptors, barcoded adaptors, sequencing primer adaptors, amplification primer adaptors, universal adaptors and/or others.

In some embodiments, adaptors can be joined to one or both ends of polynucleotide fragments essentially simultaneously or sequentially. For example, each end of a polynucleotide fragment can be joined to adaptors in a joining reaction (e.g., essentially simultaneous adaptor-joining). In another example, in a first step, one end of a polynucleotide fragment can be joined to a first adaptor, and in a second step the other end of the polynucleotide fragment can be joined to a second adaptor (e.g., sequential adaptor-joining steps). A skilled artisan will appreciate that other combinations of adaptor-joining reactions can be practiced.

In some embodiments, an adaptor can be single-stranded or double-stranded nucleic acids, or can include single-stranded or double-stranded portions. In some embodiments, an adaptor can have any structure, including linear, hairpin, forked, or stem-loop.

In some embodiments, an adaptor can be a blocking oligonucleotide adaptor which comprises a double-stranded oligonucleotide adaptor (duplex) having an overhang cohesive portion of anneals with a blocking oligonucleotide which can be a separate single-stranded oligonucleotide.

In some embodiments, an adaptor can include nucleotide sequences that are complementary to sequencing primers (e.g., P1, P2 and/or A), amplification primers, universal sequences and/or barcode sequences. For example, released mate pair constructs can be joined at each end to a different sequencing adaptor to prepare a nucleic acid library for sequencing with SOLiD™ sequencing reactions (WO 2006/084131) or sequencing with ion-sensitive sequencing reactions (e.g., Ion Torrent PGM™ sequencer from Life Technologies Corporation).

In some embodiments, an adaptor can have any length, including fewer than 10 bases in length, or about 10-20 bases in length, or about 20-50 bases in length, or about 50-100 bases in length, or longer.

In some embodiments, an adaptor can have any combination of blunt end(s) and/or sticky end(s). In some embodiments, at least one end of an adaptor can be compatible with at least one end of a nucleic acid fragment. In some embodiments, a compatible end of an adaptor can be joined to a compatible end of a nucleic acid fragment. In some embodiments, an adaptor can have a 5' or a 3' overhang end.

In some embodiments, an adaptor can have a 3' overhang end with at least one phosphorothiolate, phosphorothioate, and/or phosphoramidate linkage. In some embodiments, an adaptor can have a 3' overhang end with at least two phosphorothioate linkages.

In some embodiments, an adaptor can include a monomeric sequences (e.g., AAA, TTT, CCC, or GGG) of any length, or an adaptor can include a complex sequence (e.g., non-monomeric sequence), or can include both monomer and complex sequences.

In some embodiments, an adaptor can have a 5' or 3' tail. In some embodiments, the tail can be one, two, three, or more nucleotides in length. In some embodiments, an adaptor can have a tail comprising adenine, thymine, cytosine and/or guanine base (or analogs thereof). In some embodiments, an adaptor can have a monomeric tail sequence of any length. In some embodiments, at least one end of an adaptor can have a tail that is compatible with a tail on one end of a nucleic acid fragment. In some embodiments, an adaptor can lack a terminal tail.

In some embodiments, an adaptor can include an internal nick. In some embodiments, an adaptor can have at least one strand that lacks a terminal 5' phosphate residue. In some embodiments, an adaptor lacking a terminal 5' phosphate residue can be joined to a nucleic acid fragment to introduce a nick at the junction between the adaptor and the nucleic acid fragment.

In some embodiments, an adaptor can include one or more universal bases (e.g., inosine). In some embodiments, an adaptor can include one or more ribonucleoside residues. In some embodiments, an adaptor can be chimeric RNA/DNA. In some embodiments, an adaptor can include at least one scissile linkage. In some embodiments, a scissile linkage can be susceptible to cleavage or degradation by an enzyme or chemical compound. In some embodiments, an adaptor can include one or more uracil residues. In some embodiments, an adaptor can include at least one phosphorothiolate, phosphorothioate, and/or phosphoramidate linkage.

In some embodiments, an adaptor can include identification sequences. In some embodiments, an identification sequence can be a unique sequence (e.g., barcode sequence). In some embodiments, an identification sequence can be used for sorting or tracking. In some embodiments, a mate pair construct can include one or more identification sequences (e.g., barcodes) that are the same or different. In some embodiments, a barcode sequence can allow identification of a particular adaptor among a mixture of different adaptors having different barcodes sequences. For example, a mixture can include 2, 3, 4, 5, 6, 7-10, 10-50, 50-100, 100-200, 200-500, 500-1000, or more different adaptors having unique barcode sequences. In some embodiments, a plurality of polynucleotide fragments which are joined to blocking oligonucleotide adaptors and at least one unique identifier adaptor (e.g., barcoded adaptor) can be pooled together for any manipulation, including size selection, end repair, adaptor ligation, adaptor annealing, circularization, moving-a-nick, releasing a linear mate pair construct, nick translation, tailing, amplification, purification, removing linear nucleic acids, washing, quantization, immobilization, denaturation and/or attachment to a solid surface. Examples of a polynucleotide fragment joined to a barcode are described in U.S. Ser. No. 13/026,046.

In some embodiments, adaptors can include any type of restriction enzyme recognition sequence, including type I, type II, type IIs, type IIB, type III or type IV restriction enzyme recognition sequences. For example, adaptors can include an Ecop15I or MmeI recognition site. In some embodiments, adaptors can include a nicking restriction enzyme sequence, including: EcoP15I, Nb.BbvCI, Nb.BsmI, Nb.BsrDI, Nb.BtsI, Nt.AlwI, Nt.BbvCI, or Nt.BstNBI.

In some embodiments, the adaptors can include a cell regulation sequences, including a promoter (inducible or constitutive), enhancers, transcription or translation initiation sequence, transcription or translation termination sequence, secretion signals, Kozak sequence, cellular protein binding sequence, and the like.

In some embodiments, any component of a blocking oligonucleotide adaptor can include a binding partner (e.g., biotin or streptavidin moiety) to permit separation from undesirable reagents in a reaction. In some embodiments, a first or a second single-stranded oligonucleotide, which can anneal to form a duplex structure having an overhang portion, can include a binding partner. In some embodiments, a third single-stranded oligonucleotide (a blocking oligonucleotide which anneals to an overhang end) can include a binding partner.

In some embodiments, one or more type(s) of adaptors can be joined to polynucleotide fragments, where the adaptors are present in a ligation reaction at about 10×-300× (or higher) relative to the amount of nucleic acid fragments. For example, adaptors can be present in an amount that is about 10×, or about 20×, or about 30×, or about 50×, or about 75×, or about 100×, or about 150×, or about 200×, or about 250×, or about 300×, or higher amounts compared to the amount of polynucleotide fragments. In some embodiments, molar amounts of adaptors can be compared to molar amounts of polynucleotide fragments. One skilled in the art will readily recognize that other unit amounts of adaptors and polynucleotide fragments can be compared.

In some embodiments, a mate pair construct can include an adaptor having amplification and/or sequencing primer sequences, such as those shown in Table 1 below.

TABLE 1

| Adaptors: | Sequence | SEQ ID NOS: |
|---|---|---|
| P1-Adaptor (top strand) | 5'CCACTACGCCTCCGCTTTCCTCTCTATGGGCAGTCGGTGFT3' | 23 |
| P1-Adaptor (bottom strand) | 5'TCACCGACTGCCCATAGAGAGGAAAGCGGAGGCGTAGTGEOC3' | 24 |
| P2-LMP Adaptor (top strand) | 5'GAGAATGAGGAACCCGGGGCAEOC3' | 25 |
| P2-LMP Adaptor (bottom strand) | 5'CTGCCCCGGGTTCCTCATTCTOT3' | 26 |
| PCR primer 1 | 5'CCACTACGCCTCCGCTTTCCTCTCTATG3' | 27 |
| PCR primer 2 | 5'CTGCCCCGGGTTCCTCATTCT3' | 28 |
| PCR primer 3 | 5'CCATCTCATCCCTGCGTGTC3' | 29 |
| P1-adaptor ION (top strand) | 5'CCACTACGCCTCCGCTTTCCTCTCTATGGGCAGTCGGTGAT3' | 30 |
| P1-adaptor ION (bottom strand) | 3'MMGGTGATGCGGAGGCGAAAGGAGAGATACCCGTCAGCCACTA5' | 31 |
| A-adaptor (top strand) | 5'CCATCTCATCCCTGCGTGTCTCCGACTCAG3' | 32 |
| A-adaptor (bottom strand) | 3'MMGGTAGAGTAGGGACGCACAGAGGCTGAGTC5' | 33 |

LEGEND:
F = A-3'phosphorothioate
E = G-3'phosphorothioate
O = C-3'phosphorothioate
M = T-3' phosphorothioate In some embodiments, a mate pair construct can include at least one of the identification sequences (e.g., barcodes) listed in Table 2 below. For example, a mate pair construct can be joined to an adaptor comprising a barcode sequence. The identification sequences are shown in a 5'>3' orientation.

TABLE 2

| BC: | Sequence: | SEQ ID NO: |
|---|---|---|
| 1 | CCTCTTACAC | SEQ ID NO. 34 |
| 2 | ACCACTCCCT | SEQ ID NO. 35 |
| 3 | TATAACCTAT | SEQ ID NO. 36 |
| 4 | GACCGCATCC | SEQ ID NO. 37 |
| 5 | CTTACACCAC | SEQ ID NO. 38 |
| 6 | TGTCCCTCGC | SEQ ID NO. 39 |
| 7 | GGCATAACCC | SEQ ID NO. 40 |
| 8 | ATCCTCGCTC | SEQ ID NO. 41 |
| 9 | GTCGCAACCT | SEQ ID NO. 42 |

TABLE 2-continued

| BC: | Sequence: | SEQ ID NO: |
|---|---|---|
| 10 | AGCTTACCGC | SEQ ID NO. 43 |
| 11 | CGTGTCGCAC | SEQ ID NO. 44 |
| 12 | TTTTCCTCTT | SEQ ID NO. 45 |
| 13 | GCCTTACCGC | SEQ ID NO. 46 |
| 14 | TCTGCCGCAC | SEQ ID NO. 47 |
| 15 | CATTCAACTC | SEQ ID NO. 48 |
| 16 | AACGTCTCCC | SEQ ID NO. 49 |
| 17 | GCGGTGAGCC | SEQ ID NO. 50 |
| 18 | TCATCCGCCT | SEQ ID NO. 51 |
| 19 | CAGTTACCAT | SEQ ID NO. 52 |
| 20 | AAAGCTTGAC | SEQ ID NO. 53 |
| 21 | GGAACCGCAC | SEQ ID NO. 54 |
| 22 | TCATCTTCTC | SEQ ID NO. 55 |
| 23 | CAAGCACCGC | SEQ ID NO. 56 |
| 24 | ATACCGACCC | SEQ ID NO. 57 |
| 25 | TCATCATGTT | SEQ ID NO. 58 |
| 26 | CGGGCTCCCG | SEQ ID NO. 59 |
| 27 | AAGTTTGCTG | SEQ ID NO. 60 |
| 28 | GTAGTAAGCT | SEQ ID NO. 61 |
| 29 | CCCTAGATTC | SEQ ID NO. 62 |
| 30 | TCTTCGCTAC | SEQ ID NO. 63 |
| 31 | ACGCACCAGC | SEQ ID NO. 64 |
| 32 | GCACCCAACC | SEQ ID NO. 65 |
| 33 | GTATCCAACG | SEQ ID NO. 66 |
| 34 | CCTTTAACGA | SEQ ID NO. 67 |
| 35 | TCCTACGCTT | SEQ ID NO. 68 |
| 36 | ATGTGAGAAC | SEQ ID NO. 69 |
| 37 | GGTATAACAG | SEQ ID NO. 70 |
| 38 | CTAAGACGAC | SEQ ID NO. 71 |
| 39 | ACTCACGATA | SEQ ID NO. 72 |
| 40 | TAACCCTTTT | SEQ ID NO. 73 |
| 41 | CAATCCCACA | SEQ ID NO. 74 |
| 42 | TAGTACATTC | SEQ ID NO. 75 |
| 43 | AACCCTAGCG | SEQ ID NO. 76 |
| 44 | GATCATCCTT | SEQ ID NO. 77 |
| 45 | AGCCAAGTAC | SEQ ID NO. 78 |
| 46 | TTCGACGACC | SEQ ID NO. 79 |
| 47 | GCCATCCCTC | SEQ ID NO. 80 |
| 48 | CACTTACGGC | SEQ ID NO. 81 |
| 49 | CTTATGACAT | SEQ ID NO. 82 |
| 50 | GCAAGCCTTC | SEQ ID NO. 83 |
| 51 | ACTCCTGCTT | SEQ ID NO. 84 |
| 52 | TTACAATTAC | SEQ ID NO. 85 |
| 53 | ACTTGATGAC | SEQ ID NO. 86 |
| 54 | TCCGCCTTTT | SEQ ID NO. 87 |
| 55 | CGCTTAAGCT | SEQ ID NO. 88 |
| 56 | GGTGACATGC | SEQ ID NO. 89 |
| 57 | TTCTTACTAG | SEQ ID NO. 90 |
| 58 | CGCCACTTTA | SEQ ID NO. 91 |
| 59 | GACATTACTT | SEQ ID NO. 92 |
| 60 | ACCGAGGCAC | SEQ ID NO. 93 |
| 61 | CGATAATCTT | SEQ ID NO. 94 |
| 62 | ACCCTCACCT | SEQ ID NO. 95 |
| 63 | TCGAACCCGC | SEQ ID NO. 96 |
| 64 | GGTGTAGCAC | SEQ ID NO. 97 |
| 65 | GCTTGATCCC | SEQ ID NO. 98 |
| 66 | ACATTACATC | SEQ ID NO. 99 |
| 67 | CCCTAAGGAC | SEQ ID NO. 100 |
| 68 | TCGTCAATGC | SEQ ID NO. 101 |
| 69 | AAAGCATATC | SEQ ID NO. 102 |
| 70 | TCTGTAGGGC | SEQ ID NO. 103 |
| 71 | CGTTCCCTGT | SEQ ID NO. 104 |
| 72 | GTATTCACTT | SEQ ID NO. 105 |
| 73 | ACGTCATTGC | SEQ ID NO. 106 |
| 74 | TCAGCGTCCT | SEQ ID NO. 107 |
| 75 | GCCCAGATAC | SEQ ID NO. 108 |
| 76 | CCTAAAACTT | SEQ ID NO. 109 |
| 77 | AAGACCAGAT | SEQ ID NO. 110 |
| 78 | GATGATTGCC | SEQ ID NO. 111 |
| 79 | TAATTCTACT | SEQ ID NO. 112 |
| 80 | CACCGTAAAC | SEQ ID NO. 113 |
| 81 | AATGACGTTC | SEQ ID NO. 114 |
| 82 | CTCCCTTCAC | SEQ ID NO. 115 |
| 83 | TACGCCATCC | SEQ ID NO. 116 |
| 84 | GTTCATCCGC | SEQ ID NO. 117 |
| 85 | AACGCTTTCC | SEQ ID NO. 118 |
| 86 | TCCTGGTACT | SEQ ID NO. 119 |
| 87 | GCTTTGCTAT | SEQ ID NO. 120 |

TABLE 2-continued

| BC: | Sequence: | SEQ ID NO: |
|---|---|---|
| 88 | CATGATCAAC | SEQ ID NO. 121 |
| 89 | TAGACAGCCT | SEQ ID NO. 122 |
| 90 | AGTAGGTCAC | SEQ ID NO. 123 |
| 91 | CCCAATACGC | SEQ ID NO. 124 |
| 92 | GTAATCCCTT | SEQ ID NO. 125 |
| 93 | GCATCGTAAC | SEQ ID NO. 126 |
| 94 | AAACACCCAT | SEQ ID NO. 127 |
| 95 | TGCCGGACTC | SEQ ID NO. 128 |
| 96 | CTCTTCGATT | SEQ ID NO. 129 |

Circularization Methods:

Provided herein are methods for preparing mate pair constructs and mate pair libraries which can comprise a circularizing step. Methods for circularizing a polynucleotide fragment comprise: joining a linear polynucleotide fragment at its first end to a first oligonucleotide adaptor, and joining the linear polynucleotide fragment at its second end to a second oligonucleotide adaptor, and circularizing the resulting linear construct. In some embodiments, the circularized construct can include nicks on opposite strands. In some embodiments, methods for circularizing a polynucleotide fragment comprise joining each end of a linear polynucleotide fragment to a blocking oligonucleotide adaptor which comprise a double-stranded oligonucleotide adaptor (duplex) having an overhang cohesive portion that anneals with a blocking oligonucleotide which can be a separate single-stranded oligonucleotide. In some embodiments, the blocking oligonucleotide adaptor comprises (i) a first and a second single-stranded oligonucleotide annealed together to form a duplex having an overhang portion and (ii) a third single-stranded oligonucleotide annealed to the overhang portion, wherein the overhang portion of the first and second double-stranded oligonucleotide adaptor are capable of annealing with each other, and wherein for the first and second double-stranded oligonucleotide adaptors the end of the duplex having the overhang portion forms an adaptor-joining end and the other end of the duplex forms a target-joining end. In some embodiments, circularizing the linear construct includes removing the third single-stranded oligonucleotide (or a single-stranded portion of an oligonucleotide) from the overhang portions of the first and/or second oligonucleotide adaptors so as to expose the overhang portions of the adaptor-joining ends. In some embodiments, the exposed overhang ends of two separate adaptors can be annealed together, thereby circularizing the linear construct. In some embodiments, the adaptors can hybridize without complete overlap between the overhang ends, so as to leave a gap or nick on one or both strands at the junction between the adaptor-joining ends of the first and second adaptors (FIGS. 1A and B-3). In some embodiments, the circularized construct can include nicks on opposite strands.

In some embodiments, a blocking oligonucleotide can be removed from an overhang end, and a pair of overhang ends can anneal with each other, under conditions suitable for nucleic acid duplex annealing and/or denaturing. One skilled in the art can conduct nucleic acid annealing and/or denaturation by modify temperature, salts, formamide, length of time, and other factors. In some embodiments, the circularized construct can include at least one nick in the adaptor-joining region on at least one strand.

In some embodiments, any linear molecules remaining after a circularization step can be removed by treatment with an enzyme that degrades linear nucleic acids, including treatment with Plasmid Safe™ ATP-Dependent DNase kit (Epicentre). In some embodiments, linear nucleic acids can be removed with a column or CsCl centrifugation.

Nick Translation Methods:

Provided herein are methods for preparing mate pair constructs and mate pair libraries which can comprise a nick translation step. A nick translation reaction can be conducted at least once at any stage in the library preparation workflow. A nick translation reaction can be used to move a nick to a new position along a nucleic acid or to close a nick or gap. In some embodiments, a nick translation reaction can be a coupled 5' to 3' DNA polymerization/degradation reaction, or a coupled 5' to 3' DNA polymerization/strand displacement reaction. A nick translation reaction can be conducted with a DNA polymerase and deoxynucleotide triphosphates. Methods for performing nick translation reactions are known to those of skill in the art (Rigby, P. W. et al. (1977), J. Mol. Biol. 113, 237). Methods for preparing mate pair libraries using an internal adaptor (IA) and a nick translation reaction are known (U.S. 2009/0181861). A variety of suitable polymerases can be used to conduct a nick translation reaction, including for example, E. coli DNA polymerase I, Taq DNA polymerase, Vent DNA polymerase, Klenow DNA polymerase I, Tfi DNA polymerase, Bst DNA polymerase, and phi29 DNA polymerase. Depending on the enzyme used, a nick translation reaction can proceed by 5' to 3' exonuclease activity, or by 5' to 3' strand displacement. In some embodiments, a mutant enzyme with low activity can be used to conduct a nick translation reaction. Mutant enzymes can exhibit lower extension rates, lower 5' to 3' exonuclease activity, lower 5' to 3' polymerase activity, lower 5' to 3' strand displacement activity, or any combination thereof. In some embodiments, mutant enzymes can be sensitive to reaction conditions such as, for example, cations, temperature or pH.

The distance that a nick travels (moves) can be modulated by reaction conditions, such as reaction time, reaction temperature, the polymerase used, pH, ions or cations present, and/or salt conditions. A nick translation reaction can be conducted at a temperature range of about 0° C. to about 40° C., or about 5° C. to about 10° C., or about 10° C. to about 15° C., or about 15° C. to about 20° C., or about 20° C. to about 25° C., or about 25° C. to about 30° C., or about 30° C. to about 35° C., or about 35° C. to about 40° C. A nick translation reaction can be conducted for about 1, 2, 3, 4, 5, 6, 7, 8, 9, 10, 11, 12, 13, 14, 15, 16, 17, 18, 19 or 20 minutes. A nick translation reaction can be terminated or slowed by increasing the temperature, decreasing the temperature, altering the pH, altering the ions present, altering the salt conditions, and/or addition of a chelating agent. In some embodiments, circularized nucleic acid molecule can be cleaved by allowing a nick translation reaction to proceed around the nucleic acid molecule until it encounters the other nick; so as to self-cleave the circular molecule.

Figure 5:
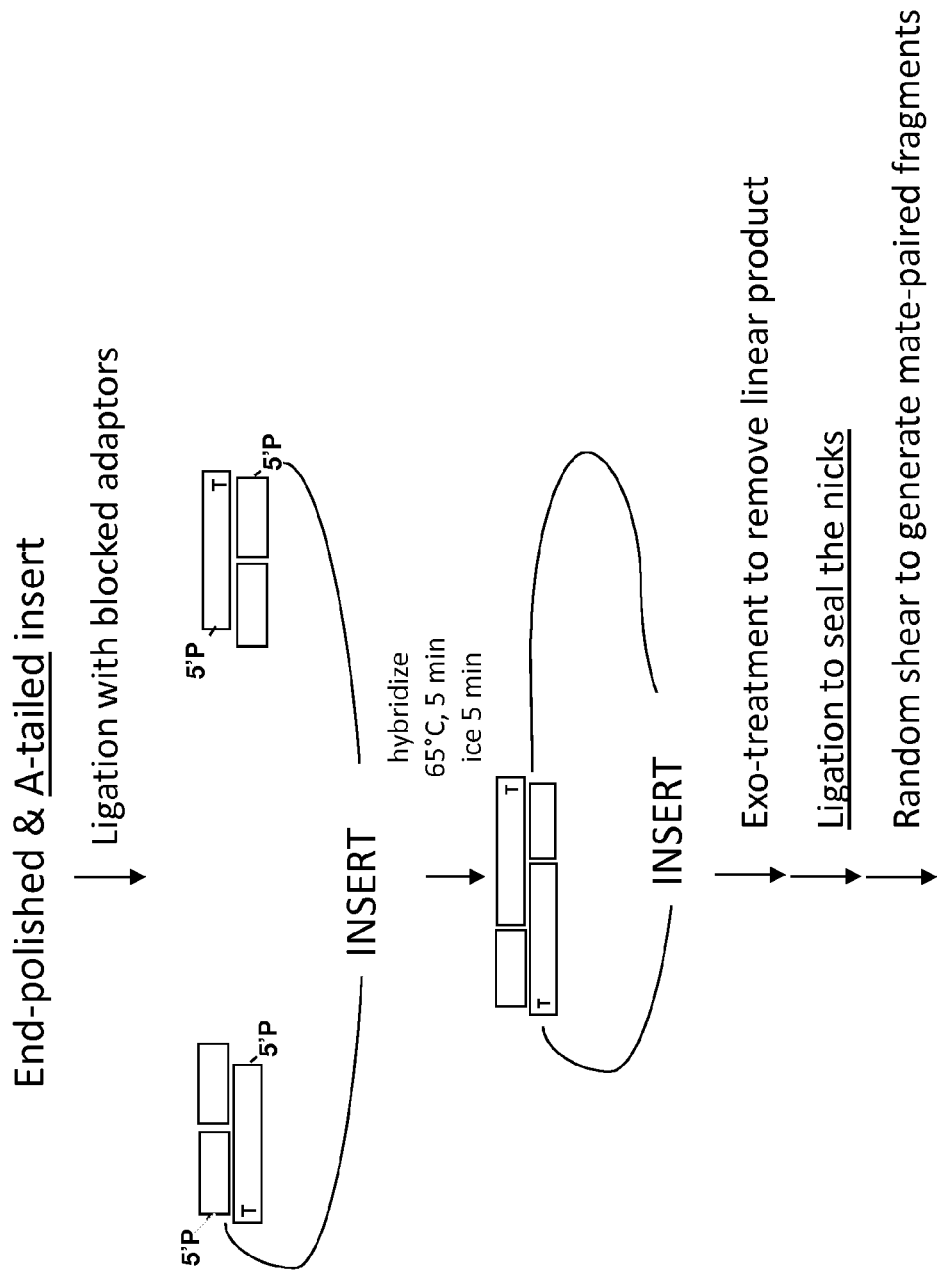
FIG. 5 is a schematic showing a non-limiting example of a method for circularizing a polynucleotide of interest using a pair of blocking oligonucleotide adaptors and releasing a mate pair construct.

Methods for Releasing a Mate Pair:

Provided herein are methods for preparing mate pair constructs and mate pair libraries which can comprise a step for releasing a linear mate pair from a circular construct. In some embodiments, a linear mate pair construct can be released from a circular construct by employing any combination of enzymatic reactions to (a) open a nick to make a gap (e.g., on a first strand) and (b) cleave the strand opposite the nick (e.g., on the opposite strand). In some embodiments, a nick can be opened to a gap with an exonuclease such as a T7 exonuclease, lambda exonuclease, *E. coli* exonuclease III, DNase, or an ATP-dependent DNase. In some embodiments, a strand opposite the gap can be cleaved with a single-strand specific endonuclease enzyme such as S1 nuclease, nuclease P1, nuclease BAL-31 or mung bean nuclease. In some embodiments, a circular construct can be subjected to random shearing forces to release linear fragments and a linear mate pair construct (FIG. 5).

Methods for Purifying:

Provided herein are methods for preparing mate pair constructs and mate pair libraries which can comprise a purifying step. A purifying step can include separating polynucleotides fragments from non-desirable components (e.g., buffers, salts, enzymes, primer-dimers, or excess adaptors or primers). In some embodiments, a purification procedure can be conducted at least once at any stage in a workflow. Purification procedures include without limitation: bead purification, column purification, gel electrophoresis, dialysis, alcohol, precipitation, size-selective PEG precipitation and the like. In some embodiments, a polynucleotide fragment, joined to a blocking oligonucleotide adaptor having a binding partner (e.g., biotin), can be separated from undesirable reagents in a reaction by binding the binding partner to a surface (e.g., planar or a bead) having a cognate binding partner (e.g., streptavidin). In some embodiments, solid phase adherence/immobilization methods can be used for purification. For example, SPRI (Solid Phase Reversible Immobilization) beads from Agencourt can be used for purification. In some embodiments, unreacted nucleic acids (e.g., non-ligated blocking oligonucleotide adaptors, blocking oligonucleotides, polynucleotides of interest) can be removed by digesting with DNase, leaving intact polynucleotides of interest joined to blocking oligonucleotide adaptors.

Denaturation and Hybridization Methods:

Provided herein are methods for preparing mate pair constructs and mate pair libraries which can comprise a nucleic acid denaturation or an annealing step. Nucleic acids can be denatured or hybridized by adjusting the: temperature, pH, sodium concentration, and/or formamide concentration. In some embodiments, the released linear mate pair can be denatured into two single strands.

Immobilization Methods:

Provided herein are methods for preparing mate pair constructs and mate pair libraries which can comprise an immobilization step. A mate pair (single- or double-stranded) can be immobilized to a surface. In some embodiments, the surface can be a planar surface or a bead. For example, one end of a single-stranded mate pair can be modified with a chemical compound that will react with, and attach to another chemical compound on the surface. In another example, one end of a single-stranded mate pair can include a capture adaptor sequence for annealing to a capture primer which is immobilized on a surface. In some embodiments, an immobilized single-stranded mate pair can be subjected to bridge amplification reactions. In some embodiments, a mate pair construct can be attached or immobilized to Ion Sphere™ Particles (sold as a component of the Ion Xpress Template Kit (Part No. 4469001)) for clonal amplification Immobilization to Ion Sphere™ Particles can be performed essentially according to the protocols provided in the Ion Xpress™ Template Kit v2.0 User Guide (Part No.: 4469004)).

Polymerases:

Provided herein are methods for preparing mate pair constructs and mate pair libraries which can utilize one or more polymerases. In some embodiments, a polymerase includes any enzyme, or fragment or subunit of thereof, that can catalyze polymerization of nucleotides and/or nucleotide analogs. In some embodiments, a polymerase requires the terminal 3' OH of a nucleic acid primer to initiate nucleotide polymerization. In some embodiments, a linker nucleic acid provides a terminal 3'OH for the polymerase to polymerize the nucleotides.

In some embodiments, nucleotide polymerization can occur in a template-dependent manner. In some embodiments, a polymerase can be a high fidelity polymerase. In some embodiments, a polymerase can be a naturally-occurring polymerase, recombinant polymerase, mutant polymerase, variant polymerase, fusion or otherwise engineered polymerase, chemically modified polymerase, synthetic molecules, or analog, derivative or fragment thereof.

In some embodiments, a mutant polymerase comprises substitution, insertion or deletion of one or more amino acids. In some embodiments, a polymerase can include two or more portions of polymerases linked together. In some embodiments, a polymerase can be a fusion protein comprising at least two portions linked to each other, where the first portion comprises a peptide that can catalyze nucleotide polymerization and a second portion comprising a second polypeptide. In some embodiments, a polymerase includes other enzymatic activities, such as for example, 3' to 5' or 5' to 3' exonuclease activity, or strand displacement activity.

In some embodiments, a polymerase can be isolated from a cell, or generated using recombinant DNA technology or chemical synthesis methods. In some embodiments, a polymerase can be expressed in prokaryote, eukaryote, viral, or phage organisms. In some embodiments, a polymerase can be post-translationally modified proteins or fragments thereof.

In some embodiments, a polymerase can be a DNA polymerase and include without limitation bacterial DNA polymerases, eukaryotic DNA polymerases, archaeal DNA polymerases, viral DNA polymerases and phage DNA polymerases.

In some embodiments, a polymerase can be a replicase, DNA-dependent polymerase, primases, RNA-dependent polymerase (including RNA-dependent DNA polymerases such as, for example, reverse transcriptases), a strand-displacement polymerase, a thermo-labile polymerase, or a thermo-stable polymerase. In some embodiments, a polymerase can be any Family A or B type polymerase. Many types of Family A (e.g., *E. coli* Pol I), B (e.g., *E. coli* Pol II), C (e.g., *E. coli* Pol III), D (e.g., Euryarchaeotic Pol II), X (e.g., human Pol beta), and Y (e.g., *E. coli* UmuC/DinB and eukaryotic RAD30/xeroderma pigmentosum variants) polymerases are described in Rothwell and Watsman 2005 Advances in Protein Chemistry 71:401-440. In some embodiments, a polymerase can be a T3, T5, T7, or SP6 RNA polymerase.

These and other polymerases are described by Rothwell and Watsman (2005 Advances in Protein Chemistry 71:401-440). One skilled in the art will know which polymerase(s) to select to conduct a polymerizing, amplifying, nick translating, and/or tailing reaction.

Nucleotides:

Provided herein are nucleotides which comprise mate pair constructs and mate pair libraries. Also provided herein are methods for preparing mate pair constructs and mate pair libraries which can utilize one or more types of nucleotides.

In some embodiments, a first and/or second single-stranded oligonucleotide and/or any blocking oligonucleotide can comprise nucleic acids having natural and/or analog nucleotides. In some embodiments, a nucleotide can be any compound that can bind selectively to, or can be polymerized by, a polymerase. In some embodiments, nucleotides can be polymerized by a polymerase in a primer extension reaction. In some embodiments, a nucleotide can be a naturally-occurring nucleotide, or analog thereof. In some embodiments, a nucleotide comprises a base, sugar and phosphate moieties. In some embodiments, a nucleotide can lack a base, sugar or phosphate moiety. In some embodiments, a nucleotide can include a chain of phosphorus atoms comprising three, four, five, six, seven, eight, nine, ten or more phosphorus atoms. In some embodiments, a phosphorus chain can be attached to any carbon of a sugar ring, such as the 5' carbon. In some embodiments, a phosphorus chain can be linked to the sugar with an intervening O or S. In some embodiments, one or more phosphorus atoms in a phosphorus chain can be part of a phosphate group having P and O. In some embodiments, the phosphorus atoms in the chain can be linked together with intervening O, NH, S, methylene, substituted methylene, ethylene, substituted ethylene, $CNH_2$, $C(O)$, $C(CH_2)$, $CH_2CH_2$, or $C(OH)CH_2R$ (where R can be a 4-pyridine or 1-imidazole). In some embodiments, the phosphorus atoms in the chain can have a side group having O, $BH_3$, or S. In some embodiments, a phosphorus atom having a side group other than O can be a substituted phosphate group. In some embodiments, a nucleotide can be attached to a label (e.g., reporter moiety). In some embodiments, a label can be a fluorophore. In some embodiments, a fluorophore can be attached to the terminal phosphate group (or substitute phosphate group). In some embodiments, a nucleotide can comprise a non-oxygen moiety (e.g., thio- or borano-moieties) that replaces an oxygen moiety that bridges the alpha phosphate and the sugar of the nucleotide, or bridges the alpha and beta phosphates of the nucleotide, or bridges the beta and gamma phosphates of the nucleotide, or between any other two phosphates of the nucleotide, or any combination thereof. In some embodiments, nucleotides can be biotinylated.

In some embodiments, a nucleotide can be joined to a binding partner, such as biotin. For example, a biotin moiety can be joined to a base, sugar or any phosphate group of a nucleotide. Various biotinylated nucleotides are commercially-available (see Jena Bioscience, Germany).

In some embodiments, a nucleotide can be a ribonucleotide, deoxyribonucleotide, ribonucleotide polyphosphate, deoxyribonucleotide polyphosphate, peptide nucleotides, metallonucleosides, phosphonate nucleosides, and modified phosphate-sugar backbone nucleotides, analogs, derivatives, variants or modified versions thereof.

Sequencing Methods:
Next Generation and Single Molecule Sequencing Methods:

Provided herein are mate pair constructs and mate pair libraries that can be sequenced using any sequencing technology, including oligonucleotide probe ligation and detection (e.g., SOLiD™ from Life Technologies, WO 2006/084131), probe-anchor ligation sequencing (e.g., Complete Genomics™ or Polonator™), sequencing-by-synthesis (e.g., Genetic Analyzer and HiSeq™, from Illumina), pyrophosphate sequencing (e.g., Genome Sequencer FLX from 454 Life Sciences), ion-sensitive or semiconductor sequencing (e.g., Personal Genome Machine from Ion Torrent™ Systems, Life Technologies), or single molecule sequencing platforms (e.g., HeliScope™ from Helicos™).

Ion-Sensitive or Semiconductor Sequencing Methods:

Provided herein are mate pair constructs and mate pair libraries that can be sequenced using methods that detect one or more byproducts of nucleotide incorporation. The detection of polymerase extension by detecting physicochemical byproducts of the extension reaction, can include pyrophosphate, hydrogen ion, charge transfer, heat, and the like, as disclosed, for example, in Pourmand et al, Proc. Natl. Acad. Sci., 103: 6466-6470 (2006); Purushothaman et al., IEEE ISCAS, IV-169-172; Rothberg et al, U.S. Patent Publication No. 2009/0026082; Anderson et al, Sensors and Actuators B Chem., 129: 79-86 (2008); Sakata et al., Angew. Chem. 118:2283-2286 (2006); Esfandyapour et al., U.S. Patent Publication No. 2008/01666727; and Sakurai et al., Anal. Chem. 64: 1996-1997 (1992).

Reactions involving the generation and detection of ions are widely performed. The use of direct ion detection methods to monitor the progress of such reactions can simplify many current biological assays. For example, template-dependent nucleic acid synthesis by a polymerase can be monitored by detecting hydrogen ions that are generated as natural byproducts of nucleotide incorporations catalyzed by the polymerase. Ion-sensitive sequencing (also referred to as "pH-based" or "ion-based" nucleic acid sequencing) exploits the direct detection of ionic byproducts, such as hydrogen ions, that are produced as a byproduct of nucleotide incorporation. In one exemplary system for ion-based sequencing, the nucleic acid to be sequenced can be captured in a microwell, and nucleotides can be floated across the well, one at a time, under nucleotide incorporation conditions. The polymerase incorporates the appropriate nucleotide into the growing strand, and the hydrogen ion that is released can change the pH in the solution, which can be detected by an ion sensor. This technique does not require labeling of the nucleotides or expensive optical components, and allows for far more rapid completion of sequencing runs. Examples of such ion-based nucleic acid sequencing methods and platforms include the Ion Torrent PGM™ sequencer (Life Technologies Corporation).

In some embodiments, one or more nucleic acid fragments produced using the methods, systems and kits of the present teachings can be used as a substrate for a biological or chemical reaction that is detected and/or monitored by a sensor including a field-effect transistor (FET). In various embodiments the FET is a chemFET or an NI-ET. A "chemFET" or chemical field-effect transistor, is a type of field effect transistor that acts as a chemical sensor. It is the structural analog of a MOSFET transistor, where the charge on the gate electrode is applied by a chemical process. An "ISFET" or ion-sensitive field-effect transistor, is used for measuring ion concentrations in solution; when the ion concentration (such as H+) changes, the current through the transistor will change accordingly. A detailed theory of operation of an ISFET is given in "Thirty years of ISFETOLOGY: what happened in the past 30 years and what may happen in the next 30 years," P. Bergveld, Sens. Actuators, 88 (2003), pp. 1-20.

In some embodiments, the FET may be a FET array. As used herein, an "array" is a planar arrangement of elements such as sensors or wells. The array may be one or two dimensional. A one dimensional array can be an array having one column (or row) of elements in the first dimension and a plurality of columns (or rows) in the second dimension. The number of columns (or rows) in the first and second dimensions may or may not be the same. The FET or array can comprise 102, 103, 104, 105, 106, 107 or more FETs.

In some embodiments, one or more microfluidic structures can be fabricated above the FET sensor array to provide for containment and/or confinement of a biological or chemical reaction. For example, in one implementation, the microfluidic structure(s) can be configured as one or more wells (or microwells, or reaction chambers, or reaction wells, as the terms are used interchangeably herein) disposed above one or more sensors of the array, such that the one or more sensors over which a given well is disposed detect and measure analyte presence, level, and/or concentration in the given well. In some embodiments, there can be a 1:1 correspondence of FET sensors and reaction wells.

Microwells or reaction chambers are typically hollows or wells having well-defined shapes and volumes which can be manufactured into a substrate and can be fabricated using conventional microfabrication techniques, e.g. as disclosed in the following references: Doering and Nishi, Editors, Handbook of Semiconductor Manufacturing Technology, Second Edition (CRC Press, 2007); Saliterman, Fundamentals of BioMEMS and Medical Microdevices (SPIE Publications, 2006); Elwenspoek et al, Silicon Micromachining (Cambridge University Press, 2004); and the like. Examples of configurations (e.g. spacing, shape and volumes) of microwells or reaction chambers are disclosed in Rothberg et al, U.S. patent publication 2009/0127589; Rothberg et al, U.K. patent application GB24611127.

In some embodiments, the biological or chemical reaction can be performed in a solution or a reaction chamber that is in contact with or capacitively coupled to a FET such as a chemFET or an ISFET. The FET (or chemFET or ISFET) and/or reaction chamber can be an array of FETs or reaction chambers, respectively.

In some embodiments, a biological or chemical reaction can be carried out in a two-dimensional array of reaction chambers, wherein each reaction chamber can be coupled to a FET, and each reaction chamber is no greater than 10 $\mu m^3$ (i.e., 1 pL) in volume. In some embodiments each reaction chamber is no greater than 0.34 pL, 0.096 pL or even 0.012 pL in volume. A reaction chamber can optionally be 22, 32, 42, 52, 62, 72, 82, 92, or 102 square microns in cross-sectional area at the top. Preferably, the array has at least 102, 103, 104, 105, 106, 107, 108, 109, or more reaction chambers. In some embodiments, the reaction chambers can be capacitively coupled to the FETs.

FET arrays as used in various embodiments according to the disclosure can be fabricated according to conventional CMOS fabrications techniques, as well as modified CMOS fabrication techniques and other semiconductor fabrication techniques beyond those conventionally employed in CMOS fabrication. Additionally, various lithography techniques can be employed as part of an array fabrication process.

Exemplary FET arrays suitable for use in the disclosed methods, as well as microwells and attendant fluidics, and methods for manufacturing them, are disclosed, for example, in U.S. Patent Publication No. 20100301398; U.S. Patent Publication No. 20100300895; U.S. Patent Publication No. 20100300559; U.S. Patent Publication No. 20100197507, U.S. Patent Publication No. 20100137143; U.S. Patent Publication No. 20090127589; and U.S. Patent Publication No. 20090026082, which are incorporated by reference in their entireties. Examples of an array can include Ion Torrent™ System arrays, such as the 314™, 316™ and 318™ Chips (Life Technologies) used in conjunction with an Ion Torrent™ PGM Sequencer (Life Technologies, Part No. 4462917).

In one aspect, the disclosed methods, compositions, systems, apparatuses and kits can be used for carrying out label-free nucleic acid sequencing, and in particular, ion-based nucleic acid sequencing. The concept of label-free detection of nucleotide incorporation has been described in the literature, including the following references that are incorporated by reference: Rothberg et al, U.S. patent publication 2009/0026082; Anderson et al, Sensors and Actuators B Chem., 129: 79-86 (2008); and Pourmand et al, Proc. Natl. Acad. Sci., 103: 6466-6470 (2006). Briefly, in nucleic acid sequencing applications, nucleotide incorporations are determined by measuring natural byproducts of polymerase-catalyzed extension reactions, including hydrogen ions, polyphosphates, PPi, and Pi (e.g., in the presence of pyrophosphatase).

In some embodiments, the disclosure relates generally to methods for preparing mate pair constructs or mate pair libraries that can be sequenced using hydrogen ion-sensitive sequencing methods. In one exemplary embodiment, the disclosure relates generally to a method for preparing mate pair constructs or mate pair libraries, comprising: (a) providing a first and a second double-stranded oligonucleotide adaptor each having (i) a first and a second single-stranded oligonucleotide annealed together to form a duplex having an overhang portion and (ii) a third single-stranded oligonucleotide annealed to the overhang portion, wherein the overhang portion of the first and second double-stranded oligonucleotide adaptors are capable of annealing with each other, and wherein for the first and a second double-stranded oligonucleotide adaptors the end of the duplex having the overhang portion forms an adaptor-joining end and the other end of the duplex forms a target-joining end; (b) joining the target-joining end of the first double-stranded oligonucleotide adaptor to a first end of the linear double-stranded polynucleotide of interest; (c) joining the target-joining end of the second double-stranded oligonucleotide adaptor to a second end of the linear double-stranded polynucleotide of interest; (d) removing the third single-stranded oligonucleotide from the first and the second double-stranded oligonucleotide adaptors so as to expose the overhang portions of the adaptor-joining ends; (e) annealing the overhang portions of the adaptor-joining ends thereby forming a circular polynucleotide of interest, wherein the circular polynucleotide of interest comprises at least one nick at a junction between the adaptor-joining ends of the first and the second double-stranded oligonucleotide adaptors; (f) performing a nick translation reaction on the at least first nick to move the nick to a new position within the polynucleotide of interest; (g) performing an exonuclease reaction so as to remove at least a portion of the strand having the nick, so as to open the nick into a gap; and (h) cleaving the strand opposite the gap so as to release a linear mate pair construct.

In some embodiments, the mate pair constructs or mate pair library can be sequenced using an ion-sensitive sequencing method. In some embodiments, the sequencing method is performed by incorporating one or more nucleotides in a template-dependent fashion into a newly synthesized nucleic acid strand.

Optionally, the methods can further include producing one or more ionic byproducts of such nucleotide incorporation.

In some embodiments, the methods can further include detecting the incorporation of the one or more nucleotides into the sequencing primer. Optionally, the detecting can include detecting the release of hydrogen ions.

In another embodiment, the disclosure relates generally to a method for sequencing a nucleic acid, comprising: (a)

producing mate pair constructs or mate pair libraries according to the methods disclosed herein; (b) disposing a plurality of mate pair constructs or mate pair libraries into a plurality of reaction chambers, wherein one or more of the reaction chambers are in contact with a field effect transistor (FET). Optionally, the method further includes contacting at least one of the mate pair constructs disposed into one of the reaction chambers with a polymerase, thereby synthesizing a new nucleic acid strand by sequentially incorporating one or more nucleotides into a nucleic acid molecule. Optionally, the method further includes generating one or more hydrogen ions as a byproduct of such nucleotide incorporation. Optionally, the method further includes detecting the incorporation of the one or more nucleotides by detecting the generation of the one or more hydrogen ions using the FET.

In some embodiments, the detecting includes detecting a change in voltage and/or current at the at least one FET within the array in response to the generation of the one or more hydrogen ions.

In some embodiments, the FET can be selected from the group consisting of: ion-sensitive FET (is FET) and chemically-sensitive FET (chemFET).

One exemplary system involving sequencing via detection of ionic byproducts of nucleotide incorporation is the Ion Torrent PGM™ sequencer (Life Technologies), which is an ion-based sequencing system that sequences nucleic acid templates by detecting hydrogen ions produced as a byproduct of nucleotide incorporation. Typically, hydrogen ions are released as byproducts of nucleotide incorporations occurring during template-dependent nucleic acid synthesis by a polymerase. The Ion Torrent PGM™ sequencer detects the nucleotide incorporations by detecting the hydrogen ion byproducts of the nucleotide incorporations. The Ion Torrent PGM™ sequencer can include a plurality of nucleic acid templates to be sequenced, each template disposed within a respective sequencing reaction well in an array. The wells of the array can each be coupled to at least one ion sensor that can detect the release of FE ions or changes in solution pH produced as a byproduct of nucleotide incorporation. The ion sensor comprises a field effect transistor (FET) coupled to an ion-sensitive detection layer that can sense the presence of $H^+$ ions or changes in solution pH. The ion sensor can provide output signals indicative of nucleotide incorporation which can be represented as voltage changes whose magnitude correlates with the $H^+$ ion concentration in a respective well or reaction chamber. Different nucleotide types can be flowed serially into the reaction chamber, and can be incorporated by the polymerase into an extending primer (or polymerization site) in an order determined by the sequence of the template. Each nucleotide incorporation can be accompanied by the release of $H^+$ ions in the reaction well, along with a concomitant change in the localized pH. The release of $H^+$ ions can be registered by the FET of the sensor, which produces signals indicating the occurrence of the nucleotide incorporation. Nucleotides that are not incorporated during a particular nucleotide flow may not produce signals. The amplitude of the signals from the FET can also be correlated with the number of nucleotides of a particular type incorporated into the extending nucleic acid molecule thereby permitting homopolymer regions to be resolved. Thus, during a run of the sequencer multiple nucleotide flows into the reaction chamber along with incorporation monitoring across a multiplicity of wells or reaction chambers can permit the instrument to resolve the sequence of many nucleic acid templates simultaneously. Further details regarding the compositions, design and operation of the Ion Torrent PGM™ sequencer can be found, for example, in U.S. patent application Ser. No. 12/002,781, now published as U.S. Patent Publication No. 2009/0026082; U.S. patent application Ser. No. 12/474,897, now published as U.S. Patent Publication No. 2010/0137143; and U.S. patent application Ser. No. 12/492,844, now published as U.S. Patent Publication No. 2010/0282617, all of which applications are incorporated by reference herein in their entireties.

In some embodiments, the disclosure relates generally to use of mate pair constructs or mate pair libraries produced using any of the methods, systems and kits of the present disclosure in methods of ion-based sequencing. Use of such mate pair constructs or mate pair libraries in ion-based sequencing reactions can be advantageous because the methods of the disclosure permit isolation of polynucleotides (e.g., tags) of a desired size that can be selected to match the read length capacity of the ion-based sequencing system.

In a typical embodiment of ion-based nucleic acid sequencing, nucleotide incorporations can be detected by detecting the presence and/or concentration of hydrogen ions generated by polymerase-catalyzed extension reactions. In one embodiment, templates each having a primer and polymerase operably bound can be loaded into reaction chambers (such as the microwells disclosed in Rothberg et al, cited herein), after which repeated cycles of nucleotide addition and washing can be carried out. In some embodiments, such templates can be attached as clonal populations to a solid support, such as a particle, bead, or the like, and said clonal populations are loaded into reaction chambers. As used herein, "operably bound" means that a primer is annealed to a template so that the primer's 3' end may be extended by a polymerase and that a polymerase is bound to such primer-template duplex, or in close proximity thereof so that binding and/or extension takes place whenever nucleotides are added.

In each addition step of the cycle, the polymerase can extend the primer by incorporating added nucleotide only if the next base in the template is the complement of the added nucleotide. If there is one complementary base, there is one incorporation, if two, there are two incorporations, if three, there are three incorporations, and so on. With each such incorporation there is a hydrogen ion released, and collectively a population of templates releasing hydrogen ions changes the local pH of the reaction chamber. The production of hydrogen ions is monotonically related to the number of contiguous complementary bases in the template (as well as the total number of template molecules with primer and polymerase that participate in an extension reaction). Thus, when there are a number of contiguous identical complementary bases in the template (i.e. a homopolymer region), the number of hydrogen ions generated, and therefore the magnitude of the local pH change, can be proportional to the number of contiguous identical complementary bases. If the next base in the template is not complementary to the added nucleotide, then no incorporation occurs and no hydrogen ion is released. In some embodiments, after each step of adding a nucleotide, an additional step can be performed, in which an unbuffered wash solution at a predetermined pH is used to remove the nucleotide of the previous step in order to prevent misincorporations in later cycles. In some embodiments, the after each step of adding a nucleotide, an additional step can be performed wherein the reaction chambers are treated with a nucleotide-destroying agent, such as apyrase, to eliminate any residual nucleotides remaining in the chamber, which may result in spurious extensions in subsequent cycles.

In one exemplary embodiment, different kinds of nucleotides are added sequentially to the reaction chambers, so that each reaction can be exposed to the different nucleotides one at a time. For example, nucleotides can be added in the following sequence: dATP, dCTP, dGTP, dTTP, dATP, dCTP, dGTP, dTTP, and so on; with each exposure followed by a wash step. The cycles may be repeated for 50 times, 100 times, 200 times, 300 times, 400 times, 500 times, 750 times, or more, depending on the length of sequence information desired.

In some embodiments, sequencing can be performed with an Ion Torrent™ PGM™ sequencer. For example, mate pair constructs prepared as disclosed herein can be clonally amplified on Ion Sphere™ Particles as part of the Ion Xpress™ Template Kit (Life Technologies Part No. 4469001). Template preparation can be performed essentially accordingly to the protocols provided in the Ion Xpress™ Template Kit v2.0 User Guide (Life Technologies, Part No. 4469004). The amplified DNA can then be sequenced on the Ion PGM™ sequencer (Ion Torrent™, Life Technologies, Part No. 4462917) essentially according to the protocols provided in the Ion Sequencing Kit v2.0 User Guide (Ion Torrent™, Life Technologies, Part No. 4469714) and using the reagents provided in the Ion Sequencing Kit (Ion Torrent™, Life Technologies, Part No. 4468997) and the Ion 314™ Chip Kit (Ion Torrent™, Life Technologies, Part No. 4462923).

Systems:

Provided herein are systems comprising a blocking oligonucleotide adaptors which include (a) a first single-stranded oligonucleotide annealed to a second single-stranded oligonucleotide to form a duplex having an overhang portion and (b) a third single-stranded oligonucleotide (blocking oligonucleotide) annealed to the overhang portion, where the end of the duplex having the overhang portion forms a adaptor-joining end and the other end of the duplex forms a target-joining end. The overhang portion can be exposed by removal of the third single-stranded oligonucleotide. In some embodiments, systems further comprise one or more polynucleotides of interest for joining to one or more blocking oligonucleotide adaptors. In some embodiments, a first and/or second single-stranded oligonucleotide can include a binding partner moiety (e.g., biotin). In some embodiments, the overhang portion of the first and second blocking oligonucleotide adaptors can be capable of annealing with each other. In some embodiments, a system comprises a pair of blocking oligonucleotide adaptors.

Provided herein are systems, comprising linear polynucleotide constructs having a linear polynucleotide of interest joined at one or both ends with a blocking oligonucleotide adaptor. Blocking oligonucleotide adaptors can comprise: (a) a first single-stranded oligonucleotide annealed to a second single-stranded oligonucleotide to form a duplex having an overhang portion and (b) a third single-stranded oligonucleotide (blocking oligonucleotide) annealed to the overhang portion, where the end of the duplex having the overhang portion forms a adaptor-joining end and the other end of the duplex forms a target-joining end. In some embodiments, the overhang portion of the first and second blocking oligonucleotide adaptors can be capable of annealing with each other. In some embodiments, the third single-stranded oligonucleotide (blocking oligonucleotide) of the first and second blocking oligonucleotide adaptors can be removed to expose the overhang portions. In some embodiments, a first and/or second single-stranded oligonucleotide can include a binding partner moiety (e.g., biotin).

Provided herein are systems, comprising linear polynucleotides having each end joined to a blocking oligonucleotide adaptor and circularized. For example, a circular construct includes a linear polynucleotide of interest joined at a first end with a target-joining end of a first blocking oligonucleotide adaptor and joined at a second end with a target-joining end of a second blocking oligonucleotide adaptor. The first and second blocking oligonucleotide adaptors comprise: (a) a first single-stranded oligonucleotide annealed to a second single-stranded oligonucleotide to form a duplex having an overhang portion and (b) a third single-stranded oligonucleotide (blocking oligonucleotide) annealed to the overhang portion, where the end of the duplex having the overhang portion forms a adaptor-joining end and the other end of the duplex forms a target-joining end. In some embodiments, the overhang portion of the first and second blocking oligonucleotide adaptors can be capable of annealing with each other. In some embodiments, the third single-stranded oligonucleotide (or a single-stranded portion of an oligonucleotide) can be removed from the overhang portions of the first and second oligonucleotide adaptors so as to expose the overhang portions of the adaptor-joining ends. In some embodiments, the exposed overhang ends of two blocking oligonucleotide adaptors can be annealed together, thereby joining together the adaptor-joining ends of the first and second blocking oligonucleotide adaptors so as to generate a circularized construct. In some embodiments, one or both polynucleotide strands at the junction between the adaptor-joining ends of the first and second adaptors can include a nick or gap. In some embodiments, a first and/or second single-stranded oligonucleotide can include a binding partner moiety (e.g., biotin).

Kits

Provided herein are kits comprising reagents for conducting methods for joining together one or more ends of polynucleotides of interest to blocking oligonucleotide adaptors, for preparing mate pair constructs and/or for preparing mate pair libraries having blocking oligonucleotide adaptors. In some embodiments, kits can include any combination of: one or more types of blocking oligonucleotide adaptors (with or without biotin) (FIGS. 1A and B-7); reagents for fragmenting a polynucleotide of interest; reagents for end-repairing the ends of the fragments of a polynucleotide of interest; reagents for size-selecting nucleic acids; reagents for joining one or both ends of a fragment of a polynucleotide of interest to one or more types of adaptors (e.g., blocking oligonucleotide adaptors or additional types of adaptors); reagents for circularizing a linear polynucleotide of interest joined to one or more blocking oligonucleotide adaptors; reagents for performing a nick translation reaction or exonuclease digestion reaction or strand extension reaction; reagents for releasing a linear mate pair construct; reagents to perform a tailing reaction; reagents for purifying a polynucleotide of interest (e.g., as a mate pair construct); reagents for quantifying nucleic acids; reagents for amplifying nucleic acids and/or reagents for sequencing nucleic acids. In some embodiments, the kits can include a set of instructions and genome assembly guides can be included. Such material can be, for example, in print or in digital form. In some embodiments, the kits can include any combination of: various enzymes to conduct reactions such as ligating, end-repairing, size-selecting, adaptor-joining, circularizing, nick-translating, degrading linear nucleic acids; releasing a mate-pair, tailing, and amplifying; beads for nucleic acid capture; reagents for washing; reagents for PCR amplification; adaptors (e.g., P1, P2, A, blocking oligonucleotide adaptors); PCR primers; nucleic acid purification columns; and/or components for nucleic acid gel extraction. In some embodiments, the kits include one or more adaptors having identification sequences (e.g., barcodes).

Embodiments of the present teachings can be further understood in light of the following examples, which should not be construed as limiting the scope of the present teachings in any way.

Example 1

Provided herein is one method for preparing the DNA to be ligated to the blocking oligonucleotide adaptors.

5 ug of genomic DNA was added to a final volume of 125 ul in H$_2$O or TE. The DNA was sheared via Hydroshear. After shearing, the DNA concentration was confirmed with QUBIT. The expected recovery is about 75%. The DNA was purified with a PURELINK column. Use the B2 buffer with 55% isopropanol. The DNA was eluted in 50 ul of E1. The DNA was loaded and eluted a second time. The DNA yield was about 3.2 ug as measured by QUIBIT. The DNA was size-selected on a 1% agarose gel. The DNA was extracted with a QUICK GEL EXTRACTION KIT. The gel slice was about 0.6 ml. The DNA was extracted using 2 QUICK GEL EXTRACTION COLUMNS, eluted in 50 ul of E5 per column. For a 2-3 kb insert library, the DNA yield was about 1.3 ug as measured by QUIBIT.

The DNA was end-polished: DNA in 100 ul; 30 ul 5× End polishing buffer; 3.75 ul of 10 mM dNTPs; 4.5 ul of End polishing enzyme 1; 12 ul End polishing enzyme 2; incubated at room temperature for 30 minutes.

The DNA was purified with a PURELINK column, using B2 buffer with 55% isopropanol. The DNA was eluted 50 ul of E1. The DNA was loaded and eluted a second time. The DNA yield was about 1.2 ug as measured by QUIBIT. The DNA is now ready for ligating to the blocking oligonucleotide adaptors.

Example 2

Provided herein are methods for circularizing a polynucleotide of interest, and constructing a long mate pair library using blocking oligonucleotide adaptors having non-palindrome sequences.

Shearing DNA

1 Kb-3 Kb of DNA was sheared using the COVAIS S2 System or Hydroshear DNA Shearing Device. A speed-vac was used to reduce the volume for the size selection procedure. The sheared DNA was size-selected on a 1% agarose gel prepared in 1×TAE buffer with 10 µL of 1:10,000 SYBR SAFE gel stain per 100 mL volume.

Size-Selecting the DNA

Gel slices containing the desired DNA was cut from the gel. The gel slices were weighed in either 2 mL (gel mass of 400 mg or less) or 15 mL (gel mass from 400 mg to 3,750 mg) tubes, depending on the estimated volume. Assumption: every mg of gel mass equals 1 µL of volume when dissolved. This assumption was used to add 3× volumes of Gel Solubilization Buffer (L3) (Invitrogen, catalog #K2100-12) to the tube containing the gel slices. The gel slices were dissolved by shaking/vortexing the tube at room temperature until the gel slices dissolved completely (~15 minutes). Dissolving the gel slice at temperatures higher than room temperature (e.g., 50° C.) will denature the DNA and cause heteroduplex formation. The gel slices were dissolved in 1-gel volume of isopropanol. For example, 10 of isopropanol was added to 10 mg of gel and mixed well. The dissolved gel mixture was applied to a Quick Gel Extraction column(s) in WashTube(s) (Invitrogen, catalog #K2100-12). One column was used per 400 mg agarose or less than 2000 µL of dissolved gel mixture was loaded per column. More columns were used when necessary. The column was centrifuged at >12,000×G for 1 minute, and the flow-though was discarded. The column was placed back on the Wash Tube(s). 500 µL of Wash Buffer (W1) with ethanol was flowed through the Quick Gel Extraction column(s). The columns were centrifuged at >12,000×G for 1 minute, and the flow-through was discarded. The Quick Gel Extraction columns were centrifuged again at maximum speed for 2 minutes to remove any residual Wash Buffer. The Quick Gel Extraction columns were transferred to clean 1.5-mL LOBIND tubes (Eppendorf, catalog #0030 108.035). The DNA was eluted from the Quick Gel Extraction columns with 50 µL of Elution Buffer (E1). The columns were rested for 1 minute at room temperature. For large fragments, the time was increased to 10 minutes for increased yield. The DNA was eluted from the column by centrifugation at >12,000×G for 1 minute. The eluate in the 1.5-mL LOBIND contained the purified DNA. The eluate was flowed through Quick Gel Extraction columns, then rested for 1 minute at room temperature. The columns were centrifuge at >12,000×g for 1 minute. The DNA yield was quantitated using QUIBIT (Invitrogen, catalog #Q32861).

End-Repair the Size Selected DNA

The size-selected DNA was mixed in a LOBIND 1.5 mL tube or a PCR tube as listed in Table 3. The mixture was incubated at room temperature (20 to 25° C.) for 30 minutes, and heat-killed at 75° C. for 30 minutes, and iced.

TABLE 3

| Component | Concentration | Volume |
| --- | --- | --- |
| Water |  | 17.0 |
| T4 DNA Ligase Buffer | 5X | 20 |
| dNTP | 10 mM | 4.0 |
| T4 Polynucleotide Kinase | 10 U/uL | 4 |
| T4 DNA Polymerase | 5 U/uL | 5 |
| Post-SS DNA |  | 50 |
| Total Reaction Volume (ul) |  | 100 |

Pre-Assembly of the Blocking Oligonucleotide Adaptors

The right (R) and left (L) adaptors were biotinylated and included the following sequences:

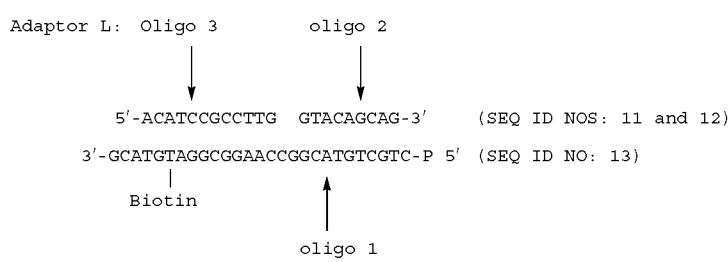

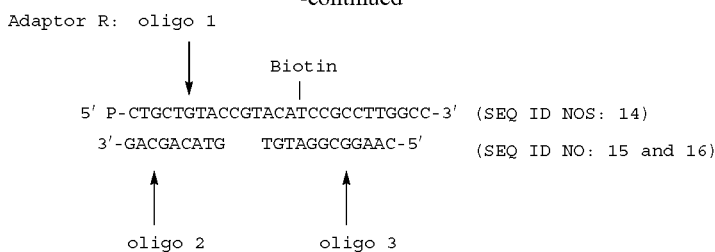

(SEQ ID NOS: 14)
(SEQ ID NO: 15 and 16)

100 ul of 25 uM of the left/right adaptor was prepared by mixing the first and second single-stranded oligonucleotides, and the blocking oligonucleotide as follows:
- 20 ul first ss-oligonucleotide (125 uM)
- 30 ul third ss-oligonucleotide (125 uM)
- 20 ul second ss-oligonucleotide (125 uM)
- 10 ul water
- 20 ul 5× ligase buffer A 100 ul of 25 uM of the left/right adaptor was prepared by mixing the first and second single-stranded oligonucleotides and the blocking oligonucleotide as follows:
- 20 ul first ss-oligonucleotide (125 uM)
- 30 ul third ss-oligonucleotide (125 um)
- 20 ul second ss-oligonucleotide (125 um)
- 10 ul water
- 20 ul 5× ligase buffer Annealing was conducted in a thermocycler.

Ligating Insert DNA to the Adaptors

The amount of adaptor needed for the ligation reaction was calculated based on the amount of the DNA from the End Repair step.

$X$ pmol/ug DNA=1 ug DNA×[($10^6$ pg)/(1 ug)]×[(1 pmol)/(660 pg)]×[1/(average insert size)].

$Y$ ul adapter needed=#ug DNA×[($X$ pmol)/(1 ug DNA)]×100×[(1 ul adaptor needed)/(50 pmol)].

For example:
For 12 ug of purified end-repaired DNA with an average insert size of 1.5 kb $X$ pmol/ug DNA = 1 ug DNA × [$10^6$ pg/1 ug] × [1 pmol/660 pg] × [1/1500] = 1.0 pmol/ug DNA $Y$ uL adaptor needed = 12 ug DNA × [1.0 pmol/1 ug DNA] × 100 × [1 uL adaptor needed/50 pmol]
= 24 uL adaptor needed The ligation reaction was set up as shown in Table 4 below. The ligation reaction was incubated at room temperature (20 to 25° C.) for 30 minutes.

TABLE 4

| Component | Concentration | Volume |
| --- | --- | --- |
| End-Polished DNA |  | 100 |
| T4 DNA Ligase Buffer | 5X | 10 |
| ATP | 25 mM | 6 |
| Adaptor L | 25 uM | x |
| Adaptor R | 25 uM | x |
| T4 DNA Ligase | 5X | 7.5 |
| Water |  | x |
| Total Reaction Volume (ul) |  | 150 |

AMPURE XP Bead Purifying the Ligation Products

One volume of nuclease-free water was added to the sample reaction. 0.8 volumes of AMPURE XP bead mix (Agencourt, catalog #A63880) was added per original volume of DNA sample. The mixture was vortexed and incubated at room temperature for 5 minutes. The tubes were placed on a DYNALMAG rack for 1 minute. The tubes were kept on the magnetic rack. The supernatant was discarded. 600 ul of 70% ethanol was added to the tubes. The tubes were pulse-vortexed thoroughly and pulse spin. The tubes were again placed on a DYNALMAG rack for 1 minute. The supernatant was discarded. Again 600 ul of 70% ethanol was added to the tubes. The tubes were pulse-vortexed thoroughly and pulse spin. The tubes were removed the DYNALMAG rack (Invitrogen) and pulse spin the in a microfuge. The residual supernatant was discarded. The beads were allowed to dry for 3 minutes. The tubes were removed from the DYNALMAG rack and 50 ul of E1 Buffer (Applied Biosystems) was added to the tubes. The tubes were vortexed and incubated at room temperature for 3 minutes or longer. The tubes were placed on the DYNALMAG for 1 minute. The E1 eluate was transferred to a new 1.5 LOBIND tube. 2 µL of the DNA was quantitated by QUIBIT (Invitrogen, catalog #Q32861).

Circularizing the DNA Via Intra Molecular Hybridization

The amount of DNA in the hybridization reaction was calculated to be 0.5 ng/ul. 10× Plasmid-Safe buffer was diluted to 1× in water. The hybridization reaction was set up as shown in Table 5 below.

TABLE 5

| Component | Volume |
| --- | --- |
| DNA Volume (uL) | 50 |
| Plasmid-Safe 1× Buffer | x |
| Total Volume = 0.5 ng/ul of DNA in mix | x |

The hybridization reaction was incubated in a heat block at 70° C. for 5 min, and placed on ice for 30 minutes (typically no more than 1 ml per tube). Large volumes were aliquoted into PCR tubes, 100 ul per tube. The samples were pooled together after cooling.

In an alternative method, the circularization step was conducted in Nick-Translation Buffer. The annealing reaction was incubated in a heat block at 70° C. for 5 min, then placed at 5° C. for 5-30 minutes. At the same time, the DNA pol I and dNTP were incubated at 5° C. The pre-chilled DNA pol I and dNTP were added into circularization mix at the end of incubation. B2-S buffer was added to stop the reaction.

Isolating the Circularized DNA

The circularized DNA was treated with Plasmid-Safe ATP Dependent DNase (Epicentre Biotechnologies) and 25 mM ATP as shown in Table 6 below. The mixture was incubated at 37° C. for 40 minutes.

TABLE 6

| Component | Volume |
| --- | --- |
| Epicentre 25 mM ATP | total vol/1000 * 40 |
| Epicentre Plasmid-Safe Dnase | x/150 |

Purifying the DNA with SOLID Library Micro Column Purification Kit

Empty PURELINK PCR Micro columns (Invitrogen) were pre-spun in collection tubes at 10,000×G for one minute. 4 volumes of PURELINK Binding Buffer (B2-S) with isopropanol was added to 1 volume of sample and mixed well. One PURELING PCR Micro column was used per 4-5 mL of sample in Binding Buffer (B2).

≤700 µL of sample in Binding Buffer (B2) was loaded onto the PURELINK Micro columns in collection tubes. The columns were centrifuged at 10,000×G for 15 seconds except for the last loading. The flow-through was discarded after each spin. After the last loading, the column was spun spin 1 minute. The dsDNA bound to the column. These steps were repeated until the entire sample was loaded onto the columns.

The PURELINK Micro columns were placed back into the same collection tube. 650 µL of Wash Buffer (W1) with ethanol was used to wash the column. The columns were centrifuged at 10,000×G for 1 minute. The flow-through was discarded. The centrifugation was repeated at 14,000×xG to remove residual wash buffer. The columns were transferred to clean 1.5-mL LOBIND tubes. 25 µL of Elution Buffer (E1) was loaded onto to the center of the column to elute the DNA, then the columns were allowed to stand for 1 minute at room temperature. The columns were spun at 14,000×G for 1 minute. The eluate was loaded back onto the column(s), then let the column and allowed to stand for 1 minute at room temperature. The columns were spun at 14,000×G for 1 minute.

In an alternative method, the circularized DNA was purified using AMPURE beads. 0.3× volume of AMPURE beads and 0.7× volume of Bead Buffer (14% PEG8000, 2.5M NaCl) were added to the PLASMIDSAFE DNase-treated circularized DNA. Standard bead capture, wash and elution steps were conducted.

Nick Translating the Circularized DNA

A 0.2-mL LOBIND tube was prepared as shown in Table 7 below.

TABLE 7

| Component | Volume |
| --- | --- |
| DNA Volume After Qubit (uL) | 25 |
| Nuclease-Free Water (uL) | 57 |
| Nick-Translation Buffer | 10 |
| 10 mM dNTPs (uL) | 5 |
| Total Volume (uL) | 97 |

The mixture was pre-incubated without DNA polymerase I at 5° C. in a thermocycler for more than 2 minutes. 3 µL of DNA polymerase I was added to a separate 0.2 mL tube, then pulse-spun. The DNA polymerase I was pre-incubated at 5° C. in a thermocycler for at least 1 minute.

The reaction mix was added to the tube containing the DNA polymerase I and thoroughly mixed. The nick translation reaction was performed using the "no heated lid" feature on the thermocycler for 12 minutes.

400 µL of PURELINK Binding Buffer (B2-S) with isopropanol was added to a 1.5-mL LOBIND tube. At the end of the 12 minutes, the nick translation reaction was immediately transferred to the 1.5-mL LOBIND tube containing Binding Buffer (B2) to denature the enzyme and stop the reaction. The nick-translated DNA was purified using a SOLID Library Micro Column Purification Kit.

T7 Exonuclease Digestion

A T7 exonuclease reaction was set up as shown in Table 8 below. The reaction was incubated at 37° C. for 15 minutes. The enzyme was heat inactivated at 70° C. for 20 minutes. The reaction was chilled on ice for 5 minutes.

TABLE 8

| Components | Volume |
| --- | --- |
| DNA | 25 |
| 10× Buffer 4 | 5 |
| T7 Exonuclease 10 U/uL | 2 |
| Water | 18 |
| Total Volume (ul) | 50 |

S1 Nuclease Digestion

1 µL of S1 Nuclease was freshly diluted to 25 U/mL with S1 Nuclease Dilution Buffer. The S1 nuclease reaction was set up as shown in Table 9 below. The reaction was incubated at 37° C. for 30 minutes.

TABLE 9

| Components | Volume |
| --- | --- |
| DNA | 50 |
| 3M NaCl | 1.67 |
| S1 Nuclease 25 U/uL | 3 |
| Total Volume (ul) | 54.7 |

Alternative DNase and T7 Exonuclease Digestion

The nick-translated DNA was resuspended in PLASMID-SAFE buffer, ATP and PLASMIDSAFE DNase was added to digest the linear DNA fragments (37° C. for 30 minutes). At the end of incubation 20 U of T7 exonuclease was added directly into the reaction mixture and incubate for another 5 minutes. The enzymes were heat inactivated at 70° C. for 20 minutes. The reaction was chilled on ice for 5 minutes.

1 µL of S1 Nuclease was freshly diluted to 25 U/mL with S1 Nuclease Dilution Buffer. The S1 nuclease reaction was set up as shown in Table 9 above. The reaction was incubated at 37° C. for 30 minutes.

A-Tailing Reaction

The A-tailing reaction was set up as shown in Table 10 below.

TABLE 10

| Component | Concentration | Volume |
| --- | --- | --- |
| React 2 Buffer | 10X | 10 |
| dATP | 10 mM | 4 |

TABLE 10-continued

| Component | Concentration | Volume |
|---|---|---|
| dNTPs | 10 mM | 1 |
| Ambion Klenow Exo- | 5 U/uL | 6 |
| Water | | 29 |
| T7/S1-Treated DNA | | 50 |
| Total Volume (ul) | | 100 |

The reaction was incubated at 37° C. for 30 minutes.

The reaction was stopped by mixing compounds as shown in Table 11 below.

TABLE 11

| Component | Volume |
|---|---|
| A-tailed DNA | 100 |
| 0.5M EDTA | 5 |
| Bead Binding Buffer | 200 |
| Nuclease-free Water | 95 |
| Total (ul) | 400 |

DNA Binding to Streptavidin Beads

A 1×BSA solution was prepared. The tube of DYNABEADS MYONE Streptavidin C1 was vortexed, then 50 µL of the beads was transferred into a 1.5-mL LOBIND Tube. 300 µL of Bead Wash Buffer was added to the 90 µL of solution of beads, the beads were vortexed for 15 seconds, then pulse-spun. The tube was placed on a DYNALMAG rack for 1 minute. After the solution appeared clear the supernatant was discarded. 300 µL of 1×BSA was added to the tube and vortexed for 15 seconds, then pulse-spun. The tube was placed on a DYNALMAG rack for 1 minute. After the solution appeared clear the supernatant was discarded. 300 µL of Bead Binding Buffer was added, and the beads were vortexed for 15 seconds, then pulse spun. The tube was placed on a DYNALMAG rack for 1 minute. After the solution appeared clear the supernatant was discarded. The entire 400 µL of solution of library DNA in Bead Binding Buffer was added to the pre-washed streptavidin beads, then vortexed. The solution was rotated at room temperature (20 to 25° C.) for 30 minutes, then pulse spun.

Washing the Bead-DNA Complex

1× Ligase Buffer (total volume=400 ul) was prepared. The tube of bead-DNA complex was placed on a magnetic rack for at least 1 minute. After the solution appeared clear, the supernatant was discarded. The bead-DNA were resuspended in 300 µL of Bead Wash Buffer, then transferred to a new the beads to a new 1.5-mL LOBIND tube. The bead-DNA was vortexed 15 seconds, then pulse-spun. The tube of bead-DNA complex was placed on a magnetic rack for at least 1 minute. After the solution appeared clear, the supernatant was discarded. The bead-DNA was resuspended in 300 µL of Bead Wash Buffer. The bead-DNA was vortexed for 15 seconds, then pulse-spun. The tube of bead-DNA complex was placed on a magnetic rack for at least 1 minute. After the solution appeared clear, the supernatant was discarded. The bead-DNA was resuspended in 300 µL of Bead Wash Buffer. The bead-DNA was vortexed for 15 seconds, then pulse-spun. The tube of bead-DNA complex was placed on a magnetic rack for at least 1 minute. After the solution appeared clear, the supernatant was discarded. The bead-DNA was resuspended in 300 µL of 1× Ligase Buffer. The bead-DNA was vortexed for 15 seconds, then pulse-spun. The tube of bead-DNA complex was placed on a magnetic rack for at least 1 minute. After the solution appeared clear, the supernatant was discarded. The bead-DNA was resuspended in 93 µL of 1× Ligase Buffer.

Ligating the P1 and P2 Adaptors to the DNA

The bead-DNA was prepared for ligation to P1 and P2 adaptors as shown in Table 12 below:

TABLE 12

| Component | Volume |
|---|---|
| DNA-bead complex | 93 |
| P1 Adaptor (ds), 50 µM | 1 |
| P2 Adaptor (ds), 50 µM | 1 |
| T4 DNA Ligase, 5 U/µL | 5 |
| Total Volume (µL) | 100 |

The ligation reaction was incubated at room temperature (20 to 25° C.) on a rotator for 20 minutes. The tube of bead-DNA-P1/P2 complex was placed on a magnetic rack for at least 1 minute. After the solution appeared clear, the supernatant was discarded. The beads were resuspended in 300 µL of Bead Wash Buffer and transferred to a new 1.5-mL LOBIND tube. The beads were vortexed for 15 seconds, then pulse-spun. The tube of bead-DNA-P1/P2 complex was placed on a magnetic rack for at least 1 minute. After the solution appeared clear, the supernatant was discarded. The bead-DNA-P1/P2 complex was resuspended in 300 µL of Bead Wash Buffer. The beads were vortexed for 15 seconds, then pulse-spun. The tube of bead-DNA-P1/P2 complex was placed on a magnetic rack for at least 1 minute. After the solution appeared clear, the supernatant was discarded. The beads were resuspended in 300 µL of Elution Buffer (E1). The tube of bead-DNA-P1/P2 complex was placed on a magnetic rack for at least 1 minute. After the solution appeared clear, the supernatant was discarded. The beads were resuspended in 30 µL of Elution Buffer (E1).

PCR Amplifying the Paired Tag Library

The paired tag library was amplified with a PLATINUM PCR Amplification Mix (Invitrogen). The PLATINUM PCR amplification mix contains a proofreading enzyme for high fidelity amplification. The PCR reaction was set up as shown in Table 13 below:

TABLE 13

| Component | Volume |
|---|---|
| Platinum ® PCR Amplification Mix‡ | 70 |
| Library PCR Primer 1, 50 µM | 1.4 |
| Library PCR Primer 2, 50 µM | 1.4 |
| Total (ul) | 72.8 |

The master mix was vortexed. For a negative control, 23 µL of the PCR master mix was added to a PCR tube. 4 µL of DNA-bead complex solution was added to the remaining 49.8 µL of PCR master mix, vortexed, then divided evenly (~25 mL) between two PCR tubes (tubes #1 and 2). Tube #1: 10 cycles, tube #2 and negative control tube: 14 cycles. The thermocycler settings are shown in Table 14 below.

TABLE 14

| Stage | Step | Temp | Time |
|---|---|---|---|
| Holding | Nick Translation | 72° C. | 20 min |
| Holding | Denature | 94° C. | 3 min |

TABLE 14-continued

| Stage | Step | Temp | Time |
|---|---|---|---|
| Cycling | Denature | 94° C. | 15 sec |
| | Anneal | 62° C. | 15 sec |
| | Extend | 70° C. | 1 min |
| Holding | Extend | 70° C. | 5 min |
| Holding | | 4° C. | ? |

Amplification was confirmed on a pre-case 2% E-GEL EX (Invitrogen). The size of amplified library should be between 275 and 325 bp, but 250 to 350 bp is acceptable. Detailed methods for preparing a mate pair construct and/or mate pair library can be found in "Mate-Pair Library Preparation; 5500 Series SOLiD™ Systems" (from Applied Biosystems, publication part No. 4460958, hereby incorporated by reference in its entirety).

Example 3

This Example illustrates another method of making a paired tag library.

In this Example, a nucleic acid sequence is fragmented to produce a plurality of polynucleotide fragments. The ends of the polynucleotide fragments are end repaired to form blunt-ended polynucleotide fragments. The polynucleotide fragments are then subjected to a size selection method to generate polynucleotides of interest that are the desired size for example, about 10 kb in size. Adaptors are joined to the ends of each size-selected polynucleotide of interest, thereby forming a plurality of adaptor modified polynucleotides of interest. The adaptor modified polynucleotides of interest are ligated to produce a plurality of circular nucleic acid molecules, wherein a nick is introduced between the adaptor and the polynucleotide of interest. A nick translation reaction is performed on the circular nucleic acid molecules to produce a plurality of circular nucleic acid molecules each having at least one nick present within its corresponding polynucleotide fragment. The resulting circular nucleic acid molecules are cleaved at a point opposite a nick to release the paired tags, thereby producing a paired tag library. The paired tag clones can be clonally amplified by, for example, by emulsion PCR, and subsequently sequenced by, for example, Ion Torrent™ PGM Sequencing.

Example 4

This Example illustrates a paired tag library preparation workflow.

In this Example, a nucleic acid sequence is fragmented to form random length polynucleotides. The random length polynucleotides are subjected to a size selection method to remove smaller and/or larger polynucleotides outside the desired length of the polynucleotide of interest. The size selected polynucleotides of interest are modified to have the appropriate end configurations to match one or more adaptors that are ligated to the polynucleotides of interest to form adaptor modified polynucleotides of interest. After ligation, the circularized adaptor modified polynucleotides contain one or more nicks located close to the polynucleotide of interest. The one or more nicks are then extended into the polynucleotide of interest by nick translation. After translation of the nicks, the circular population is then cut at the one or more nick positions, thereby releasing the paired tag, and thereby producing a paired tag library. The paired tag library can be clonally amplified by, for example, by emulsion PCR, and subsequently sequenced by, for example, Ion Torrent™ PGM Sequencing.

Example 5

This example provides another method for the preparation of a long mate-pair library.

Shearing DNA

DNA (1-5 μg DNA for 3 kb insert library or 1-20 μg DNA for 10 kb insert library) was sheared using a HydroShear® DNA Shearing Device (DigiLab, MA) according to the manufacturer's instructions. For 3 kb inserts, DNA was sheared using the HydroShear® standard shearing assembly with a speed code of 13 for 20 cycles. For 10 kb inserts, DNA was sheared using the HydroShear® large shearing assembly with a speed code of 10 for 20 cycles. The final volume of sheared DNA was reduced using a SpeedVac® or concentrator to obtain about 70 μl of sheared DNA for a 3 kb insert library and less than 100 μl for a 10 kb insert library.

End-Repairing the Sheared DNA

The sheared DNA was mixed in a LoBind 1.5 mL tube or a PCR tube as listed in Table 15. The mixture was incubated at room temperature (20 to 25° C.) for 30 minutes.

TABLE 15

| Component | 3 kb library | 10 kb library |
|---|---|---|
| Sheared DNA | ~65 ul | <100 ul |
| 5x Reaction Buffer | 20 ul | 30 ul |
| 10 mM dNTP | 4 ul | 6 ul |
| End Polishing E1 | 4 ul | 6 ul |
| End Polishing E2 | 5 ul | 8 ul |
| Nuclease-free water | Varies | Varies |
| Total | 100 ul | 150 ul |

The following reagents were added to the end repaired DNA solutions:

| Component | 3-kb Library | 10-kb library |
|---|---|---|
| 20% SDS | 8.5 ul | 13 ul |
| 10X BlueJuice ™ Gel Loading Buffer | 10 ul | 16 ul |

The end-repaired DNA was denatured for 10 minutes at 65° C. The samples were placed on ice for 5 minutes and loaded onto wells on an appropriate percent agarose gel in 1×TAE buffer with 20 μL of 10,000×SYBR® Safe gel stain per 200 mL volume. Typically, a 0.6% gel can be used for a 10-kb library and a 1% agarose gel can be used to size select a 3-kb library.

Size-Selecting the DNA

The size-selection step was conducted using a SOLiD™ Library Quick Gel Extraction Kit (Invitrogen Part No. 4443711). Gel slices containing the desired DNA was cut from the gel. For a 3 kb insert library, the gel band was removed from 2.8 kb-3.5 kb from a 1% agarose gel. For a 10 kb insert library, the band was removed from the 10 kb-11 kb size range from a 0.6% agarose gel. The gel slices were weighed in either 1.5 mL Lobind tube (gel mass of 200 mg or less) or 15 mL (gel mass greater than 200 mg) tubes, depending on the estimated volume. A 30 μL volume of Gel Solubilization Buffer (L3) was added for every 10 mg of gel mass to the tube containing the gel slices. The gel slices were dissolved by shaking/vortexing the tube at room temperature until the gel slices dissolved completely (~15 minutes). Dissolving the gel slice at temperatures higher than room temperature (e.g., 50° C.) will denature the DNA and cause heteroduplex formation. The gel slices were dissolved in 1-gel volume of isopropanol. For example, 10 µL of isopropanol was added to 10 mg of gel and mixed well. The dissolved gel mixture was applied to a Quick Gel Extraction column(s). One column was used per 400 mg agarose or less than 2000 µL of dissolved gel mixture. The column was centrifuged at >12,000×G for 1 minute, and the flow-though was discarded. 500 µL of Wash Buffer (W1) with ethanol was flowed through the Quick Gel Extraction column(s). The columns were centrifuged at >12,000×G for 1 minute, and the flow-through was discarded. The Quick Gel Extraction columns were centrifuged again at maximum speed for 2 minutes to remove any residual Wash Buffer. The Quick Gel Extraction columns were transferred to clean 1.5-mL LOBIND tubes (Eppendorf, Catalog No. 0030 108.035). The DNA was eluted from the Quick Gel Extraction columns with 50 µL of Elution Buffer (E5). The columns were rested for 10 minutes at room temperature. The DNA was eluted from the column by centrifugation at >12,000×G for 1 minute. If more than one column was used, the eluate was pooled and reduced in volume with a SpeedVac® or concentrator to a volume less than 60 µl to perform ligation of the mate pair adaptors to the DNA. The DNA yield was quantitated using the QUBIT™ dsDNA HS assay kits (Invitrogen, Catalog No. Q32851) and the Qubit® 2.0 (Invitrogen, Part No. Q32866).

Pre-Assembly of the Blocking Oligonucleotide Adaptors

In this example, left (L) and right (R) adaptors included biotin and included the following sequences. However, in an alternative method non-biotinylated adaptors can be used as blocking adaptors.

Annealing of the blocking adaptors was conducted in a thermocycler. In an alternative method, the left and right adaptors were not pre-assembled and ligated to the size-selected, end-repaired DNA as described in the following step.

Ligating DNA to the Adaptors

The ligation step adds the mate pair adaptors to the sheared, end-repaired DNA. The mate pair adaptors are lacking a 5' phosphate at the non-joining end; as a result, there is a nick on each strand when the DNA is circularized. The amount of adaptor needed for the ligation reaction was calculated based on the amount of the DNA from the size selection step.

$$\text{ug to pmol conversion factor} = (10^6 \text{ pg})/(1 \text{ ug}) \times (1 \text{ pmol})/(660 \text{ pg}) \times 1/(\text{average insert size}).$$

$$Y \text{ ul adapter needed} = \text{\#ug DNA} \times (\text{ug to pmol conversion factor}) \times 50 \times (1 \text{ ul adaptor needed})/(25 \text{ pmol}).$$

For example, 1 ug of purified size-selected DNA with an average insert size of about 3 kb:

$$\text{ug to pmol conversion factor} = (10^6 \text{ pg})/(1 \text{ ug}) \times (1 \text{ pmol})/(660 \text{ pg}) \times 1/(3000) = 0.5 \text{ pmol/µg DNA}$$

$$Y \text{ ul adapter needed} = 1 \text{ ug DNA} \times (0.5 \text{ pmol})/(\text{ug DNA}) \times 50 \times (1 \text{ ul adaptor needed})/(25 \text{ pmol}) = 1 \text{ µl adaptor needed.}$$

The ligation reaction was set up as shown in Table 16 below. The ligation reaction was incubated at room temperature (20 to 25° C.) for 30 minutes.

TABLE 16

| End-repaired DNA | <60 ul |
|---|---|
| 5x Reaction Buffer | 20 ul |
| MPR Adaptor (ds), 25 uM | Y ul |

```
Adaptor L:  Oligo 3        oligo 2
                ↓              ↓
            5'-ACATCCGCCTTG  GTACAGCAG-3'   (SEQ ID NOS: 11 and 12)
            3'-GCATGTAGGCGGAACCGGCATGTCGTC-P 5' (SEQ ID NO: 13)
                    |                    ↑
                  Biotin
                                       oligo 1
Adaptor R:  oligo 1
                ↓              Biotin
                                  |
            5' P-CTGCTGTACCGTACATCCGCCTTGGCC-3'  (SEQ ID NOS: 14)
              3'-GACGACATG    TGTAGGCGGAAC-5'   (SEQ ID NO: 15 and 16)
                    ↑              ↑
                  oligo 2        oligo 3
```

100 µl of 25 µM of the left/right adaptor was prepared by mixing the first and second single-stranded oligonucleotides, and the blocking oligonucleotide as follows:

20 µl first ss-oligonucleotide (125 µM)

30 µl third ss-oligonucleotide (125 µM)

20 µl second ss-oligonucleotide (125 µM)

10 µl water

20 µl 5× ligase buffer

TABLE 16-continued

| MPL Adaptor (ds), 25 um | Y ul |
|---|---|
| T4 DNA ligase, 5U/ul | 10 ul |
| Nuclease-free water | Varies |
| Total | 100 ul |

AMPure® XP Bead Purifying the Ligation Products 1.5× volume of nuclease-free water was added to the sample reaction. 1.6 volumes of AMPure® XP bead mix (Agencourt, Catalog No. A63880) was added per original volume of DNA sample. The mixture was vortexed for 15 seconds, pulse-spin and incubated at room temperature for 5 minutes. The tubes were placed on a DYNALMAG rack for 1 minute until the solution cleared. The supernatant was discarded. 600 ul of freshly prepared 70% ethanol was added to the tube. The tubes were kept on a DYNALMAG rack for at least 1 minute and then the supernatant was discarded. Again 600 ul of freshly prepared 70% ethanol was added to the tubes, left to stand for 1 minute and the residual supernatant was discarded. The tubes were pulse spin, returned to the rack and any residual supernatant was discarded. The beads were allowed to dry for 3 minutes. The tubes were removed from the DYNALMAG rack and 50 ul of E1 Buffer was added to the tubes. The tubes were vortexed and incubated at room temperature for 3 minutes. The tubes were placed on the DYNALMAG for 1 minute until the solution cleared. The E1 eluate was transferred to a new 1.5 LOBIND tube. 1 μL of the DNA sample was quantitated by QUBIT™ dsDNA HS assay kits (Invitrogen, Catalog No. Q32851) and the Qubit® 2.0 Fluorometer (Invitrogen, Part No. Q32866.

Circularizing the DNA Via Intra Molecular Hybridization

The amount of DNA in the hybridization reaction was calculated to a final concentration of 0.5 ng/μl. For example, the total volume of the circularization reaction (T, ul) was calculated for a known concentration of DNA (DNA ng/ul) and a known volume of DNA (V). For example, if the DNA concentration is 5 ng/ul and the V=50 ul, then T=500 ul.

The hybridization reaction was set up as shown in Table 17 below.

TABLE 17

| Component | Volume |
| --- | --- |
| DNA | V ul |
| 10x Plasmid-Safe ™ Buffer | T/10 ul |
| Nuclease-free water | T-(T/10)-V ul |
| Total | T ul |

The hybridization reaction was incubated in a heat block at 70° C. for 5 min, and placed on ice. Large volumes were aliquoted into PCR tubes, 100 ul per tube. The samples were pooled together after cooling.

Isolating the Circularized DNA

The circularized DNA was treated with Plasmid-Safe DNase to eliminate uncircularized DNA (Epicentre Biotechnologies) and 100 mM ATP as shown in Table 18 below. The mixture was incubated at 37° C. for 40 minutes.

TABLE 18

| Component | Volume |
| --- | --- |
| DNA | T ul |
| ATP, 100 mM | T/100 ul |
| Plasmid-Safe ™ DNase, 10 u/ul | T/100 ul |
| Total | T ul |

Based on the above, if T=800 μl, then ATP (100 mM) is 8 μl and Plasmid-Safe DNase (10 u/μl) is 8 μl.

Purifying the Circularized DNA with AMPure® XP Beads

The bead suspension reaction was set up as follows:
Sample reaction=T μl
Bead dilution buffer=0.7×T μl
Agencourt AMPure® XP Reagent=0.3×T μl The mixture was vortexed for 15 seconds, pulse-spin and incubated at room temperature for 5 minutes. The tubes were placed on a DYNALMAG rack for 1 minute until the solution cleared. The supernatant was discarded. 600 ul of freshly prepared 70% ethanol was added to the tube. The tubes were kept on a DYNALMAG rack for at least 1 minute and then the supernatant was discarded. Again 600 ul of freshly prepared 70% ethanol was added to the tubes, left to stand for 1 minute and the residual supernatant was discarded. The tubes were pulse spin, returned to the rack and any residual supernatant was discarded. The beads were allowed to dry for 3 minutes. The tubes containing the dried sample were resuspended in 94 μl of a pre-mixed solution (containing 84 μl nuclease-free water and 10 μl of Nick Translation Buffer (E1)). The tubes were gently vortexed for 15 seconds, pulse-spin and incubated at room temperature for 3 minutes. The tubes were placed on the DYNALMAG for 1 minute until the solution cleared. The supernatant was transferred to a new 1.5 LOBIND tube. Optionally, 1 μL of the DNA sample was quantitated by QUBIT™ dsDNA HS assay kits (Invitrogen, Catalog No. Q32851) and the Qubit® 2.0 Fluorometer (Invitrogen, Part No. Q32866).

Nick Translating the Circularized DNA

Nick translation using *E. coli* DNA polymerase I translates the nick into the genomic DNA region. The size of the mate-paired tags to be produced can be controlled by adjusting the reaction time and temperature.

A 0.2-mL LOBIND tube was prepared as shown in Table 19 below.

TABLE 19

| Component | Volume |
| --- | --- |
| DNase treated, purified DNA | ~90 ul |
| 10 mM dNTP | 5 ul |

The mixture was pre-incubated without DNA polymerase I at 5° C. in a thermocycler for 2-3 minutes. 5 μL of DNA polymerase I was added to a separate 0.2 mL tube, then pulse-spun. The DNA polymerase I was pre-incubated at 5° C. in a thermocycler for at least 1 minute.

The reaction mix was added to the tube containing the DNA polymerase I and thoroughly mixed. The nick translation reaction was performed using the "no heated lid" feature on the thermocycler for 10 minutes.

400 μL of PURELINK Binding Buffer (B2-S) with isopropanol was added to a 1.5-mL LOBIND tube. At the end of the incubation, the nick translation reaction was immediately transferred to the 1.5-mL LOBIND tube containing Binding Buffer (B2-S) to denature the enzyme and stop the reaction. The nick-translated DNA was purified using a SOLiD Library Micro Column Purification Kit (Life Technologies) essentially according to the manufacturer's instructions. The purified DNA in elution buffer (E1) was stored at 4° C. or directly digested with T7 Exonuclease and S1 nuclease.

T7 Exonuclease Digestion

T7 exonuclease recognizes nicks within the circularized DNA. The 5'-3' exonuclease activity digests the unligated strand away from the mate-pair tags creating a gap in the sequence. This gap creates an exposed single-stranded region that is more easily recognized by S1 nuclease. A T7 exonuclease reaction was set up as shown in Table 20 below. The reaction was incubated at 37° C. for 15 minutes. The enzyme was heat inactivated at 70° C. for 20 minutes. The reaction was chilled on ice for 5 minutes.

TABLE 20

| Components | Volume |
|---|---|
| DNA | 25 |
| 10X Buffer 4 | 5 |
| T7 Exonuclease 10 U/uL | 2 |
| Water | 18 |
| Total Volume (ul) | 50 |

S1 Nuclease Digestion

1 µL of S1 Nuclease was freshly diluted to 50 U/µL with S1 Nuclease Dilution Buffer. The S1 nuclease reaction was set up as shown in Table 21 below. The reaction was incubated at 37° C. for 45 minutes.

TABLE 21

| Components | Volume |
|---|---|
| DNA | 50 |
| 3M NaCl | 1.7 |
| S1 Nuclease 50 U/uL | 2 |
| Total Volume (ul) | 53.7 |

The digested DNA was then purified using the Agencourt AMPure® XP Reagent. The bead suspension reaction was set up as follows:

Sample reaction=53 µl
Agencourt AMPure® XP Reagent=95 µl
Total=148 µl.

The mixture was vortexed for 15 seconds, pulse-spin and incubated at room temperature for 5 minutes. The tubes were placed on a DYNALMAG rack for 1 minute until the solution cleared. The supernatant was discarded. 600 ul of freshly prepared 70% ethanol was added to the tube. The tubes were kept on a DYNALMAG rack for at least 1 minute and then the supernatant was discarded. Again 600 ul of freshly prepared 70% ethanol was added to the tubes, left to stand for 1 minute and the residual supernatant was discarded. The tubes were pulse spin, returned to the rack and any residual supernatant was discarded. The beads were allowed to dry for 3 minutes. The tubes were removed from the DYNALMAG and 50 µl of Elution buffer (E1) was added to each tube. The mixture was vortexed for 15 seconds, pulse-spin and incubated at room temperature for at least 3 minutes. The tubes were placed on a DYNALMAG rack for at least 1 minute until the solution cleared. The supernatant was transferred to a new 1.5 LOBIND tube.

Alternative Method for DNase and T7 Exonuclease Digestion

The nick-translated DNA was resuspended in PLASMID-SAFE buffer, ATP and PLASMIDSAFE DNase was added to digest the linear DNA fragments (37° C. for 30 minutes). At the end of incubation 20 U of T7 exonuclease was added directly into the reaction mixture and incubate for another 5 minutes. The enzymes were heat inactivated at 70° C. for 20 minutes. The reaction was chilled on ice for 5 minutes.

1 µL of S1 Nuclease was freshly diluted to 25 U/mL with S1 Nuclease Dilution Buffer. The S1 nuclease reaction was set up as shown in Table 21 above. The reaction was incubated at 37° C. for 30 minutes At this point, the reaction mixture contains the linear mate pair library. Various other steps can be included by the user to further modify the linear mate pair library such as: adding a dA-tail to the digested DNA, binding the library molecules to streptavidin beads, ligating P1, P2 or A adaptors to the DNA, nick-translating the amplifying the mate pair library, or evaluating the library for example using a High Sensitivity DNA Chip (Agilent). The above additional steps can be performed for example as outlined in Example 6 of this application. In one embodiment, the evaluated mate pair library can be clonally amplified using an Ion Xpress™ Template Kit (Life Technologies Part No. 4469001) essentially accordingly to the protocols provided in the Ion Xpress™ Template Kit v2.0 User Guide (Life Technologies, Part No. 4469004), hereby incorporated by reference in their entirety. The amplified DNA can then be sequenced on the Ion PGM™ sequencer (Ion Torrent™, Life Technologies, Part No. 4462917) essentially according to the protocols provided in the Ion Sequencing Kit v2.0 User Guide (Ion Torrent™, Life Technologies, Part No. 4469714), hereby incorporated by reference in its entirety, and using the reagents provided in the Ion Sequencing Kit (Ion Torrent™, Life Technologies, Part No. 4468997) and the Ion 314™ Chip Kit (Ion Torrent™, Life Technologies, Part No. 4462923), both of which are hereby incorporated in their entirety.

Example 6

The linear mate pair library prepared according to Example 5 can be further processed to end-repair the T7/S1 digested DNA. An end-repair reaction was set up as shown in Table 22 below. The reaction was incubated at room temperature for 30 minutes.

TABLE 22

| T7/S1 digested DNA | 50 ul |
|---|---|
| 5x Reaction Buffer | 20 ul |
| 10 mM dNTP mix | 2 ul |
| End Polishing Enzyme 2 | 2 ul |
| Nuclease-free water | 26 ul |
| Total | 100 ul |

After incubation, 5.0 µl of 0.5 M EDTA was added to stop the reaction.

The sample volume (105 µl of stopped end-repair mix) was added to 200 µl bead binding buffer and with 95 µl nuclease-free water to bring the total volume to 400 µl.

DNA Binding to Streptavidin Beads

Dynabeads® MyOne™ Streptavidin C1 specifically binds to the biotin-labeled mate pair adaptor in the library molecules to purify the library from side products. The beads were pre-washed with a 1×BSA solution.

The tube of DYNABEADS MYONE Streptavidin C1 was vortexed, then 50 µL of the beads was transferred into a 1.5-mL LOBIND Tube. 500 µL of Bead Wash Buffer was added to the 50 µL of solution of beads, the beads were vortexed for 15 seconds, then pulse-spun. The tube was placed on a DYNALMAG rack for 1 minute. After the solution appeared clear the supernatant was discarded. 500 µL of 1×BSA was added to the tube and vortexed for 15 seconds, then pulse-spun. The tube was placed on a DYNALMAG rack for 1 minute. After the solution appeared clear the supernatant was discarded. 500 µL of Bead Binding Buffer was added, and the beads were vortexed for 15 seconds, then pulse spun. The tube was placed on a DYNALMAG rack for 1 minute. After the solution appeared clear the supernatant was discarded. The entire 400 µL of sample containing the library DNA in Bead Binding Buffer was added to the pre-washed streptavidin beads, then vortexed for 15 seconds. The solution was rotated at room temperature (20 to 25° C.) for 30 minutes, then pulse spun.

Washing the Bead-DNA Complex

1× Reaction Buffer (total volume=600 µl) was prepared as follows: 5× Reaction Buffer=120 µl and Nuclease-free water 480 µl. The tube of bead-DNA complex was placed on a magnetic rack for at least 1 minute. After the solution appeared clear, the supernatant was discarded. The bead-DNA was washed three times as follows: 500 µL of Bead Wash Buffer was added to the bead-DNA tube and placed on a magnetic rack for at least 1 minute. After the solution appeared clear, the supernatant was discarded. The bead-DNA was resuspended in 500 µL of 1× Reaction Buffer. The bead-DNA was vortexed for 15 seconds, then pulse-spun. The tube of bead-DNA complex was placed on a magnetic rack for at least 1 minute. After the solution appeared clear, the supernatant was discarded. The bead-DNA was resuspended in 87 µL of 1× Reaction Buffer.

Ligating Ion Adaptors to the DNA Library

The ligated library molecules are bound to streptavidin beads, washed and purified from ligation by-products. The bead-DNA is now ready for ligation to adaptors, such as primer, sequencing or other functionality adaptors. In this example, the bead-DNA was prepared for ligation to Ion Torrent™ sequencing specific adaptors (Life Technologies). Thus, the bead-DNA was prepared for ligation to P1 Adaptors Ion (top and bottom) and A Adaptors Ion (top and bottom) as shown in Table 23 below:

TABLE 23

| Component | Volume |
|---|---|
| DNA-bead complex | 87 |
| P1 Adaptor Ion (ds) | 1.5 |
| A Adaptor Ion (ds) | 1.5 |
| T4 DNA Ligase, 5 U/µL | 10 |
| Total Volume (µL) | 100 |

The ligation reaction was incubated at room temperature (20 to 25° C.) on a rotator for 30 minutes. The tube of bead-DNA-P1/A complex was placed on a magnetic rack for at least 1 minute. After the solution appeared clear, the supernatant was discarded. The beads were resuspended in 500 µL of Bead Wash Buffer, vortexed for 15 seconds, then pulse-spun. The tube of bead-DNA-P1/A complex was placed on a magnetic rack for at least 1 minute. After the solution appeared clear, the supernatant was discarded. The bead-DNA-P1/A complex was resuspended in 500 µL of Bead Wash Buffer, vortexed for 15 seconds, then pulse-spun. The tube of bead-DNA-P1/A complex was placed on a magnetic rack for at least 1 minute. After the solution appeared clear, the supernatant was discarded. The beads were resuspended in 500 µL of Bead Wash Buffer, vortexed for 15 seconds, then pulse-spun. The tube of bead-DNA-P1/A complex was placed on a magnetic rack for at least 1 minute. After the solution appeared clear, the supernatant was discarded. The beads were resuspended in 500 µL of Elution Buffer (E1). The tube of bead-DNA-P1/A complex was placed on a magnetic rack for 1 minute. After the solution appeared clear, the supernatant was discarded. The beads were resuspended in 30 µL of Elution Buffer (E1).

PCR Amplifying the Paired Tag Library

The paired tag library was amplified with a Platinum® PCR Amplification Mix (Invitrogen). The Platinum® PCR amplification mix contains a proofreading enzyme for high fidelity amplification and nick translation. Before conducting the final nick-translation and amplification step, a trial amplification of the PCR primer and Platinum® PCR Amplification Mix was performed to determine the optimum number of PCR cycles for each insert. PCR Primer 1 and PCR Primer 3 were pre-mixed at a final concentration of 5 µM in 10 mM Tris pH 7.5. The primer mix was then referred to as the Ion Library Amplification Primer Mix. A PCR reaction was set up as shown in Table 24 below:

TABLE 24

| Component | Volume |
|---|---|
| Platinum ® PCR Amplification Mix | 70 |
| Ion Library Amplification Primer Mix | 2.5 |
| Total Volume (µL) | 72.5 |

The master mix was vortexed. For a negative control, ~23 µL of the PCR master mix was added to a PCR tube (PCR #0). 4 µL of DNA-bead complex solution was added to the remaining 50 µL of PCR master mix, vortexed, then divided evenly (~25 µL) between two PCR tubes (tubes PCR #1 and 2). Each tube was subjected to thermocycling under the following conditions:

| Sample No. | No. of Cycles for 3 kb insert | No. of Cycles for 10 kb insert |
|---|---|---|
| 0 | 16 | 20 |
| 1 | 12 | 16 |
| 2 | 16 | 20 |

The thermocycler settings are provided in Table 25 below.

TABLE 25

| Stage | Step | Temp | Time |
|---|---|---|---|
| Holding | Nick Translation | 72° C. | 20 min |
| Holding | Denature | 94° C. | 5 min |
| Cycling | Denature | 94° C. | 15 sec |
|  | Anneal | 58° C. | 15 sec |
|  | Extend | 68° C. | 1 min |
| Holding | — | 4° C. | variable |

Amplification was confirmed using a pre-case 2% E-GEL EX GEL (Invitrogen). The presence of amplification product in the gel was used as an indicator to select the optimal number of cycles for amplification.

The paired tag library was amplified after determining the optimal thermocycling conditions (procedure outlined above). PCR Primer 1 and PCR Primer 3 were pre-mixed at a final concentration of 5 µM each. The primer mix was then referred to as the Ion Library Amplification Primer Mix. A PCR amplification reaction master mix was set up as shown in Table 26 below:

TABLE 26

| Component | Volume |
| --- | --- |
| Platinum ® PCR Amplification Mix | 200 |
| Ion Library Amplification Primer Mix | 10 |
| Total Volume (μL) | 210 |

The DNA-bead complex solution was placed on a magnetic rack for at least 1 minute. After the solution appeared clear, the supernatant was discarded being careful not to disturb the beads. The beads were resuspended in PCR master mix of Table 26 above, vortexed for 15 seconds, and loaded with the following settings into the thermocycler:

TABLE 27

| Stage | Step | Temp | Time |
| --- | --- | --- | --- |
| Holding | Nick Translation | 72° C. | 20 min |
| Holding | Denature | 94° C. | 5 min |
| Cycling | Denature | 94° C. | 15 sec |
|  | Anneal | 58° C. | 15 sec |
|  | Extend | 68° C. | 1 min |
| Holding | — | 4° C. | variable |

Purifying the DNA with SOLiD Library Micro Column Purification Kit

The amplified DNA was purified using SOLiD Library Micro Column Purification Kit. Empty PURELINK PCR Micro columns (Invitrogen) were pre-spun in collection tubes at 10,000×G for one minute. 4 volumes of Binding Buffer (B2-L) with isopropanol was added to 1 volume of sample and mixed well.

The entire PCR sample was loaded onto the PURELINK Micro column in a collection tube. The column was centrifuged at 10,000×xG for 1 minute at room temperature; the flow-through was discarded. The dsDNA is now bound to the column. The PURELINK Micro column was washed by adding 650 μL of Wash Buffer (W1) with ethanol to the column. The column was centrifuged at 10,000×xG for 1 minute at room temperature. The flow-through was discarded. The centrifugation was repeated at 14,000×xG to remove residual wash buffer. The column was transferred to a clean 1.5-mL LOBIND tube. 25 μL of Elution Buffer (E1) was loaded onto to the center of the column to elute the DNA. The column was allowed to stand for 1 minute at room temperature. The column was spun at 14,000×G for 1 minute. The eluate was loaded back onto the column, allowing the column to stand for 1 minute at room temperature. The column was spun at 14,000×G for 1 minute at room temperature.

Size Select the Library with a SOLiD Library Size Selection Gel

A size-selection step was performed to ensure a library of distinct size; however this step reduces the overall library yield. The size-selection step was conducted using a SOLiD™ Library Size Selection Gel. The library DNA sample was loaded onto a SOLiD Library Size Selection Gel (2%) and run according to the manufacturer's instructions. The gel was run until the library product entered the collection well. The collection well was flushed with 20 μl of nuclease free water.

Check the Size Distribution of the library

1 μl of the eluted library sample was analyzed using the Agilent Technologies 2100 Bioanalyzer™ to ensure the library was of the expected size distribution. The library was quantitated to determine the library dilution that results in a concentration within the optimized target range for Template Preparation (e.g., PCR-mediated addition of library molecules onto Ion Sphere™ Particles). The library is typically quantitated using an Ion Library Quantitation Kit (qPCR) (Life Technologies, Part No. 4468802) or Bioanalyzer™ (Agilent Technologies, Agilent 2100 Bioanalyzer) to determine the molar concentration of the library, from which the Template Dilution Factor is calculated. For example, instructions to determine the Template Dilution Factor by quantitative real-time PCR (qPCR) can be found in the Ion Library Quantitation Kit User Guide (Life Technologies, Part No. 4468986), hereby incorporated by reference in its entirety.

While the principles of the present teachings have been described in connection with specific embodiments of control sequencing templates and control microparticles, it should be understood clearly that these descriptions are made only by way of example and are not intended to limit the scope of the present teachings or claims. What has been disclosed herein has been provided for the purposes of illustration and description. It is not intended to be exhaustive or to limit what is disclosed to the precise forms described. Many modifications and variations will be apparent to the practitioner skilled in the art. What is disclosed was chosen and described in order to best explain the principles and practical application of the disclosed embodiments of the art described, thereby enabling others skilled in the art to understand the various embodiments and various modifications that are suited to the particular use contemplated. It is intended that the scope of what is disclosed be defined by the following claims and their equivalents.

What is claimed:

1. A method for circularizing a polynucleotide, comprising:

a) providing (i) a linear target polynucleotide having a first end and a second end, (ii) a first double-stranded nucleic acid adaptor with a target joining end and a first overhang end wherein the first overhang end comprises a first overhang nucleic acid sequence, (iii) and a second double-stranded nucleic acid adaptor with a target-joining end and a second overhang end wherein the second overhang end comprises a second overhang nucleic acid sequence, wherein the first and second overhang nucleic acid sequences being at least partially complementary to each other, wherein the first overhang is hybridized to a first single-stranded blocking oligonucleotide over at least a portion of its length and the second overhang is hybridized to a second single-stranded blocking oligonucleotide over at least a portion of its length, and wherein the target-joining end of the first double-stranded nucleic acid adaptor is joined to the first end of the linear target polynucleotide and the target joining end of the second double-stranded nucleic acid adaptor is joined to the second end of the linear target polynucleotide;

b) removing the first and the second single-stranded blocking oligonucleotides from the first and the second overhangs; and c) hybridizing the first overhang having a first nucleic acid sequence with the second overhang having a second nucleic acid sequence, thereby circularizing the polynucleotide, wherein the first and second overhangs are not enzymatically ligated together.

2. The method of claim 1, wherein the first and the second single-stranded blocking oligonucleotides are not hybridized to each other.

3. The method of claim 1, wherein the removing comprises denaturing the first single-stranded blocking oligonucleotide from the first overhang and denaturing the second single-stranded blocking oligonucleotide from the second overhang.

4. The method of claim 1, wherein circularizing the polynucleotide includes forming a junction on each nucleic acid strand between the first and second overhangs.

5. The method of claim 4, wherein at least one junction comprises a nick.

6. The method of claim 4, wherein the circularized polynucleotide includes two nicks.

7. The method of claim 6, further comprising the step: moving each of the two nicks to a new position within the circularized polynucleotide.

8. The method of claim 7, wherein the moving the two nick comprises performing a nick translation reaction on the two nicks.

9. The method of claim 8, wherein the nick translation reaction is a coupled 5' to 3' DNA polymerization/degradation reaction, or is a coupled 5' to 3' DNA polymerization/strand displacement reaction.

10. The method of claim 8, wherein the length of time of the nick translation reaction is modulated to increase or decrease the distance to move the two nick to a new position within the circularized polynucleotide.

11. The method of claim 7, further comprising cleaving the circularized polynucleotide with a single-strand specific endonuclease enzyme at the new position of the two nicks to release a linear polynucleotide which includes a mate pair construct.

12. The method of claim 1, wherein the first double-stranded nucleic acid adaptor comprises biotin, or the second double-stranded nucleic acid adaptor comprises biotin, or the first and second double-stranded nucleic acid adaptors comprise biotin.

13. The method of claim 12, further comprising the step of reacting the biotin with streptavidin.

14. The method of claim 11, further comprising joining the ends of the released linear polynucleotide to additional adaptors to generate an adaptor-mate pair construct.

15. The method of claim 14, further comprising attaching the adaptor-mate pair construct to a surface.

16. The method of claim 15, further comprising sequencing the adaptor-mate pair construct.

\* \* \* \* \*

SEQUENCE LISTING

<160> NUMBER OF SEQ ID NOS: 133

<210> SEQ ID NO 1
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1
ctgctgtacc gtacatccgc cttg                    24

<210> SEQ ID NO 2
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 2
acggtacagc ag                                                            12

<210> SEQ ID NO 3
<211> LENGTH: 11
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 3
aaggcggatg t                                                             11

<210> SEQ ID NO 4
<211> LENGTH: 11
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 4
catccgcctt g                                                             11

<210> SEQ ID NO 5
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 5
gccgtacagc ag                                                            12

<210> SEQ ID NO 6
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 6
ctgctgtacg gccaaggcgg atgt                                               24

<210> SEQ ID NO 7
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 7
ctgctgtacc gtacatccgc cttg                                    24

<210> SEQ ID NO 8
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 8
ctgctgtacg gccaaggcgg atgt                                    24

<210> SEQ ID NO 9
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 9
ctgctgtacc gtacatccgc cttggccgta cagcag                       36

<210> SEQ ID NO 10
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 10
ctgctgtacg gccaaggcgg atgtacggta cagcag                       36

<210> SEQ ID NO 11
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 11
acatccgcct tg                                                 12

<210> SEQ ID NO 12
<211> LENGTH: 9
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 12 gtacagcag                                                      9

<210> SEQ ID NO 13
<211> LENGTH: 27
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 13
ctgctgtacg gccaaggcgg atgtacg                                              27

<210> SEQ ID NO 14
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 14
ctgctgtacc gtacatccgc cttggcc                                              27

<210> SEQ ID NO 15
<211> LENGTH: 9
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 15 gtacagcag                                                                   9

<210> SEQ ID NO 16
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 16
caaggcggat gt                                                              12

<210> SEQ ID NO 17
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 17
ctgctgtacc gtacatccgc cttggccgta cagcag                                    36

<210> SEQ ID NO 18
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 18
ctgctgtacg gccaaggcgg atgtacggta cagcag                                    36
```

<210> SEQ ID NO 19
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 19
ctgctgtacg gccaaggcgg atgt                                         24

<210> SEQ ID NO 20
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 20
gccgtacagc ag                                                      12

<210> SEQ ID NO 21
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 21
attataattg cggccgc                                                 17

<210> SEQ ID NO 22
<211> LENGTH: 9
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 22 aattataat                                                           9

<210> SEQ ID NO 23
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 23
ccactacgcc tccgctttcc tctctatggg cagtcggtga t                       41

<210> SEQ ID NO 24
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 24
tcaccgactg cccatagaga ggaaagcgga ggcgtagtgg cc        42

<210> SEQ ID NO 25
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 25
gagaatgagg aacccggggc agcc        24

<210> SEQ ID NO 26
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 26
ctgccccggg ttcctcattc tct        23

<210> SEQ ID NO 27
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 27
ccactacgcc tccgctttcc tctctatg        28

<210> SEQ ID NO 28
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 28
ctgccccggg ttcctcattc t        21

<210> SEQ ID NO 29
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 29
ccatctcatc cctgcgtgtc        20

<210> SEQ ID NO 30
<211> LENGTH: 41

<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 30
ccactacgcc tccgctttcc tctctatggg cagtcggtga t                    41

<210> SEQ ID NO 31
<211> LENGTH: 43
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 31
atcaccgact gcccatagag aggaaagcgg aggcgtagtg gtt                  43

<210> SEQ ID NO 32
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 32
ccatctcatc cctgcgtgtc tccgactcag                                 30

<210> SEQ ID NO 33
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 33
ctgagtcgga gacacgcagg gatgagatgg tt                              32

<210> SEQ ID NO 34
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 34
cctcttacac                                                       10

<210> SEQ ID NO 35
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 35
accactccct 10

<210> SEQ ID NO 36
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 36
tataacctat 10

<210> SEQ ID NO 37
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 37
gaccgcatcc 10

<210> SEQ ID NO 38
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 38
cttacaccac 10

<210> SEQ ID NO 39
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 39
tgtccctcgc 10

<210> SEQ ID NO 40
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 40
ggcataaccc 10

<210> SEQ ID NO 41
<211> LENGTH: 10
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 41
atcctcgctc                                                              10

<210> SEQ ID NO 42
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 42
gtcgcaacct                                                              10

<210> SEQ ID NO 43
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 43
agcttaccgc                                                              10

<210> SEQ ID NO 44
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 44
cgtgtcgcac                                                              10

<210> SEQ ID NO 45
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 45
ttttcctctt                                                              10

<210> SEQ ID NO 46
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 46
gccttaccgc                                                              10

<210> SEQ ID NO 47
```

```
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 47
tctgccgcac                                                               10

<210> SEQ ID NO 48
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 48
cattcaactc                                                               10

<210> SEQ ID NO 49
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 49
aacgtctccc                                                               10

<210> SEQ ID NO 50
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 50
gcggtgagcc                                                               10

<210> SEQ ID NO 51
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 51
tcatccgcct                                                               10

<210> SEQ ID NO 52
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 52
```
cagttaccat                                                                          10

<210> SEQ ID NO 53
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 53
aaagcttgac                                                                          10

<210> SEQ ID NO 54
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 54
ggaaccgcac                                                                          10

<210> SEQ ID NO 55
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 55
tcatcttctc                                                                          10

<210> SEQ ID NO 56
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 56
caagcaccgc                                                                          10

<210> SEQ ID NO 57
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 57
ataccgaccc                                                                          10

<210> SEQ ID NO 58
<211> LENGTH: 10
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 58
tcatcatgtt                                                           10

<210> SEQ ID NO 59
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 59
cgggctcccg                                                           10

<210> SEQ ID NO 60
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 60
aagtttgctg                                                           10

<210> SEQ ID NO 61
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 61
gtagtaagct                                                           10

<210> SEQ ID NO 62
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 62
ccctagattc                                                           10

<210> SEQ ID NO 63
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 63
tcttcgctac                                                           10
```

```
<210> SEQ ID NO 64
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 64
acgcaccagc                                                              10

<210> SEQ ID NO 65
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 65
gcacccaacc                                                              10

<210> SEQ ID NO 66
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 66
gtatccaacg                                                              10

<210> SEQ ID NO 67
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 67
cctttaacga                                                              10

<210> SEQ ID NO 68
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 68
tcctacgctt                                                              10

<210> SEQ ID NO 69
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 69
atgtgagaac                                                          10

<210> SEQ ID NO 70
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 70
ggtataacag                                                          10

<210> SEQ ID NO 71
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 71
ctaagacgac                                                          10

<210> SEQ ID NO 72
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 72
actcacgata                                                          10

<210> SEQ ID NO 73
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 73
taacccttt                                                           10

<210> SEQ ID NO 74
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 74
caatcccaca                                                          10

<210> SEQ ID NO 75
<211> LENGTH: 10
<212> TYPE: DNA
<213> ORGANISM: Artificial Sequence
```

-continued

```
<220> FEATURE:
<221> NAME/KEY: source
<223> OTHER INFORMATION: /note="Description of Artificial Sequence:
      Synthetic oligonucleotide"

<400> SEQUENCE: 75
tagtacattc                                                            10

<210> SEQ ID NO 76
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 76
aaccctagcg                                                            10

<210> SEQ ID NO 77
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 77
gatcatcctt                                                            10

<210> SEQ ID NO 78
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 78
agccaagtac                                                            10

<210> SEQ ID NO 79
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 79
ttcgacgacc                                                            10

<210> SEQ ID NO 80
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 80
gccatccctc                                                            10
```

<210> SEQ ID NO 81
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 81
cacttacggc                                                                                          10

<210> SEQ ID NO 82
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 82
cttatgacat                                                                                          10

<210> SEQ ID NO 83
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 83
gcaagccttc                                                                                          10

<210> SEQ ID NO 84
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 84
actcctgctt                                                                                          10

<210> SEQ ID NO 85
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 85
ttacaattac                                                                                          10

<210> SEQ ID NO 86
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 86
acttgatgac                                                                              10

<210> SEQ ID NO 87
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 87
tccgccttt                                                                               10

<210> SEQ ID NO 88
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 88
cgcttaagct                                                                              10

<210> SEQ ID NO 89
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 89
ggtgacatgc                                                                              10

<210> SEQ ID NO 90
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 90
ttcttactag                                                                              10

<210> SEQ ID NO 91
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 91
cgccacttta                                                                              10

<210> SEQ ID NO 92
<211> LENGTH: 10
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 92
gacattactt                                                                10

<210> SEQ ID NO 93
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 93
accgaggcac                                                                10

<210> SEQ ID NO 94
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 94
cgataatctt                                                                10

<210> SEQ ID NO 95
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 95
accctcacct                                                                10

<210> SEQ ID NO 96
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 96
tcgaacccgc                                                                10

<210> SEQ ID NO 97
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 97
ggtgtagcac                                                                10
```

```
<210> SEQ ID NO 98
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 98
gcttgatccc                                                            10

<210> SEQ ID NO 99
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 99
acattacatc                                                            10

<210> SEQ ID NO 100
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 100
ccctaaggac                                                            10

<210> SEQ ID NO 101
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 101
tcgtcaatgc                                                            10

<210> SEQ ID NO 102
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 102
aaagcatatc                                                            10

<210> SEQ ID NO 103
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
```

-continued

Synthetic oligonucleotide"

<400> SEQUENCE: 103
tctgtagggc                                                          10

<210> SEQ ID NO 104
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 104
cgttccctgt                                                          10

<210> SEQ ID NO 105
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 105
gtattcactt                                                          10

<210> SEQ ID NO 106
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 106
acgtcattgc                                                          10

<210> SEQ ID NO 107
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 107
tcagcgtcct                                                          10

<210> SEQ ID NO 108
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 108
gcccagatac                                                          10

<210> SEQ ID NO 109
<211> LENGTH: 10

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 109
cctaaaactt                                                                10

<210> SEQ ID NO 110
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 110
aagaccagat                                                                10

<210> SEQ ID NO 111
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 111
gatgattgcc                                                                10

<210> SEQ ID NO 112
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 112
taattctact                                                                10

<210> SEQ ID NO 113
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 113
caccgtaaac                                                                10

<210> SEQ ID NO 114
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 114
```
aatgacgttc                                                          10

<210> SEQ ID NO 115
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 115
ctcccttcac                                                          10

<210> SEQ ID NO 116
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 116
tacgccatcc                                                          10

<210> SEQ ID NO 117
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 117
gttcatccgc                                                          10

<210> SEQ ID NO 118
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 118
aacgctttcc                                                          10

<210> SEQ ID NO 119
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 119
tcctggtact                                                          10

<210> SEQ ID NO 120
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
       Synthetic oligonucleotide"

<400> SEQUENCE: 120
gctttgctat                                                              10

<210> SEQ ID NO 121
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
       Synthetic oligonucleotide"

<400> SEQUENCE: 121
catgatcaac                                                              10

<210> SEQ ID NO 122
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
       Synthetic oligonucleotide"

<400> SEQUENCE: 122
tagacagcct                                                              10

<210> SEQ ID NO 123
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
       Synthetic oligonucleotide"

<400> SEQUENCE: 123
agtaggtcac                                                              10

<210> SEQ ID NO 124
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
       Synthetic oligonucleotide"

<400> SEQUENCE: 124
cccaatacgc                                                              10

<210> SEQ ID NO 125
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
       Synthetic oligonucleotide"

<400> SEQUENCE: 125
gtaatccctt                                                              10

<210> SEQ ID NO 126

```
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 126
gcatcgtaac                                                              10

<210> SEQ ID NO 127
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 127
aaacacccat                                                              10

<210> SEQ ID NO 128
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 128
tgccggactc                                                              10

<210> SEQ ID NO 129
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 129
ctcttcgatt                                                              10

<210> SEQ ID NO 130
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 130
gccgtacagc ag                                                           12

<210> SEQ ID NO 131
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 131
```

```
acggtacagc ag                                                              12

<210> SEQ ID NO 132
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 132
aaggcggatg tacggtacag cag                                                  23

<210> SEQ ID NO 133
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 133
catccgcctt ggccgtacag cag                                                  23
```